US008813570B2

(12) United States Patent
Matsumoto et al.

(10) Patent No.: US 8,813,570 B2
(45) Date of Patent: Aug. 26, 2014

(54) ULTRASONIC MEASURING METHOD AND ULTRASONIC MEASURING SYSTEM

(75) Inventors: Seiichi Matsumoto, Toyota (JP); Hiroyuki Kawaki, Toyota (JP); Shinya Kuroki, Toyota (JP); Kazuhiro Uchida, Ama (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 288 days.

(21) Appl. No.: 13/431,022

(22) Filed: Mar. 27, 2012

(65) Prior Publication Data

US 2012/0247211 A1    Oct. 4, 2012

(30) Foreign Application Priority Data

Mar. 28, 2011   (JP) ................................ 2011-071007
Mar. 5, 2012    (JP) ................................ 2012-047543

(51) Int. Cl.
*G01N 29/30*   (2006.01)
(52) U.S. Cl.
USPC ............................................. 73/632; 73/599
(58) Field of Classification Search
USPC .......... 73/632, 1.82, 588, 597, 599, 602, 627, 73/866
See application file for complete search history.

(56) References Cited

U.S. PATENT DOCUMENTS

| | | | | |
|---|---|---|---|---|
| 4,117,732 A | * | 10/1978 | Brazhnikov | ..................... 73/599 |
| 4,437,332 A | * | 3/1984 | Pittaro | ........................... 73/597 |
| 4,569,037 A | | 2/1986 | Seiferling | |
| 5,408,881 A | * | 4/1995 | Piche et al. | ..................... 73/582 |
| 5,557,970 A | * | 9/1996 | Abbate et al. | ................... 73/597 |
| 5,723,791 A | * | 3/1998 | Koch et al. | ....................... 73/597 |
| 5,777,230 A | * | 7/1998 | Vandervalk | ..................... 73/632 |

FOREIGN PATENT DOCUMENTS

| | | |
|---|---|---|
| JP | 61-104277 | 5/1986 |
| JP | 3-200061 | 9/1991 |
| JP | 9-152326 | 6/1997 |
| JP | 10-154219 | 6/1998 |
| JP | 2000-180146 | 6/2000 |
| JP | 2002-42789 | 2/2002 |
| JP | 2004-156917 | 6/2004 |
| JP | 2005-249486 | 9/2005 |
| JP | 2008-102160 | 5/2008 |

* cited by examiner

*Primary Examiner* — J M Saint Surin
(74) *Attorney, Agent, or Firm* — Finnegan, Henderson, Farabow, Garrett & Dunner, LLP

(57) ABSTRACT

An ultrasonic measuring method and an ultrasonic measuring system use or include at least one actual-measurement ultrasonic sensor set each consisting of a first ultrasonic sensor and a second ultrasonic sensor, for measuring the basis weight of an electrode paste, and a calibration ultrasonic sensor set consisting of a pair of first calibration ultrasonic sensor and second calibration ultrasonic sensor. The calibration ultrasonic sensor set performs calibration during measurement of the thickness of the electrode paste, and the actual-measurement ultrasonic sensor set calculates the basis weight of the electrode paste, using a measurement condition value obtained by the calibration ultrasonic sensor set.

20 Claims, 25 Drawing Sheets

F I G . 19
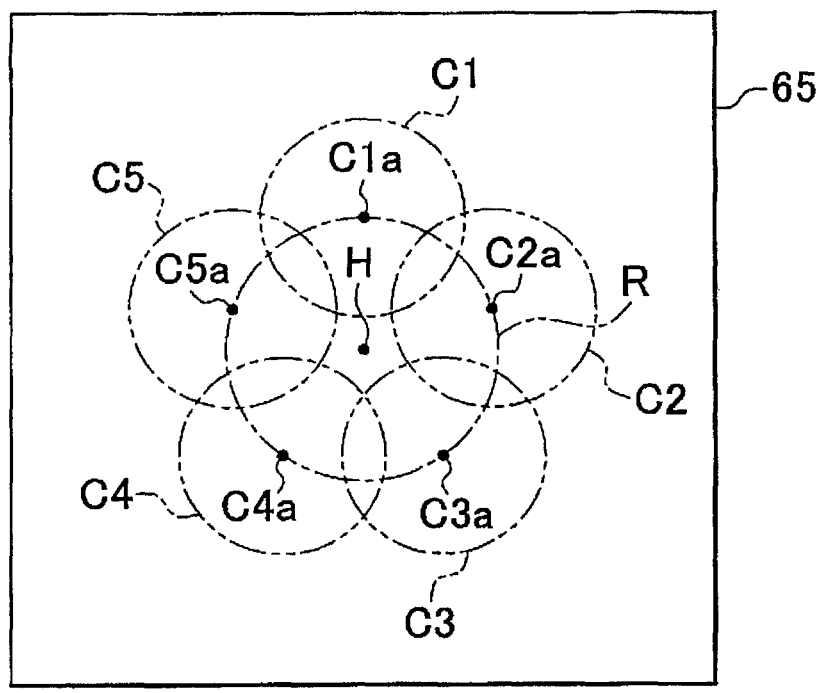

F I G . 27
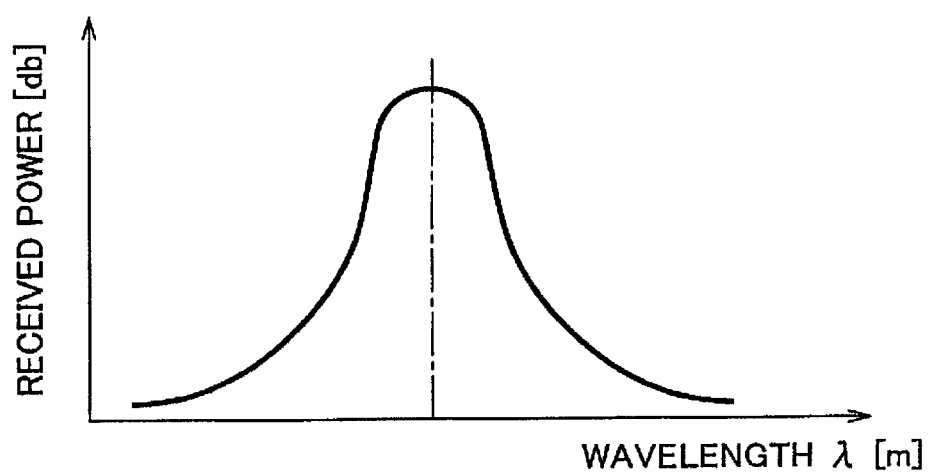

ULTRASONIC MEASURING METHOD AND ULTRASONIC MEASURING SYSTEM

INCORPORATION BY REFERENCE

The disclosure of Japanese Patent Applications No. 2011-071007 filed on Mar. 28, 2011 and No. 2012-047543 filed on Mar. 5, 2012 including the specifications, drawings and abstracts is incorporated herein by reference in its entirety.

BACKGROUND OF THE INVENTION

1. Field of the Invention

The invention relates to ultrasonic measuring method and ultrasonic measuring system for measuring the thickness of a coating material, such as the basis weight of electrode paste applied by coating to a metal foil on an electrode production line in a battery production process, for example, during operation of the line.

2. Description of the Related Art

The battery production process includes a step of producing electrodes from an electrode sheet formed by applying electrode paste by coating to a metal foil on an electrode production line. Since the quality of the electrodes has a large influence on the performance of batteries as final products, it is important, for quality control, to conduct quality check regarding the basis weight (or coating weight) and coating profile of the electrode paste, after it is applied by coating to the metal foil. In some cases, the quality check as described above is desired to be conducted evenly or uniformly over a wide range of the electrode paste of the electrode, on the electrode production line.

Thus, the applicant of this application proposed to make a 100% inspection of the basis weight and coating profile of the electrode paste, on the electrode production line, with respect to all of the electrodes produced on the line, using an ultrasonic measuring system as disclosed in Japanese Patent Application Publication No. 2008-102160 (JP 2008-102160 A), for example. FIG. 24 is an explanatory view showing the ultrasonic measuring system as disclosed in JP 2008-102160 A. As shown in FIG. 24, the ultrasonic measuring system has a pair of ultrasound sending means 81 and ultrasound receiving means 82, which are placed above a measurement object 90, and incident waves sent from the ultrasound sending means 81 are transmitted through the measurement object 90, so that the ultrasound receiving means 82 receives the reflected waves from the measurement object 90.

In the ultrasonic measuring system of JP 2008-102160 A, a propagation time measuring means 83 measures the propagation time of ultrasonic waves propagated through the measurement object 90, based on an incident signal of the ultrasound sending means 81 and a reflection signal received by the ultrasound receiving means 82. Also, temperature measuring means 94a, 94b measure respective temperatures of a liquid phase 91 and a solid phase 92 that constitute the measurement object 90, and a velocity correcting means 85 corrects the propagation velocity of ultrasonic waves propagated, based on the measured temperatures of the liquid phase 91 and solid phase 92, which are measured by the temperature measuring means 94a, 94b. A propagation path length measuring means 86 measures the thickness of the measurement object 90, and a phase-change position of the measurement object 90 as a laminate of the liquid phase 91 and the solid phase 92, based on the propagation time of ultrasonic waves obtained by the propagation time measuring means 83, and a correction value of the propagation velocity obtained by the velocity correcting means 85.

Although calibration of the ultrasound sending means 81 and ultrasonic receiving means 82 is not mentioned in JP 2008-102160 A, calibration of ultrasonic sensors for sending (or receiving) ultrasonic waves is generally conducted in ultrasonic measuring systems of the related art, such as that of JP 2008-102160 A. The calibration is normally conducted while actual measurement of the thickness, distance, or the like, of a measurement object (which will be referred to as "ultrasonic measurement") is not carried out, for example, before or after the ultrasonic measurement is carried out by an ultrasonic sensor(s), or when the actual measurement is interrupted or stopped, so as to reduce measurement errors in the ultrasonic sensors during measurement.

However, the above-described system of the related art has the following two problems. (1) In the ultrasonic measuring system of JP 2008-102160 A, ultrasonic waves sent from the ultrasound sending means 81 toward the measurement object 90, and ultrasonic waves reflected by the measurement object 90 and received by the ultrasonic receiving means 82 propagate through an air layer as a medium other than the measurement object 90. If the temperature of the air layer is not controlled, the acoustic impedance in the air layer varies with changes in the temperature of the air layer. If the acoustic impedance in the air layer varies, the wavelength of ultrasonic waves propagated through the air layer varies. As a result, the thickness, or the like, of the measurement object 90 cannot be accurately obtained only through correction of the propagation velocity of ultrasonic waves by the velocity correcting means 85.

(2) Also, if the calibration of the ultrasonic sensors is not carried out in real time during actual ultrasonic measurement, the temperature of the atmosphere of the ultrasonic sensors may largely differ between the time when the calibration is carried out, and the time when the actual ultrasonic measurement is carried out. In this case, the intensity of a received signal of a receiving-side ultrasonic sensor that receives ultrasonic waves, for example, may largely change due to the atmosphere temperature.

As one example of the above situation, the graph of FIG. 25 shows test results indicating the relationship between the intensity of the received signal of the receiving-side ultrasonic sensor and the temperature of the atmosphere. In the test, two samples of receiving-side ultrasonic sensors of the same frequency band, which are denoted as Sensor A and Sensor B in FIG. 25, are used. As shown in FIG. 25, the intensities of the received signals of the sensors A, B were both about 825 (mV) when the temperature of the atmosphere was in the neighborhood of 20° C., but the received signal intensities became lower than 780 (mV) when the temperature of the atmosphere exceeded 23° C. It is thus understood that the received signal intensity is reduced by 5% or more, with a temperature rise of 3° C.

As one characteristic of ultrasonic sensors, the ultrasonic sensor is self-heated with a lapse of time in which the sensor is in an operating condition, i.e., the sensor is sending or receiving ultrasonic waves. The graph of FIG. 26 shows, as one example, the relationship between self-heating (the temperature of a receiving-side ultrasonic sensor) and the intensity of ultrasonic waves received by the sensor. As shown in FIG. 26, the temperature of the receiving-side ultrasonic sensor was about 28.5° C. at the time when the sensor starts being operated (t=0 (min.)), but is raised to about 30.7° C. due to heating of the sensor itself, at t=120 (min.) after the start of the operation. On the other hand, it is found that, upon a lapse of two hours from the start of the operation, the received signal intensity is reduced from about 76,200 (mV) down to about 72,300 (mV), namely, reduced by about 5% as compared with that obtained when the operation is started.

In ultrasonic sensors, there is generally a certain correlation between the magnitude of received power of ultrasonic waves (ultrasonic intensity), which is substantially equivalent to the received signal intensity as indicated in FIG. 27, and the wavelength of received ultrasonic waves, as a characteristic of sonic propagation. The graph of FIG. 27 indicates the relationship between the wavelength of the received ultrasonic waves and the ultrasonic intensity. The ultrasonic intensity changes along a normal distribution curve having a peak value at a given wavelength, as shown in FIG. 27. If the wavelength shifts to be a little shorter or longer than the given wavelength corresponding to the peak value, the ultrasonic intensity is reduced largely from the peak value.

Thus, the ultrasonic intensity of the same receiving-side ultrasonic sensor largely changes when the atmosphere temperature of the ultrasonic sensor differs between the time when calibration is performed and the time when the actual ultrasonic measurement is performed, and when the ultrasonic sensor is self-heated; therefore, the wavelength of ultrasonic waves received by the receiving-side ultrasonic sensor largely changes, as is read from FIG. 27. The computation or calculation for the ultrasonic measurement is performed based on the wavelength of the received ultrasonic waves. Therefore, even if calibration is appropriately conducted, the wavelength of ultrasonic waves received by the same receiving-side ultrasonic sensor differs due to a difference in the temperature of the atmosphere of the ultrasonic sensor, and self-heating, unless the calibration is carried out in real time during the actual ultrasonic measurement, and the ultrasonic measurement cannot be accomplished with high accuracy.

SUMMARY OF THE INVENTION

In view of the above problems, the present invention provides ultrasonic measuring method and ultrasonic measuring system with which the thickness of a coating material applied by coating to a coated product produced on a production line can be measured on the production line, with high accuracy.

According to one aspect of the invention, an ultrasonic measuring method is provided which includes the steps of: providing at least one set of ultrasonic sensors, each of which comprises a pair of first ultrasonic sensor and second ultrasonic sensor, and placing the first ultrasonic sensor on one side of a coated product formed by applying a coating material by coating to one surface or both surfaces of a substrate made of metal and wound in the form of a roll, as viewed in a thickness direction of the coated product, via an air layer, while placing the second ultrasonic sensor on the other side of the coated product, via an air layer, and measuring a thickness of the coating material by transmitting ultrasonic waves between the first ultrasonic sensor and the second ultrasonic sensor, wherein the above-indicated at least one set of ultrasonic sensors includes at least one actual-measurement ultrasonic sensor set that measures the thickness of the coating material, and a calibration ultrasonic sensor set comprising a pair of first calibration ultrasonic sensor and second calibration ultrasonic sensor, aside from the first ultrasonic sensor and the second ultrasonic sensor, and the calibration ultrasonic sensor set performs calibration, during measurement of the thickness of the coating material, and the actual-measurement ultrasonic sensor set calculates the thickness of the coating material, using a measurement condition value obtained by the calibration ultrasonic sensor set.

According to the ultrasonic measuring method as described above, when the thickness of the coating material, such as the basis weight of the coating material, is measured on the production line on which the electrode (coated product) is produced by coating the metal foil (substrate) with the electrode paste (coating material), in the battery production process, error factors of the measurement accuracy due to self-heating of the ultrasonic sensors and changes in the temperature of the air layers can be excluded or eliminated, and the thickness (such as the basis weight) of the coating material can be measured with improved accuracy.

Namely, in the ultrasonic measuring method as described above, the calibration ultrasonic sensor set performs calibration, and the actual-measurement ultrasonic sensor set measures the thickness of the coating material, using the measurement condition value obtained form the calibration ultrasonic sensor set, in real time during the actual measurement of the thickness of the coating material.

Here, the relationship between the ultrasonic sensors (the first ultrasonic sensor, the second ultrasonic sensor, the first calibration ultrasonic sensor, and the second calibration ultrasonic sensor), and the sound velocity, density, and acoustic impedance in the air layer will be briefly described. The sound velocity, density, and acoustic impedance in the air layer are determined according to the following equations.

$$\text{Sound Velocity } C = f \times \lambda \tag{1}$$

where C is the sound velocity (m/sec), f is the frequency of the ultrasonic sensor (kHz), and $\lambda$ is the wavelength (m).

The sound velocity may also be expressed by:

$$C = 331.5 + (0.61 \times t) \tag{2}$$

where t is the temperature (° C.).

$$\text{Density } \rho = 1.293 \times (273.15/(273.15+t)) \times (P/1013.25) \tag{3}$$

where $\rho$ is the density (kg/m$^3$) (ntp), t is the temperature (° C.), and P is the atmospheric pressure (atm).

$$\text{Acoustic Impedance } Z = \rho \times C \tag{4}$$

where Z is the acoustic impedance (Pa·s/m).

Under the atmospheric pressure, the sound velocity, density, and acoustic impedance in the air layer vary with the temperature of the air layer, as indicated in Eq. (2) through Eq. (4). If the frequency f is regarded as a constant in Eq. (1), the wavelength $\lambda$ also varies with the temperature of the air layer.

As in the ultrasonic measuring system as described in JP 2008-102160 A, ultrasonic waves are transmitted, via the air layer, between the first ultrasonic sensor and the second ultrasonic sensor. However, in the ultrasonic measuring method of this invention, the actual-measurement ultrasonic sensor set actually measures the thickness of the coating material, while adopting measurement condition values, such as the sound velocity, density, and acoustic impedance in the air layer, and the wavelength of transmitted ultrasonic waves, which vary as parameters with changes in the temperature of the air layer, from the calibration ultrasonic sensor set, in real time during measurement of the thickness of the coating material. Therefore, even if the temperature of the air layer between the first ultrasonic sensor and the second ultrasonic sensor changes during measurement, the actual-measurement ultrasonic sensor set is able to calculate the thickness of the coating material, based on the wavelength corresponding to the actual temperature during actual measurement, as described above, under the measurement condition values corrected in the calibration ultrasonic sensor set.

In the ultrasonic measuring method of the related art in which calibration is not performed at the same time as the actual ultrasonic measurement, even if the same receiving-side ultrasonic sensor is used, the wavelength of ultrasonic waves received by the sensor differs or varies as the temperature of the atmosphere (the air layer) of the ultrasonic sensor varies, or due to self-heating of the sensor, and the ultrasonic measurement cannot be made with high accuracy. On the other hand, in the ultrasonic measuring method of the invention, the actual-measurement ultrasonic sensor set actually measures the thickness of the coating material, using the measurement condition values obtained by the calibration ultrasonic sensor set, in real time during measurement of the thickness of the coating material. Thus, there is no difference in the temperature of the air layer, between the time when the thickness is actually measured by the first and second ultrasonic sensors, and the time when calibration is performed by the first and second calibration ultrasonic sensors.

With the first and second ultrasonic sensors and the first and second calibration ultrasonic sensors operating in the same timing, even if the first and second ultrasonic sensors are self-heated with a lapse of the operating time, the first and second calibration ultrasonic sensors are also self-heated in the same fashion as the first and second ultrasonic sensors. In this case, there are almost no differences between the temperatures of the self-heated first and second ultrasonic sensors and the temperatures of the self-heated first and second calibration ultrasonic sensors. Therefore, even if the wavelength of ultrasonic waves received by the calibration ultrasonic sensor set changes due to self-heating, the wavelength of ultrasonic waves received by the actual-measurement ultrasonic sensor set also changes in the same manner as that of the calibration ultrasonic sensor set. Thus, there arises almost no difference between the wavelength of the actual-measurement ultrasonic sensor set and the wavelength of the calibration ultrasonic sensor set, and the thickness (such as the basis weight) of the coating material can be measured with higher accuracy even when the first and second calibration ultrasonic sensors of the calibration ultrasonic sensor set and the first and second ultrasonic sensors of the actual-measurement ultrasonic sensor set are both self-heated.

Thus, according to the ultrasonic measuring method of the invention, error factors of the measurement accuracy due to self-heating of the ultrasonic sensors and changes in the temperature of the air layer can be excluded or eliminated, so that the thickness (such as the basis weight) of the coating material applied by coating to the coated product produced on the production line can be advantageously measured on the production line with high accuracy.

In the ultrasonic measuring method as described above, flat-type ultrasonic sensors that permit propagation of unfocused ultrasonic waves may be used as the first calibration ultrasonic sensor and the second calibration ultrasonic sensor of the calibration ultrasonic sensor set, and flat-type ultrasonic sensors that permit propagation of unfocused ultrasonic waves may be used as the first ultrasonic sensor and the second ultrasonic sensor of each of said at least one actual-measurement ultrasonic sensor set. In the ultrasonic measuring method of the invention, "the flat-type ultrasonic sensor that permits propagation of unfocused ultrasonic waves", in the case where the ultrasonic sensor is a transmitting sensor, means an ultrasonic sensor having an ultrasonic vibration surface from which ultrasonic waves are transmitted, wherein the ultrasonic vibration surface consists of a single vibration surface or two or more vibration surfaces (sections), and the overall shape of the ultrasonic vibration surface is, for example, a rectangular shape, circular shape, or the like. Also, the ultrasonic waves sent from the flat-type ultrasonic sensor can be transmitted, via the air layer, to at least within an area of the coated product which is opposed to the ultrasonic vibration surface of the ultrasonic sensor. Also, "the flat-type ultrasonic sensor", in the case where it is a receiving sensor, means an ultrasonic sensor having an ultrasonic vibration surface that receives ultrasonic waves, wherein the ultrasonic vibration surface consists of a single vibration surface or two or more vibration surfaces (sections), and the overall shape of the ultrasonic vibration surface is, for example, a rectangular shape, circular shape, or the like. In operation, the entire area of the ultrasonic vibration surface of the ultrasonic sensor can receive the ultrasonic waves (transmitted waves) sent from the other ultrasonic sensor for irradiation and transmitted through at least the coated product, via the air layer.

According to the ultrasonic measuring method as described above, the receiving-side ultrasonic sensor that receives ultrasonic waves, as one of the first ultrasonic sensor and the second ultrasonic sensor of the actual-measurement ultrasonic sensor set, provides a received signal for determining the thickness of the coating material, over a wider region or range of the coated product, as compared with a spot-type ultrasonic sensor that permits propagation of focused ultrasonic waves to within a local or narrow region. Therefore, quality, check regarding the thickness of the coating material, such as the basis weight and coating profile of the electrode paste as illustrated above, can be carried out on the production line of the coated product.

Since the received signal received by the receiving-side ultrasonic sensor can be obtained from a wide range of the coated product, the thickness of the coating material over a wide range of the coated product can be detected; therefore, variations in the thickness of the coating material within the measurement range can be grasped with improved accuracy, and the overall thickness of the coating material, such as the basis weight of the coating material, within a given range of the coated product can be measured with high reliability.

All of the first calibration ultrasonic sensor and second calibration ultrasonic sensor of the calibration ultrasonic sensor set, and the first ultrasonic sensor and second ultrasonic sensor of the actual-measurement ultrasonic sensor set are flat-type ultrasonic sensors. Therefore, no differences in characteristics due to differences in the forms of the ultrasonic vibration surfaces of the ultrasonic sensors appear between the calibration ultrasonic sensor set and the actual-measurement ultrasonic sensor set, and the actual-measurement ultrasonic sensor set can acquire the measurement condition values obtained through calibration by the calibration ultrasonic sensor set, with high accuracy, in an appropriate condition.

In the ultrasonic measuring method of the invention, the first ultrasonic sensor, second ultrasonic sensor, first calibration ultrasonic sensor, and second calibration ultrasonic sensor preferably have nominal frequencies that are in the same frequency band. Also, ultrasonic sensors capable of sending and receiving ultrasonic waves are preferably used as the first ultrasonic sensor and the second ultrasonic sensor, and the first calibration ultrasonic sensor and the second calibration ultrasonic sensor.

In the ultrasonic measuring method as described above, prior to actual measurement by the actual-measurement ultrasonic sensor set, a reference foil used for calibration may be placed between the first calibration ultrasonic sensor and the second calibration ultrasonic sensor of the calibration ultrasonic sensor set, and ultrasonic waves sent from the first calibration ultrasonic sensor may be transmitted through the reference foil, so that a first received signal representing ultrasonic waves received by the second calibration ultrasonic sensor is obtained in advance as the measurement condition value. Also, the actual-measurement ultrasonic sensor set may obtain a second received signal representing ultrasonic waves transmitted through the coated product between the first ultrasonic sensor and the second ultrasonic sensor, and the thickness of the coating material may be calculated based on the relative ratio of the first received signal and the second received signal.

According to the ultrasonic measuring method as described above, when the thickness of the coating material, such as the basis weight and coating profile of the coating material, is measured, with respect to the coated product formed by coating the substrate with the coating material, the thickness of the coating material can be easily calculated, only by obtaining the second received signal during actual measurement, without requiring a calibration curve, or the like, indicating the relationship between the attenuation factor of ultrasonic waves transmitted through the coating material and the thickness of the coating material, during the actual measurement of the thickness of the coating material.

More specifically, the basis weight of the coating material can be determined according to the following equation, using the attenuation factor of ultrasonic waves transmitted through the coating material.

$$M = A/\alpha \tag{5}$$

where M is the basis weight (g/m$^2$) of the coating material, $\alpha$ is the attenuation factor (%) of ultrasonic waves, and A is a constant.

Here, the relationship between the basis weight and the attenuation factor of ultrasonic waves will be explained, using three types of reference foils A, B, C for comparison, which have different basis weights. The attenuation factor $\alpha$ of ultrasonic waves is the relative ratio of a received signal (no-foil received signal) $S_C$ of ultrasonic waves US transmitted only through the air layer and received, with no foil placed between the first ultrasonic sensor and the second ultrasonic sensor, and a received signal (in the presence of a foil) $S_K$ of ultrasonic waves transmitted through the reference foil for comparison placed between the first ultrasonic sensor and the second ultrasonic sensor and received.

About Reference Foil A for Comparison
The basis weight $M_A$ of the reference foil A for comparison is obtained as follows, according to Eq. (5) above.

$$M_A = A/(S_{KA}/S_C) \tag{6}$$

From Eq. (6) above, the constant A is obtained as follows.

$$A = M_A \times S_{KA}/S_C \tag{7}$$

where $M_A$ is the basis weight (g/m$^2$) of the reference foil A for comparison, $S_{KA}$ is the received signal in the presence of the reference foil A for comparison, and $S_C$ is the no-foil received signal.

About Reference Foil B for Comparison
The basis weight $M_B$ of the reference foil B for comparison is obtained as follows, according to Eq. (5) above.

$$M_B = A/(S_{KB}/S_C) \tag{8}$$

From Eq. (8) above, the constant A is obtained as follows.

$$A = M_B \times S_{KB}/S_C \tag{9}$$

where $M_B$ is the basis weight (g/m$^2$) of the reference foil B for comparison, and $S_{KB}$ is the received signal in the presence of the reference foil B for comparison.

About Reference Foil C for Comparison
The basis weight $M_C$ of the reference foil C for comparison is obtained as follows, according to Eq. (5) above.

$$M_C = A/(S_{KC}/S_C) \tag{10}$$

From Eq. (10) above, the constant A is obtained as follows.

$$A = M_C \times S_{KC}/S_C \tag{11}$$

where $M_C$ is the basis weight (g/m$^2$) of the reference foil C for comparison, and $S_{KC}$ is the received signal in the presence of the reference foil C for comparison.

Since the constant A and the no-foil received signal $S_C$ are constant, as indicated in Eq. (7), Eq. (9) and Eq. (11), the following equation (Eq. (12)) is derived from Eq. (7), Eq. (9) and Eq. (11).

$$M_A \times S_{KA} = M_B \times S_{KB} = M_C \times S_{KC} = A \times S_C = \text{constant} \tag{12}$$

On the other hand, the basis weight $M_X$ of a reference foil X for comparison, of which the basis weight is unknown, is obtained as follows, according to Eq. (5) above.

$$M_X = A/(S_X/S_C) \tag{13}$$

where Mx is the basis weight (g/m$^2$) of the reference foil X for comparison, and $S_X$ is a received signal in the presence of the reference foil X for comparison.

By using Eq. (12) above, Eq. (13) is converted into the following equation (Eq. (14)).

$$M_X = A \times S_C/S_X = M_A \times S_{KA}/S_X = M_B \times S_{KB}/S_X = M_C \times S_{KC}/S_X \tag{14}$$

Since it is found from Eq. (12) that the numerator(s) of (in) Eq. (14) is (are) a constant value, the basis weight $M_X$ of the reference foil X for comparison can be determined (obtained) from the ratio (relative proportion) of the constant value obtained from Eq. (12) and (to) the received signal $S_X$ (obtained) in the presence of the reference foil X for comparison.

In the ultrasonic measuring method of the invention, prior to the actual measurement by the actual-measurement ultrasonic sensor set, the calibration Ultrasonic sensor set initially obtains the attenuation factor of ultrasonic waves transmitted through the reference foil used for calibration, in advance, as the first received signal. More specifically, in the case where the reference foil A for comparison is the reference foil used for calibration, for example, the no-foil received signal $S_C$ in the denominator of Eq. (6) is a received signal as a constant of ultrasonic waves transmitted only through the air layer and received, with no reference foil placed between the first calibration ultrasonic sensor and the second calibration ultrasonic sensor. Also, the received signal $S_{KA}$ obtained in the presence of the reference foil A for comparison, in the denominator of Eq. (6), is the first received signal itself. If the weight and area of the reference foil are determined or known in advance, the density of the reference foil can be grasped. Since the basis weight $M_A$ of the reference foil is equivalent to the density of the reference foil, the basis weight $M_A$ is obtained from the weight and area of the reference foil. Accordingly, the numerator in the above-indicated Eq. (14): $M_X = M_A \times S_{KA}/S_X$ can be calculated from the predetermined weight and area of the reference foil, and the first received signal.

Subsequently, for actual measurement of the thickness of the coating material, the coated product is placed between the first ultrasonic sensor and the second ultrasonic sensor of the actual-measurement ultrasonic sensor set, and ultrasonic waves sent from the first ultrasonic sensor are transmitted through the coated product, so that the second received signal of ultrasonic waves received by the second ultrasonic sensor is obtained. As described above, the received signal $S_X$ as the denominator of Eq. (14) is the thus obtained second received signal itself, namely, the received signal of ultrasonic waves propagated through the reference foil X for comparison, whose basis weight is unknown, i.e., through the coated product to be measured, and received. Thus, if the basis weight $M_A$ of the reference foil for calibration, and the first received signal are obtained in advance, prior to the actual measurement by the actual-measurement ultrasonic sensor set, the thickness of the coating material can be easily calculated according to Eq. (14), only by obtaining the second received signal, during the actual measurement of the thickness of the coating material.

In the ultrasonic measuring method as described above, a plurality of first sample received signals corresponding to a plurality of regions of the reference foil may be obtained as received signals of ultrasonic waves sent from the first calibration ultrasonic sensor, transmitted through the reference foil, and received by the second calibration ultrasonic sensor, and the first received signal may be computed based on the above-indicated plurality of first sample received signals.

According to the ultrasonic measuring method as described above, when the calibration ultrasonic sensor set performs calibration, using the reference foil, the first received signal having improved reliability and the optimum magnitude is obtained, even in the case where there are variations in the attenuation factors (first sample received signals) of ultrasonic waves transmitted through the reference foil, from region to region in the reference foil.

Strictly speaking, if the calibration ultrasonic sensor set allows ultrasonic waves to be transmitted through different regions of one reference foil placed between the first calibration ultrasonic sensor and the second calibration ultrasonic sensor, variations may arise in the attenuation factors (first sample received signals) of ultrasonic waves, as in the case where $S_{KA} \neq S_{KB} \neq S_C$ or $S_{KA} \approx S_{KB} \neq S_C$, in the above-indicated Eq. (6), Eq. (8) and Eq. (10), for example. If the attenuation factor of ultrasonic waves varies depending on the region of the reference foil through which the ultrasonic waves are transmitted, when the calibration ultrasonic sensor set performs calibration, the reliability of the first received signal is reduced, and the measurement condition values to be reflected by the actual-measurement ultrasonic sensor set cannot be obtained with high accuracy. On the other hand, in the ultrasonic measuring method of the invention, the first sample received signals are obtained with respect to the plurality of regions of the reference foil, and the first received signal (the attenuation factor of ultrasonic waves transmitted through the reference foil) is obtained by computation, such as a least square method, based on the obtained plurality of first sample received signals. Therefore, the first received signal has improved reliability and the optimum magnitude. In particular, it is preferable to correct or update respective pieces of data as measurement results of the temperature, density and air pressure of the air layer through which ultrasonic waves are propagated between the first calibration ultrasonic sensor and the second calibration ultrasonic sensor, each time the thickness (or basis weight) of the coating material is measured and calculated by the actual-measurement ultrasonic sensor set. If the first receive signal is obtained in a condition where the above-indicated respective pieces of data are corrected or updated each time the basis weight of the coating material is calculated, the reliability of the first received signal is improved, and its accuracy is kept at a high level.

The attenuation factor of ultrasonic waves transmitted through the reference foil is obtained with improved reliability and high accuracy; therefore, when the thickness (or basis weight) of the coating material is measured and calculated by the actual-measurement ultrasonic sensor set, the first received signal obtained with high accuracy, as well as the second received signal, is reflected by measurement condition values of the actual-measurement ultrasonic sensor set, and the thickness (or basis weight) of the coating material can be calculated with further improved accuracy.

In the ultrasonic measuring method as described above, the actual-measurement ultrasonic sensor set may be moved to a position at which the reference foil is placed, and may obtain a third received signal representing ultrasonic waves that are sent from the first ultrasonic sensor, transmitted through the reference foil, and received by the second ultrasonic sensor.

According to the ultrasonic measuring method as described above, when there is a machine difference between the first calibration ultrasonic sensor and second calibration ultrasonic sensor of the calibration ultrasonic sensor set, and the first ultrasonic sensor and second ultrasonic sensor of the actual-measurement ultrasonic sensor set, the machine difference between the calibration ultrasonic sensor set and the actual-measurement ultrasonic sensor set can be grasped from the relative ratio of the first received signal and the third received signal. Accordingly, if the actual-measurement ultrasonic sensor set calculates the thickness of the coating material in view of the machine difference from the calibration ultrasonic sensor set, based on the first received signal and the third received signal, error factors due to the machine difference between the calibration ultrasonic sensor set and the actual-measurement ultrasonic sensor set can be excluded or eliminated, and the thickness of the coating material can be calculated with high accuracy.

In the ultrasonic measuring method as described above, a plurality of third sample received signals corresponding to a plurality of regions of the reference foil may be obtained as received signals of ultrasonic waves sent from the first ultrasonic sensor, transmitted through the reference foil, and received by the second ultrasonic sensor, and the third received signal may be computed based on the above-indicated plurality of third sample received signals.

According to the ultrasonic measuring method as described above, when machine differences between the calibration ultrasonic sensor set and the actual-measurement ultrasonic sensor set are determined, using the reference foil, the third received signal having improved reliability and the optimum magnitude is obtained, even in the case where there are variations in the attenuation factors (third sample received signals) of ultrasonic waves transmitted through the reference foil, from region to region in the reference foil. Since the third received signal (the attenuation factor of ultrasonic waves transmitted through the reference foil) is obtained by computation, such as a least square method, based on the obtained plurality of third sample received signals, the third received signal has improved reliability and the optimum magnitude even when there are variations in the plurality of third sample received signals.

In particular, it is preferable, in relation to the calibration ultrasonic sensor set, that the first received signal is computed based on a plurality of first sample received signals obtained from a plurality of regions of the reference foil. If machine differences between the calibration ultrasonic sensor set and the actual-measurement ultrasonic sensor set are determined from the thus obtained first received signal and third received signal, a result of determination on the machine differences can be obtained with further improved accuracy.

In the ultrasonic measuring method as described above, the first calibration ultrasonic sensor and the second calibration ultrasonic sensor, and the first ultrasonic sensor and the second ultrasonic sensor, may send and receive ultrasonic waves in synchronization with each other.

According to the ultrasonic measuring method as described above, the calibration ultrasonic sensor set and the actual-measurement ultrasonic sensor set can be exposed to an environment having the same atmosphere temperature with no time difference, and the sound velocity, density, and acoustic impedance in the air layer can be made substantially equal in the calibration ultrasonic sensor set and the actual-measurement ultrasonic sensor set. With this arrangement, the ultrasonic waves transmitted between the first calibration ultrasonic sensor and the second calibration ultrasonic sensor of the calibration ultrasonic sensor set, and the ultrasonic waves transmitted between the first ultrasonic sensor and the second ultrasonic sensor of the actual-measurement ultrasonic sensor set are transmitted through the air layers, under substantially the same conditions. Accordingly, the actual-measurement ultrasonic sensor set acquires measurement condition values from the calibration ultrasonic sensor set, as highly accurate, correction values from which error factors due to the atmosphere temperature and self-heating are excluded, under the same conditions as the calibration ultrasonic sensor set, so that the thickness of the coating material can be calculated with high accuracy in a stable condition.

According to another aspect of the invention, an ultrasonic measuring system is provided which includes at least one actual-measurement ultrasonic sensor set each comprising a pair of first ultrasonic sensor and second ultrasonic sensor, the first ultrasonic sensor being placed on one side of a coated product formed by applying a coating material by coating to one surface or both surfaces of a substrate made of metal and wound in the form of a roll, as viewed in a thickness direction of the coated product, via an air layer, the second ultrasonic sensor being placed on the other side of the coated product, via an air layer, each of the at least one actual-measurement ultrasonic sensor set being operable to measure a thickness of the coating material by transmitting ultrasonic waves between the first ultrasonic sensor and the second ultrasonic sensor, and a calibration ultrasonic sensor set comprising a pair of first calibration ultrasonic sensor and second calibration ultrasonic sensor, aside from the first ultrasonic sensor and the second ultrasonic sensor. In the ultrasonic measuring system, the actual-measurement ultrasonic sensor set sends and receives ultrasonic waves, based on a measurement condition value obtained through calibration by the calibration ultrasonic sensor set, during actual measurement of the thickness of the coating material.

According to the ultrasonic measuring system as described above, when the thickness of the coating material, such as the basis weight and coating profile of the coating material, is measured on the production line on which the electrode (coated product) is produced by coating the metal foil (substrate) with the electrode paste (coating material), in the battery production process, error factors of the measurement accuracy due to self-heating of the ultrasonic sensors and changes in the temperature of the air layer are excluded or eliminated, during the actual measurement, and the thickness of the coating material can be measured with high accuracy.

With the first and second ultrasonic sensors and the first and second calibration ultrasonic sensors operating in the same timing, even if the first and second ultrasonic sensors are self-heated with a lapse of the operating time, the first and second calibration ultrasonic sensors are also self-heated in the same fashion as the first and second ultrasonic sensors. In this case, there is almost no difference between the temperatures of the self-heated first and second ultrasonic sensors and the temperatures of the self-heated first and second calibration ultrasonic sensors. Therefore, even if the wavelength of ultrasonic waves received in the calibration ultrasonic sensor set changes due to self-heating, the wavelength of ultrasonic waves received in the actual-measurement ultrasonic sensor set also changes in the same manner as that of the calibration ultrasonic sensor set. Thus, there arises almost no difference between the wavelength of the actual-measurement ultrasonic sensor set and the wavelength of the calibration ultrasonic sensor set, and the thickness of the coating material can be measured, assuring high measurement accuracy, even if the first and second calibration ultrasonic sensors of the calibration ultrasonic sensor set and the first and second ultrasonic sensors of the actual-measurement ultrasonic sensor set are both self-heated.

Thus, in the ultrasonic measuring system of the invention, error factors of the measurement accuracy due to self-heating of the ultrasonic sensors and changes in the temperature of the air layer can be excluded or eliminated, so that the thickness (such as the basis weight) of the coating material applied by coating to the coated product produced on the production line can be advantageously measured on the production line with high accuracy.

In the ultrasonic measuring system of the invention, the production line for producing the coated product need not be stopped, and the actual-measurement ultrasonic sensor set can acquire measurement condition values obtained through calibration by the calibration ultrasonic sensor set, during operation of the line. Therefore, an extra or additional step for correcting measurement conditions of the actual-measurement ultrasonic sensor set is not required, and the cost for production of the coated product will not be increased. Also, the ultrasonic measuring system of the invention is installed on the production line at a low cost, and can be easily incorporated into the production line for producing the coated product, no matter whether the system is newly installed or has already been installed.

In the ultrasonic measuring system as described above, flat-type ultrasonic sensors that permit propagation of unfocused ultrasonic waves may be used as the first calibration ultrasonic sensor and the second calibration ultrasonic sensor of the calibration ultrasonic sensor set, and flat-type ultrasonic sensors that permit propagation of unfocused ultrasonic waves may be used as the first ultrasonic sensor and the second ultrasonic sensor of the actual-measurement ultrasonic sensor set.

When the thickness of the coating material, such as the basis weight and coating profile of the coating material, is measured on the production line on which the electrode (coated product) is produced by coating the metal foil (substrate) with the electrode paste (coating material), in the battery production process, for example, a wide area of the coated product is irradiated with ultrasonic waves sent from the first ultrasonic sensor so that the ultrasonic waves are transmitted through the substrate and the coating material of the coated product, and the second ultrasonic sensor can receive the ultrasonic waves (transmitted waves) transmitted through wide ranges of the substrate and the coating material. Since the received signal representing the transmitted waves received by the second ultrasonic sensor can be obtained from a wide range of the coated product, as the received signal for determining the thickness of the coating material, the thickness of the coating material over a wide range of the coated product can be detected. Accordingly, variations in the thickness of the coating material within the measurement range can be grasped with improved accuracy, and the overall thickness of the coating material, such as the basis weight of the coating material, within a given range of the coated product can be measured with high reliability.

All of the first calibration ultrasonic sensor and second calibration ultrasonic sensor of the calibration ultrasonic sensor set, and the first ultrasonic sensor and second ultrasonic sensor of the actual-measurement ultrasonic sensor set are flat-type ultrasonic sensors. Therefore, no differences in characteristics due to differences in the forms of the ultrasonic vibration surfaces of the ultrasonic sensors appear between the calibration ultrasonic sensor set and the actual-measurement ultrasonic sensor set, and the measurement condition values obtained through calibration by the calibration ultrasonic sensor set can be appropriately and accurately fed back to the actual-measurement ultrasonic sensor set.

In the ultrasonic measuring system as described above, a control unit may be provided for controlling sending and receiving of ultrasonic waves and measurement conditions, in the calibration ultrasonic sensor set and the actual-measurement ultrasonic sensor set, and the control unit may feed back the measurement condition value obtained by the calibration ultrasonic sensor set, to the actual-measurement ultrasonic sensor set.

According to the ultrasonic measuring system as described above, the actual-measurement ultrasonic sensor set can constantly acquire the latest measurement condition values resulting from calibration by the calibration ultrasonic sensor set, in accordance with changes in the measurement environment, in real time during actual measurement of the thickness of the coating material, and the thickness of the coating material can be measured with high accuracy.

In the ultrasonic measuring method of the related art in which calibration is not carried out at the same time as the actual ultrasonic measurement, there is a time difference between calibration performed earlier and calibration performed later, and increases in the temperature of the ultrasonic sensors due to self-heating, and changes in the measurement environments, such as the atmosphere temperature and the density of the air layer, often take place within the time. Even if the thickness of the coating material is measured with the ultrasonic sensors while the measurement environments are changing, the measurement results vary due to changes in the measurement environments, resulting in measurement values having low or no reliability. On the other hand, the ultrasonic measuring system of the invention can measure the thickness of the coating material by constantly adopting the latest measurement condition values, in accordance with changes in the measurement environments; therefore, the calculation results of the thickness of the coating material provide measurement values having high accuracy and high reliability.

In the ultrasonic measuring system as described above, a reference foil used for calibration may be placed along with the coated product, and the calibration ultrasonic sensor set may be mounted so as to be movable at least within a range between a first position at which the reference foil is placed, and a second position at which only an air layer is present between the first calibration ultrasonic sensor and the second calibration ultrasonic sensor.

According to the ultrasonic measuring system as described above, the calibration ultrasonic sensor set moves between the first position and the second position, so that the received signal $S_K$ (in the presence of the foil) of ultrasonic waves transmitted through the reference foil placed between the first calibration ultrasonic sensor and the second calibration ultrasonic sensor and received can be obtained at the first position, and the no-foil received signal $S_C$ can be obtained at the second position, as described above. With this arrangement, even if changes in the measurement environments, such as the temperature of the atmosphere in which calibration is performed, and the density of the air layer, and/or increases in the temperatures of the ultrasonic sensors due to self-heating, take place, the calibration ultrasonic sensor set moves between the first position and the second position, so as to constantly obtain the received signal $S_K$ in the presence of the foil and the no-foil received signal $S_C$, which are required for obtaining the attenuation factor of ultrasonic waves transmitted through the reference foil. Thus, when the thickness of the coating material of the coated product is actually measured, the optimum attenuation factor can be obtained in accordance with changes in the measurement environments.

The ultrasonic measuring system as described above may further include a holding member that holds the reference foil, and a drive unit that operates the holding member, and stops operation thereof. The reference foil held by the holding member may be positioned by the drive unit so as to be movable relative to the first ultrasonic sensor and the second ultrasonic sensor, within a range in which the reference foil intersects with an imaginary line that connects the center of the first ultrasonic sensor with the center of the second ultrasonic sensor opposed to the first ultrasonic sensor, or may be positioned by the drive unit so as to be movable relative to the first calibration ultrasonic sensor and the second calibration ultrasonic sensor, within a range in which the reference foil intersects with an imaginary line that connects the center of the first calibration ultrasonic sensor with the center of the second calibration ultrasonic sensor opposed to the first calibration ultrasonic sensor.

According to the ultrasonic measuring system as described above, when the calibration ultrasonic sensor set performs calibration, using a single reference foil placed between the first calibration ultrasonic sensor and the second calibration ultrasonic sensor, ultrasonic waves propagated between the first calibration ultrasonic sensor and the second calibration ultrasonic sensor are transmitted through a plurality of regions of the reference foil. Thus, the attenuation factor of the transmitted ultrasonic waves can be calculated for each of the regions of the single reference foil through which the ultrasonic waves are transmitted. Also, when machine differences between the calibration ultrasonic sensor set and the actual-measurement ultrasonic sensor set are determined, using the reference foil, ultrasonic waves propagated between the first ultrasonic sensor and the second ultrasonic sensor are transmitted through a plurality of regions of the reference foil. Thus, the attenuation factor of the transmitted ultrasonic waves can be calculated for each of the regions of the single reference foil through which the ultrasonic waves are transmitted. Consequently, calibration performed by the calibration ultrasonic sensor set, and determination of machine differences between the first calibration ultrasonic sensor and second calibration ultrasonic sensor, and the first ultrasonic sensor and second ultrasonic sensor, can be accomplished with improved accuracy.

The ultrasonic measuring system as described above may further include a positioning device that detects positions on the holding member that is in operation, at which positions the imaginary line intersects with predetermined regions of the reference foil. The "predetermined regions" mean regions of the reference foil through which ultrasonic waves propagated between the first ultrasonic sensor and the second ultrasonic sensor are transmitted, at desired positions within the reference foil, or regions of the reference foil through which ultrasonic waves propagated between the first calibration ultrasonic sensor and the second calibration ultrasonic sensor are transmitted, at desired positions within the reference foil.

According to the ultrasonic measuring system as described above, when calibration is repeatedly carried out a plurality of times, using the reference foil placed between the first calibration ultrasonic sensor and the second calibration ultrasonic sensor, the positioning device can set the predetermined regions with which the imaginary line intersects within the reference foil, to the same positions, for each cycle of calibration. Consequently, highly accurate calibration can be achieved. Also, when machine differences between the calibration ultrasonic sensor set and the actual-measurement ultrasonic sensor set are repeatedly determined a plurality of times, the positioning device can set the predetermined regions with which the imaginary line intersects within the reference foil, to the same positions, for each cycle of determination of machine differences. Consequently, research on machine differences between the calibration ultrasonic sensor set and the actual-measurement ultrasonic sensor set can be accomplished with improved reliability.

In the ultrasonic measuring system as described above, the actual-measurement ultrasonic sensor set may be mounted so as to be movable at least within a range between the first position, and a third position at which the coated product is placed.

According to the ultrasonic measuring system as described above, each time the actual-measurement ultrasonic sensor set moves between the first position and the third position, the latest machine difference between the actual-measurement ultrasonic sensor set and the calibration ultrasonic sensor set that performs calibration using the reference foil that is "true" can be taken into or fed to the actual-measurement ultrasonic sensor set. Therefore, even if changes in the measurement environments, such as the temperature of the atmosphere in which the thickness of the coating material is measured, and the density of the air layer, and/or increases in the temperatures of the ultrasonic sensors due to self-heating, take place, error factors due to the machine difference from the calibration ultrasonic sensor set can be excluded with increased reliability.

Also, in the ultrasonic measuring system as described above, the substrate sound in the form of a roll has a large length, and the reference foil and the coated product may be arranged side by side in a width direction of the substrate, which is perpendicular to a longitudinal direction parallel to long sides of the substrate and a thickness direction of the substrate, such that the calibration ultrasonic sensor set and the actual-measurement ultrasonic sensor may be arranged to move in a direction parallel to the width direction of the substrate.

According to the ultrasonic measuring system as described above, the calibration ultrasonic sensor set and the actual-measurement ultrasonic sensor set are arranged to move on the same slide shafts, such that the calibration ultrasonic sensor set and the actual-measurement ultrasonic sensor set move in synchronization with each other, relative to the slide shafts. With this arrangement, the calibration ultrasonic sensor set moves between the first position and the second position at the same time that the actual-measurement ultrasonic sensor set moves between the first position and the third position. Thus, the calibration ultrasonic sensor set and the actual-measurement ultrasonic sensor set are both able to change setting of measurement conditions according to measurement environments, such as the atmosphere temperature and the density of the air layer, with no loss of time and high efficiency.

Even in the case where the calibration ultrasonic sensor set and the actual-measurement ultrasonic sensor set do not particularly move in synchronization with each other on the slid shafts, but are arranged to move independently of each other, the movement of the actual-measurement ultrasonic sensor set is not restricted by the amount of movement of the calibration ultrasonic sensor set on the slide shafts, and therefore, the actual-measurement ultrasonic sensor set can measure the thickness of the coating material with an increased degree of freedom.

Also, in the ultrasonic measuring system as described above, each of the first calibration ultrasonic sensor and the second calibration ultrasonic sensor of the calibration ultrasonic sensor set may be provided with a cylindrical, calibration sensor cover that surrounds an air layer between an ultrasonic vibration surface and the reference foil.

According to the ultrasonic measuring system as described above, during execution of calibration, error factors due to an influence of convection (flow of air) in the air layer, including, for example, changes in the density, changes in the temperature, changes in the acoustic impedance, the directionality of transmitted ultrasonic waves, and interference with sound waves transmitted as noise from the outside, in the air layer between the ultrasonic vibration surface and the reference foil, are excluded or eliminated, and the measurement condition values as reference values can be obtained with improved accuracy.

In the ultrasonic measuring system as described above, each of the first ultrasonic sensor and the second ultrasonic sensor of the actual-measurement ultrasonic sensor set may be provided with a cylindrical actual-measurement sensor cover that surrounds an air layer between an ultrasonic vibration surface and the coated product.

According to the ultrasonic measuring system as described above, during actual measurement of the thickness of the coating material, error factors due to an influence of convection (air flow) in the air layer, including, for example, changes in the density, changes in the temperature, changes in the acoustic impedance, the directionality of transmitted ultrasonic waves, and interference with sound waves transmitted as noise from the outside, in the air layer between the ultrasonic vibration surface and the coated product, are excluded or eliminated, and the thickness of the coating material can be measured with improved accuracy.

In the ultrasonic measuring system as described above, each of the calibration sensor cover and the actual-measurement sensor cover may have a dual structure comprising an inner cylindrical cover, and an outer cylindrical cover located radially outwardly of the inner cylindrical cover, and the outer cylindrical cover may be formed to be shorter than the inner cylindrical cover, as measured in a direction parallel to a thickness direction of the substrate, so that the outer cylindrical cover is spaced by a larger difference from the reference foil or the coated product, than the inner cylindrical cover.

According to the ultrasonic measuring system as described above, even if air that flows outside the calibration sensor cover hits against the calibration sensor cover in the vicinity of the surface of the reference foil, the flow of the air is changed by the inner cylindrical cover, and the air flows between the outer cylindrical cover and the inner cylindrical cover, so that air turbulence is less likely or unlikely to occur in the vicinity of the surface of the reference foil. Therefore, even if there is a slight clearance between the inner cylindrical cover and the reference foil, air that flows through the small clearance is hardly influenced by the turbulence, and the air layer between the ultrasonic vibration surface and the reference foil can be kept in a stable condition.

Also, even if air that flows outside the actual-measurement sensor cover hits against the actual-measurement sensor cover in the vicinity of the surface of the coated product, the flow of the air is changed by the inner cylindrical cover, and the air flows between the outer cylindrical cover and the inner cylindrical cover, so that air turbulence is less likely or unlikely to occur in the vicinity of the surface of the coated product. Therefore, even if there is a slight clearance between the inner cylindrical cover and the coated product, air that flows through the small clearance is hardly influenced by the turbulence, and the air layer between the ultrasonic vibration surface and the coated product can be kept in a stable condition.

In the ultrasonic measuring system as described above, the substrate may be a metal foil used in an electrode of a battery as the coated product, and the coating material may be an electrode paste applied by coating to the metal foil.

According to the ultrasonic measuring system as described above, in the battery production process, quality check regarding the basis weight of the electrode paste can be uniformly conducted over a wide range of the electrode, on the production line for producing the electrode by coating the metal foil with the electrode paste, during operation of the line. Furthermore, the quality check can be performed on all of the electrodes produced on the line, so that high-quality, high-performance batteries can be provided.

BRIEF DESCRIPTION OF THE DRAWINGS

The features, advantages, and technical and industrial significance of this invention will be described in the following detailed description of example embodiments of the invention with reference to the accompanying drawings, in which like numerals denote like elements, and wherein:

FIG. 19 is a schematic view showing the manner of obtaining first sample received signals and third sample received signals by transmitting ultrasonic waves through five regions of a reference foil, in the ultrasonic measuring method according to the second embodiment;

FIG. 27 is a graph indicating the relationship between the wavelength of ultrasonic waves received in the system of the related art, and the received power.

DETAILED DESCRIPTION OF EMBODIMENTS

Ultrasonic measuring methods and ultrasonic measuring systems according to first and second embodiments of the invention will be described in detail with reference to the drawings.

Figure 1:
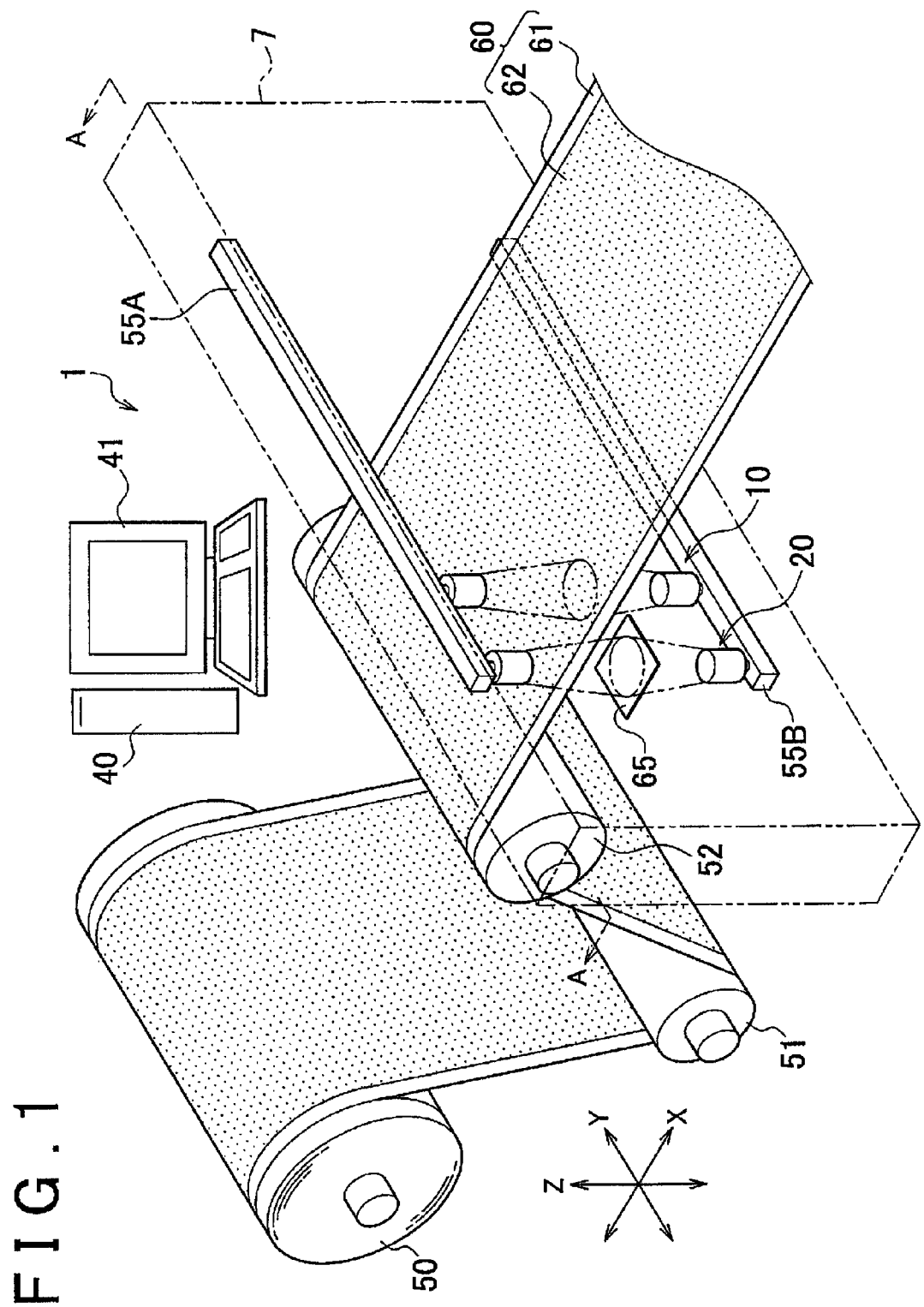
FIG. 1 is a perspective view schematically showing an ultrasonic measuring system according to a first embodiment of the invention.
Figure 7:
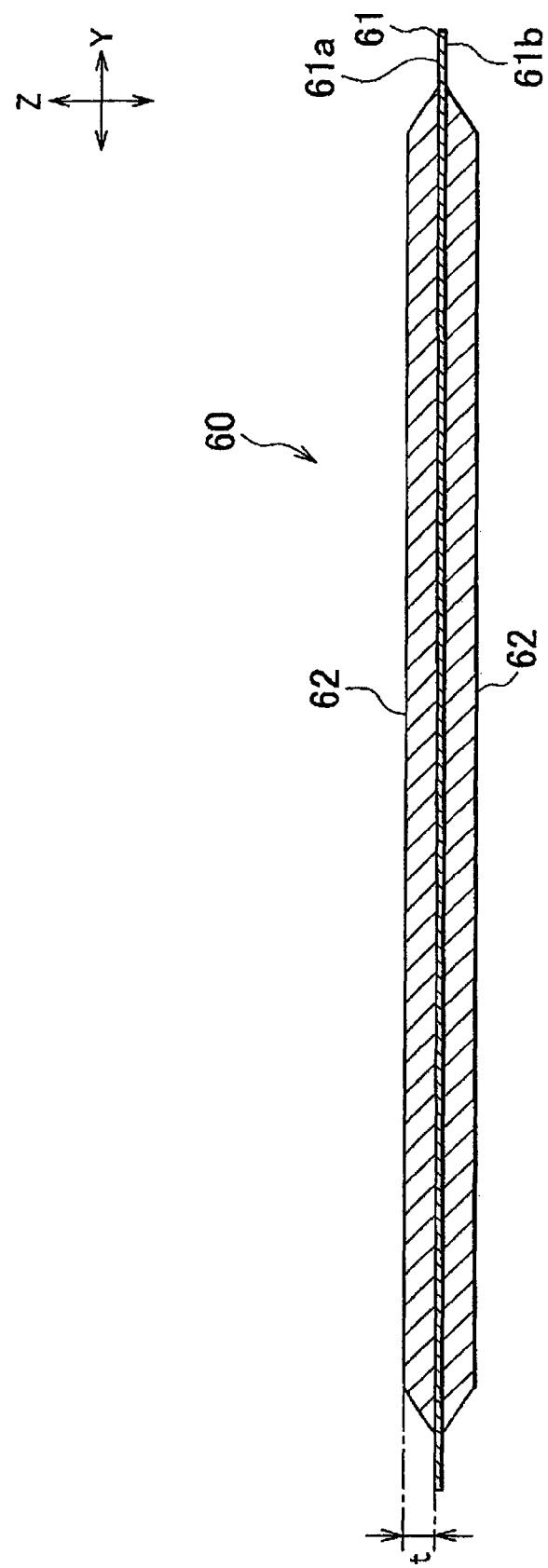
FIG. 7 is a cross-sectional view of an electrode as seen in the direction of arrows A-A in FIG. 1.

FIG. 1 is perspective view schematically showing an ultrasonic measuring system according to a first embodiment of the invention. FIG. 7 is a cross-sectional view of an electrode as viewed in a direction of arrows A-A in FIG. 1. In FIG. 1 showing the first embodiment, X-axis direction denotes a direction in which the long sides of a metal foil 61 extend, or direction parallel to the long sides of the metal foil 61, and Z-axis direction denotes a direction of the thickness of an electrode 60 (the metal foil 61 and electrode paste 62), or direction parallel to the thickness of the electrode 60. Also, Y-axis direction denotes a direction in which the short sides of the metal foil 61 extend (the direction of the width of the metal foil 61), or the width direction of the ultrasonic measuring system 1 parallel to the width direction of the metal foil 61. The Y-axis direction is perpendicular to the X-axis direction and the Z-axis direction. These notations used in FIG. 1 also apply to FIG. 2 and subsequent figures.

The ultrasonic measuring system according to the first embodiment is installed as an in-line system on an electrode production line for producing the electrode 60 (coated product) by coating the metal foil 61 (substrate) with the electrode paste 62 (coating material), in a battery production process. The ultrasonic measuring system is installed for the purpose of performing quality check or inspection, such as measurement of the basis weight (which means the weight per unit area of the coating material), etc. of the electrode paste 62 that is dried. The ultrasonic measuring method according to the first embodiment is a method for performing quality check on the basis weight of the electrode paste 62, using the above-mentioned ultrasonic measuring system 1.

Initially, the electrode will be briefly described. In the first embodiment, the substrate is the metal foil 61 used for production of electrodes of batteries as coated products, and the coating material is the electrode paste 62 applied by coating to the metal foil 61, as described above. In the first embodiment, in particular, the electrode paste 62 is applied by coating to opposite surfaces (one surface 61a and the other surface 61b) of the metal foil 61. For example, the electrode 60 is used in a secondary battery as a power supply of an electric vehicle, a hybrid vehicle, or the like. As shown in FIG. 7, the electrode 60 is formed by coating the opposite surfaces 61a, 61b of the metal foil 61 made of a metal, such as Au or Cu, with the electrode paste 62. More specifically, the electrode paste 62 is applied by coating to portions of the opposite surfaces 61a, 61b of the metal foil 61 other than their opposite end portions as viewed in the Y-axis direction.

The metal foil 61 having a long length has a thickness of about 20 μm, and is wound in the form of a roll on a winding roller (not shown) of the electrode production line. On the electrode production line, the electrode paste 62 applied by coating to the metal foil 61 is pressed against the metal foil 61 so that the thickness t of the electrode paste 62 becomes equal to about 40-50 μm, and then dried; thereafter, the electrode 60 in the form of a roll is transported by a feed conveyor 52, via a winding roller 50 and a feed roller 51, to be brought into a horizontal condition. The electrode 60 thus successively and continuously produced is delivered by the feed conveyor 52, in a horizontal form, to the next process step, such as cutting of the electrode 60. Although not shown in FIG. 1, a leading end portion (as viewed in the X-axis direction) of the electrode 60 produced on the electrode production line, at which the feeding of the electrode 60 starts, and a rear end portion thereof at which the feeding ends, consist solely of the metal foil 61. Namely, the electrode paste 62 is not applied by coating to the opposite surfaces 61a, 61b of the metal foil 61 in the above-indicated leading end portion and read end portion of the electrode 60.

Figure 2:
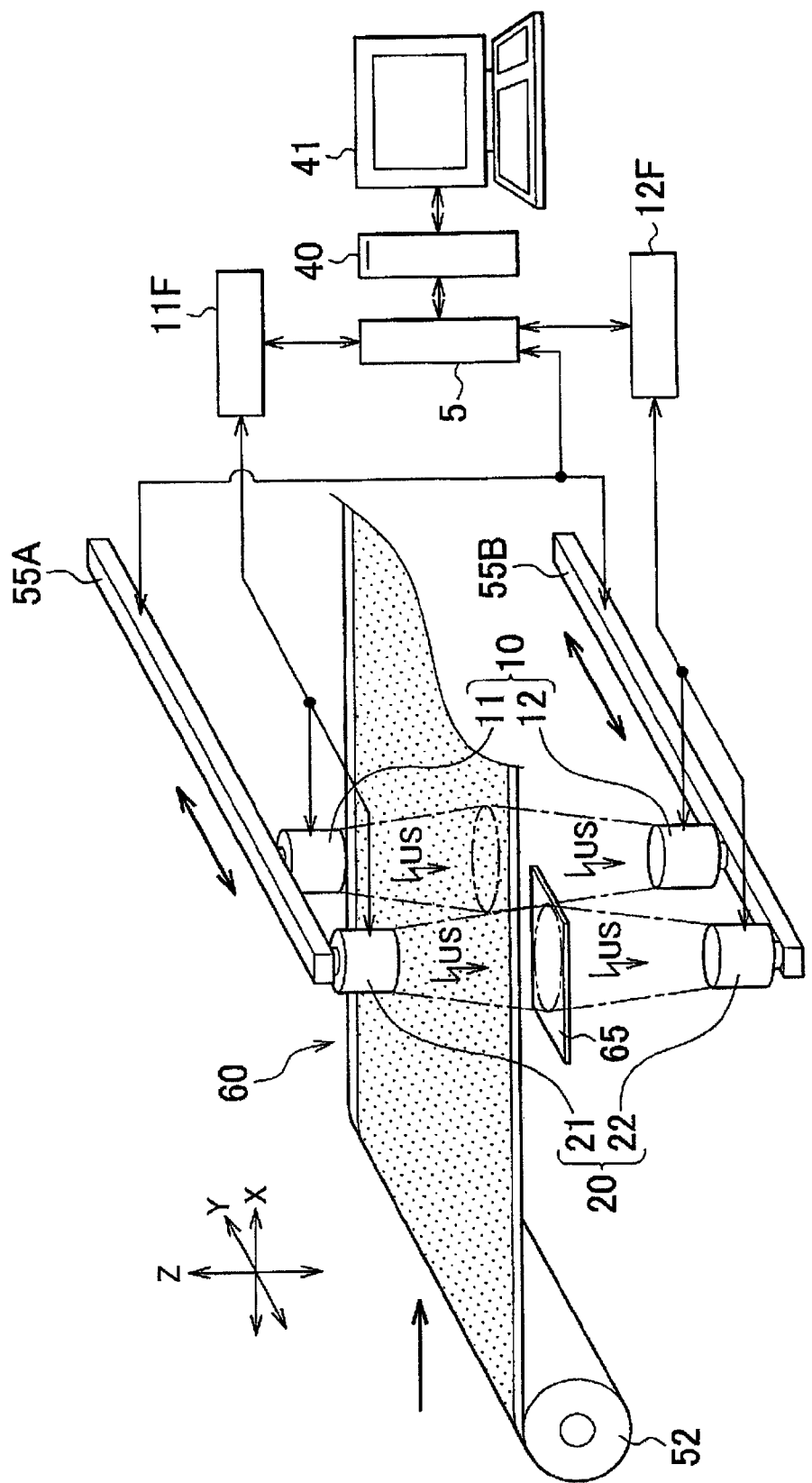
FIG. 2 is a schematic view useful for explaining the construction of the ultrasonic measuring system according to the first embodiment of FIG. 1.
Figure 3:
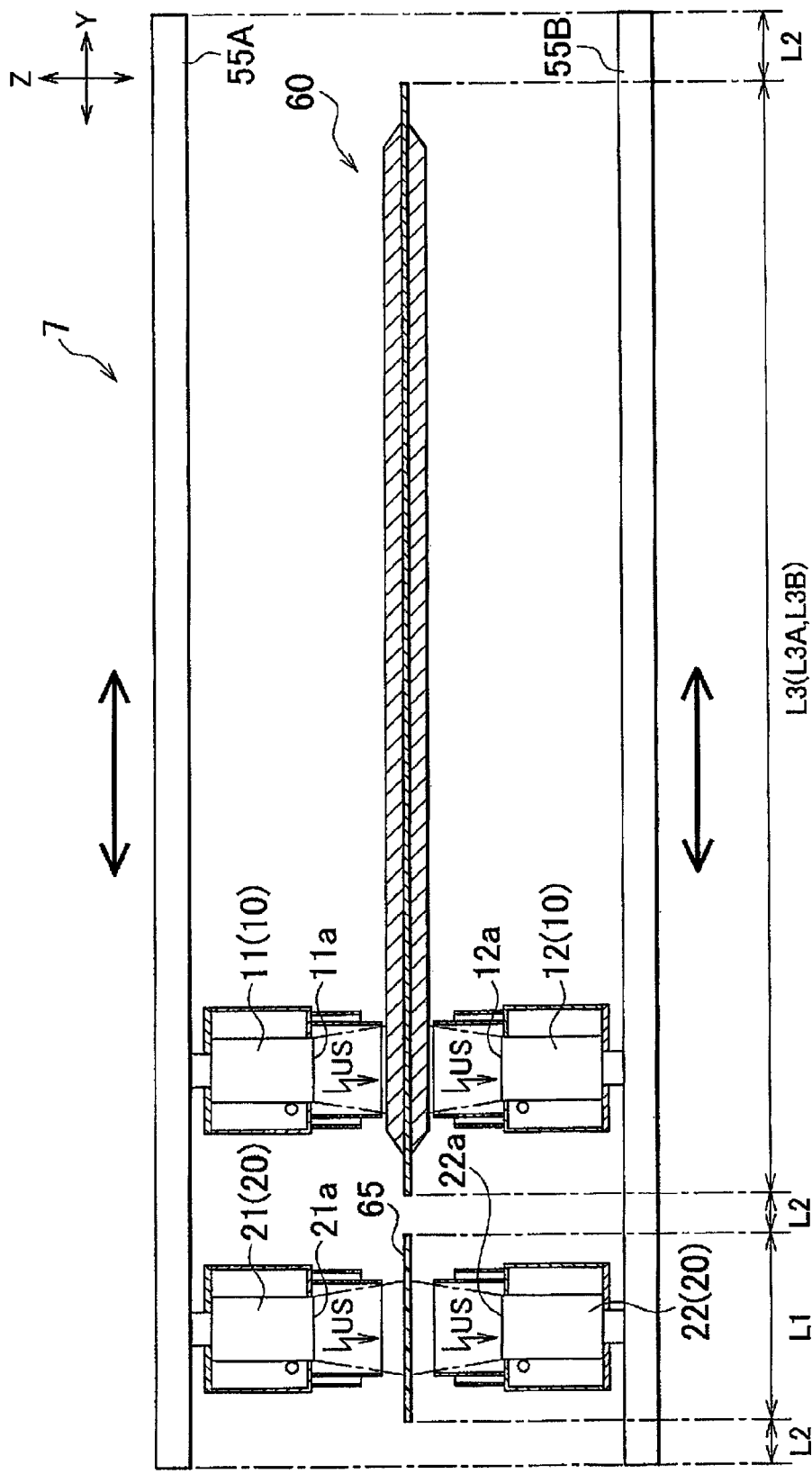
FIG. 3 is a cross-sectional view as seen in a direction of arrows A-A in FIG. 1, showing a principal portion of the ultrasonic measuring system of FIG. 1.

Next, the ultrasonic measuring system will be described with reference to FIG. 1 through FIG. 4. FIG. 2 is a schematic view useful for explaining the construction of the ultrasonic measuring system according to the first embodiment of the invention. FIG. 3 is a cross-sectional view as seen in the direction of arrows A-A in FIG. 1, showing a principal portion of the system. As shown in FIG. 1 and FIG. 2, the ultrasonic measuring system 1 has a measuring unit 7, an ultrasonic measurement control unit 5 (control means), a thickness computing unit 40, a monitor 41, and so forth. As shown in FIG. 1, the ultrasonic measuring system 1 is installed at a position where the electrode 60 is fed by the feed conveyor 52, into a horizontal form, upstream of the position where the electrode 60 is delivered to the next process step; such as cutting of the electrode 60. In the first embodiment, in particular, the measuring unit 7 for calculating the basis weight of the electrode paste 62 is disposed at a position apart from the feed conveyor 52 by about 200 mm, as measured in the X-axis direction.

The measuring unit 7 is located apart from the feed conveyor 52 for the following reason. The feed conveyor 52 provides a point of support or pivot point about which the electrode 60 in the form of a roll is delivered into a horizontal form, and external vibrations, such as vibrations of the feed conveyor 52, may occur as an external factor. As will be described in detail later, the frequency of the external vibrations is close to the frequency of ultrasonic waves generated by first and second ultrasonic sensors 11, 12, etc. used in the measuring unit 7 for measuring the thickness of the electrode 60, and the external vibrations become an obstructive factor in the form of noise when the basis weight of the electrode paste 62 is calculated. In order to remove the external factor, the measuring unit 7 needs to be spaced by some distance from the feed conveyor 52.

Next, the measuring unit 7 will be described. In the ultrasonic measuring system 1, the measuring unit 7 has a pair of ultrasonic sensors, i.e., a first ultrasonic sensor 11 and a second ultrasonic sensor 12. In the ultrasonic measuring system 1, the first ultrasonic sensor 11 is placed, via an air layer AR, on one side (upper side in FIG. 1) of the electrode 60 as viewed in the thickness direction Z, which electrode 60 is formed by coating the opposite surfaces 61a, 61b of the metal foil 61 wound in the form of a roll, with the electrode paste 62, and the second ultrasonic sensor 12 is placed, via an air layer AR, on the other side (lower side in FIG. 1) of the electrode 60. The measuring unit 7 has at least one set of ultrasonic sensors 10 for actual measurement, i.e., the first ultrasonic sensor 11 and the second ultrasonic sensor 12, for measuring the basis weight of the electrode paste 62, and a set of ultrasonic sensors 20 for calibration, i.e., a pair of first calibration ultrasonic sensor 21 and second calibration ultrasonic sensor 22, aside from the first ultrasonic sensor 11 and the second ultrasonic sensor 12. In the ultrasonic measuring system 1 of the first embodiment, only one actual-measurement ultrasonic sensor set 10 is illustrated in FIG. 1 and other figures, for the sake of simplicity in explanation.

The actual-measurement ultrasonic sensor set 10 calculates the thickness, or the basis weight, of the electrode paste 62 (coating material), by transmitting and receiving ultrasonic waves US between the first ultrasonic sensor 11 and the second ultrasonic sensor 12, based on measurement condition values obtained through calibration by the calibration ultrasonic sensor set 20, during actual measurement of the basis weight of the electrode paste 62. A reference foil 65 is used in the calibration performed by the calibration ultrasonic sensor set 20. In the measurement unit 7, the reference foil 65 is placed along with the electrode 60, such that the reference foil 65 and the electrode 60 are arranged side by side in the width direction (Y-axis direction) of the ultrasonic measuring system 1, at the same height or elevation (in the Z-axis direction).

The reference foil 65 is formed of a material that does not undergo oxidation and weight changes with the passage of time, and has substantially the same thickness and density as the electrode 60 of which the thickness is to be measured by the actual-measurement ultrasonic sensor set 10. For example, the reference foil 65 is formed from a PET (polyethylene terephthalate) film, or other polymer film. Also, the reference foil 65 is formed in a given shape having an area that is larger than an irradiation range, or transmission range, of ultrasonic waves US emitted or transmitted by the first and second ultrasonic sensors 11, 12 or the first and second calibration ultrasonic sensors 21, 22.

Next, the first and second ultrasonic sensors 11, 12 of the actual-measurement ultrasonic sensor set 10 will be described in more detail. The first ultrasonic sensor 11 is a flat-type transmitting sensor that permits propagation of unfocused ultrasonic waves US, and is also able to receive ultrasonic waves. In the first embodiment, the first ultrasonic sensor 11 as the flat-type transmitting sensor has a single first vibration surface 11a from which ultrasonic waves US are transmitted, and the first vibration surface 11a as a whole is formed in a circular shape. In operation, the ultrasonic waves US are transmitted from the first ultrasonic sensor 11 to at least within an area of the electrode 60 which is opposed to the first vibration surface 11a, via the air layer AR. When the second ultrasonic sensor 12 operates as a transmitting sensor, the sensor 12 operates substantially in the same manner as the first ultrasonic sensor 11, except that the first vibration surface 11a is replaced by a second vibration surface 12a of the second ultrasonic sensor 12.

The second ultrasonic sensor 12 is a flat-type receiving sensor that permits propagation of unfocused ultrasonic waves US, and is also able to transmit ultrasonic waves. In the first embodiment, the second ultrasonic sensor 12 as the flat-type receiving sensor has a single second vibration surface 12a that receives ultrasonic waves US, and the second vibration surface 12a as a whole is formed in a circular shape. The entire area of the second vibration surface 12a of the second ultrasonic sensor 12 is able to receive ultrasonic waves (transmitted waves) US sent from the first ultrasonic sensor 11 for irradiation of the electrode 60 and transmitted through at least the electrode 60, via the air layer AR. When the first ultrasonic sensor 11 operates as a receiving sensor, the sensor 11 operates substantially in the same manner as the second ultrasonic sensor 12, except that the second vibration surface 12a is replaced by the first vibration surface 11a.

The frequencies of the first and second ultrasonic sensors 11, 12 are within the range of 100 KHz-250 KHz, and the first and second ultrasonic sensors 11, 12 have nominal frequencies that are in the same frequency band. The first ultrasonic sensor 11 and the second ultrasonic sensor 12 are both oriented in a direction perpendicular to the electrode 60. Where the frequency of the first and second ultrasonic sensors 11, 12 of the actual-measurement ultrasonic sensor set 10 is 200 KHz, for example, the first ultrasonic sensor 11 and the second ultrasonic sensor 12 are located with the electrode 60 (or the reference foil 65) interposed therebetween, via the air layers AR, such that the opposed first vibration surface 11a and second vibration surface 12a are spaced by a distance of about 70 mm apart from each other.

Next, the first and second calibration ultrasonic sensors 21, 22 of the calibration ultrasonic sensor set 20 will be described in more detail. The first calibration ultrasonic sensor 21 is a flat-type transmitting sensor that permits propagation of unfocused ultrasonic waves US, and is also able to receive ultrasonic waves. Thus, the first calibration ultrasonic sensor 21 is constructed and operates substantially in the same manner as the first and second ultrasonic sensors 11, 12. Namely, in the first embodiment, the first calibration ultrasonic sensor 21 as the flat-type transmitting Sensor has a single first vibration surface 21a from which ultrasonic waves US are transmitted, and the first vibration surface 21a as a whole is formed in a circular shape. In operation, the ultrasonic waves US are transmitted from the first calibration ultrasonic sensor 21 to at least within an area of the reference foil 65 which is opposed to the first vibration surface 21a, via the air layer AR. When the second calibration ultrasonic sensor 22 operates as a transmitting sensor, the sensor 22 operates substantially in the same manner as the first calibration ultrasonic sensor 21, except that the first vibration surface 21a is replaced by a second vibration surface 22a of the second ultrasonic sensor 22.

The second calibration ultrasonic sensor 22 is a flat-type receiving sensor that permits propagation of unfocused ultrasonic waves US, and is also able to transmit ultrasonic waves. Thus, the second calibration ultrasonic sensor 22 is constructed and operates substantially in the same manner as the first and second ultrasonic sensors 11, 12 and the first calibration ultrasonic sensor 21. Namely, in the first embodiment, the second calibration ultrasonic sensor 22 as the flat-type receiving sensor has a single second vibration surface 22a that receives ultrasonic waves US, and the second vibration surface 22a as a whole is formed in a circular shape. The entire area of the second vibration surface 22a of the second calibration ultrasonic sensor 22 is able to receive ultrasonic waves (transmitted waves) US sent from the first calibration ultrasonic sensor 21 for irradiation of the reference foil 65 and transmitted through at least the reference foil 65, via the air layer AR. When the first calibration ultrasonic sensor 21 operates as a receiving sensor, the sensor 21 operates substantially in the same manner as the second calibration ultrasonic sensor 22, except that the second vibration surface 22a is replaced by the first vibration surface 21a.

Like the first and second ultrasonic sensors 11, 12, the frequencies of the first and second calibration ultrasonic sensors 21, 22 are within the range of 100 KHz-250 KHz, and the first and second calibration ultrasonic sensors 21, 22 have nominal frequencies that are in the same frequency band. The first calibration ultrasonic sensor 21 and the second calibration ultrasonic sensor 22 are both oriented in a direction perpendicular to the reference foil 65. Like the actual-measurement ultrasonic sensor set 10, where the frequency of the first and second calibration ultrasonic sensors 21, 22 of the calibration ultrasonic sensor set 20 is 200 KHz, for example, the first calibration ultrasonic sensor 21 and the second calibration ultrasonic sensor 22 are located with the reference foil 65 interposed therebetween, via the air layers AR, such that the opposed first vibration surface 21a and second vibration surface 22a are spaced by a distance of about 70 mm apart from each other.

As shown in FIG. 2, the first ultrasonic sensor 11 and the first calibration ultrasonic sensor 21 are electrically connected to a first ultrasonic oscillator 11F. The first ultrasonic oscillator 11F has an oscillating circuit for applying voltage to the first ultrasonic sensor 11 and the first calibration ultrasonic sensor 21 so as to produce ultrasonic vibrations in the first vibration surfaces 11a, 21a, and a receiving circuit for converting vibrations of ultrasonic waves received by the first vibration surfaces 11a, 21a, into voltage signals, and receiving the voltage signals.

The second ultrasonic sensor 12 and the second calibration ultrasonic sensor 22 are electrically connected to a second ultrasonic oscillator 12F for producing ultrasonic vibrations in the second vibration surfaces 12a, 22a. The second ultrasonic oscillator 12F has an oscillating circuit for applying voltage to the second ultrasonic sensor 12 and the second calibration ultrasonic sensor 22 so as to produce ultrasonic vibrations in the second vibration surfaces 12a, 22a, and a receiving circuit for converting vibrations of ultrasonic waves received by the second vibration surfaces 12a, 22a, into voltage signals, and receiving the voltage signals. The first ultrasonic oscillator 11F and the second ultrasonic oscillator 12F are electrically connected to the ultrasonic measurement control unit 5.

Next, the ultrasonic measurement control unit 5 will be described with reference to FIG. 2. The ultrasonic measurement control unit 5 controls the actual-measurement ultrasonic sensor set 10 (the first and second ultrasonic sensors 11, 12) and the calibration ultrasonic sensor set 20 (the first and second calibration ultrasonic sensors 21, 22), more specifically, controls transmission (sending and receiving) of ultrasonic waves US, and measurement conditions between the actual-measurement ultrasonic sensor set 10 and the calibration ultrasonic sensor set 20.

The ultrasonic measurement control unit 5 is configured to cause each of the first and second ultrasonic sensors 11, 12 of the actual-measurement ultrasonic sensor set 10 and the first and second calibration ultrasonic sensors 21, 22 of the calibration ultrasonic sensor set 20 to generate ultrasonic waves US, under control conditions that the maximum oscillation voltage is 1 KV, the maximum oscillation frequency is 10 Hz (oscillation occurs once per 100 µs), the maximum number of generated waves (the number of waves that can be transmitted within a given time) is 100 waves, and the maximum A/D conversion frequency is 100 MHz, for example.

In the first embodiment, the number of generated waves is 30 waves for each measurement. In order to prevent the waveform of the generated 30 waves from overlapping another waveform of 30 waves, the actual-measurement ultrasonic sensor set 10 and the calibration ultrasonic sensor set 20 are positioned such that the distance between the first oscillation surface 11a and the electrode 60, distance between the first oscillation surface 11a and the reference foil 65, distance between the second oscillation surface 12a and the electrode 60, distance between the second oscillation surface 12a and the reference foil 65, distance between the first oscillation surface 21a and the reference foil 65, and the distance between the second oscillation surface 22a and the reference foil 65 are all set to 35 mm. The actual-measurement ultrasonic sensor set 10 is in a first condition when the first ultrasonic sensor 11 sends ultrasonic waves, and the second ultrasonic sensor 12 receives the waves, and is in a second condition when the second ultrasonic sensor 12 sends ultrasonic waves, and the first ultrasonic sensor 11 receives the waves. In this case, the ultrasonic measurement control unit 5 switches the first ultrasonic sensor 11 and the second ultrasonic sensor 12 between the first condition and the second condition, so that the first ultrasonic sensor 11 operates differently from the second ultrasonic sensor 12.

Also, the ultrasonic measurement control unit 5 feeds back measurement condition values used by the calibration ultrasonic sensor set 20, to the actual-measurement ultrasonic sensor set 10. More specifically, in the case of the first condition, sending conditions under which ultrasonic waves are sent from the first calibration ultrasonic sensor 21 via the air layer AR, namely, measurement condition values, such as the temperature of the air layer AR, the density of the air layer AR, and the temperature of the first calibration ultrasonic sensor 21 itself, are applied, as measurement conditions used when calibration is performed by the calibration ultrasonic sensor set 20, and adapted to the first ultrasonic sensor 11 of the actual-measurement ultrasonic sensor set 10.

At the same time, receiving conditions under which ultrasonic waves US transmitted through the reference foil 65 propagate through the air layer AR and are received by the second calibration ultrasonic sensor 22, namely, measurement condition values, such as the temperature of the air layer AR, the density of the air layer AR, and the temperature of the second calibration ultrasonic sensor 22 itself, are applied and adapted to the second ultrasonic sensor 12 of the actual-measurement ultrasonic sensor set 10. In the second condition, the actual-measurement ultrasonic sensor set 10 operates in substantially the same manner as that in the case of the first condition as described above, merely by replacing the first ultrasonic sensor 11 in the first condition with the second ultrasonic sensor 12, and the calibration ultrasonic sensor set 20 operates in substantially the same manner as that in the case of the first condition as described above, merely by replacing the first calibration ultrasonic sensor 21 in the first condition with the second calibration ultrasonic sensor 22. Thus, further explanation will not be provided.

The ultrasonic measurement control unit 5 is electrically connected to upper slide shaft 55A and lower slide shaft 55B which will be described later, and is configured to control the movements of the upper slide shaft 55A and lower slide shaft 55B in synchronization with each other. The ultrasonic measurement control unit 5 is also electrically connected to the thickness computing unit 40.

The thickness computing unit 40 calculates the basis weight and coating profile of the electrode paste 62, based on a received signal of ultrasonic waves US received by a receiving-side ultrasonic sensor as one of the first ultrasonic sensor 11 and the second ultrasonic sensor 12. The thickness computing unit 40 includes a microcomputer (not shown) of known configuration having CPU, RAM, ROM, etc.

The RAM of the thickness computing unit 40 receives, as set values, the attenuation factor of ultrasonic waves US when propagating through the air layer AR, the attenuation factor of ultrasonic waves US when transmitted through the reference foil 65, the attenuation factor of ultrasonic waves US when transmitted through the electrode 60, the attenuation factor of ultrasonic waves US when transmitted through the metal foil 61 or the thickness of the metal foil 61, the atmosphere temperature of the air layer AR measured by a thermometer or thermometers (not shown), the temperatures of the first and second ultrasonic sensors 11, 12 and the first and second calibration ultrasonic sensors 21, 22, the probe-to-probe distance between the first vibration surface 11a, 21a and the second vibration surface 12a, 22a, the sound velocity, density, and acoustic impedance corresponding to the temperature, in the air layer AR, and so forth.

Also, the ROM of the thickness computing unit 40 stores a program for executing calibration of the first and second calibration ultrasonic sensors 21, 22 of the calibration ultrasonic sensor set 20, a program for calculating the attenuation factor of transmitted waves generated by one of the first and second ultrasonic sensors 11, 12 of the actual-measurement ultrasonic sensor set 10 and transmitted through the reference foil 65, a program for calculating the attenuation factor of transmitted waves generated by one of the first and second ultrasonic sensors 11, 12 of the actual-measurement ultrasonic sensor set 10 and transmitted through the electrode 60 (the electrode paste 62), a program for correcting the sonic waveform of the transmitted and received waves by approximating the waveform by a sine wave, a basis-weight calculation program for computing the thickness, or basis weight, of the electrode paste 62, based on the calculated attenuation factor of the transmitted waves, a program for displaying the computation results in the form of numerical values and/or images, on the monitor 41, a program for moving the upper slide shaft 55A and the lower slide shaft 55B in the width direction (Y-axis direction), and other programs.

In the thickness computing unit 40, the CPU is loaded with the above-indicated programs, so as to perform certain operations, such as displaying numerical values and/or images representing the basis weight and coating profile of the electrode paste 62, on the monitor 41 connected to the thickness computing unit 40, as well as operating the upper slide shaft 55A and the lower slide shaft 55B.

Figure 4:
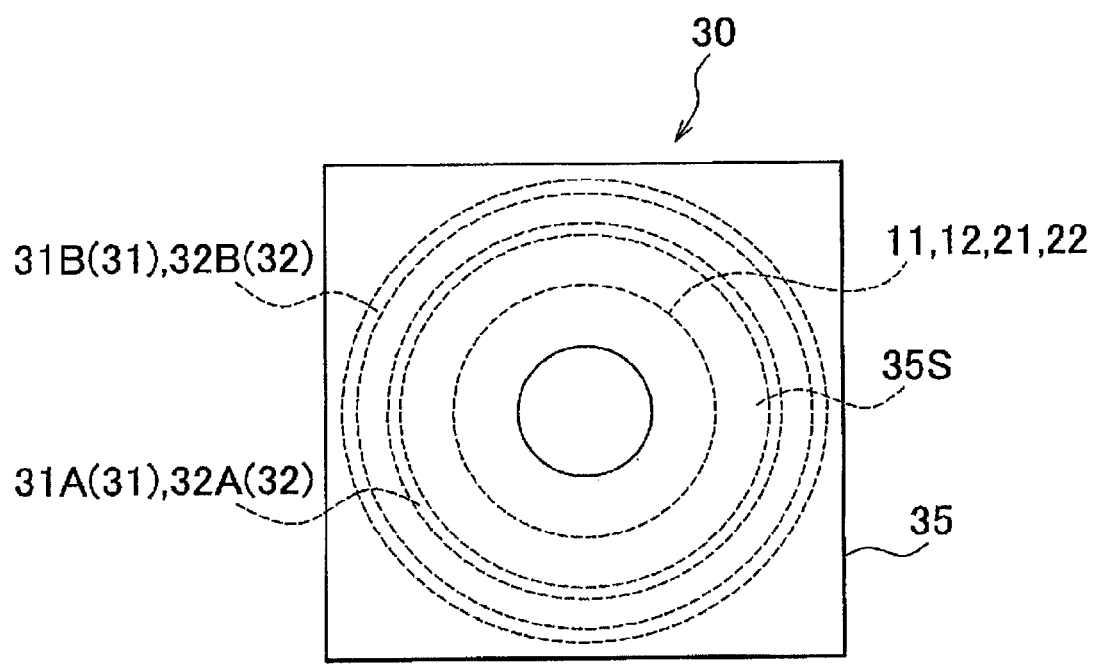
FIG. 4 is a top view of a sensor unit of the ultrasonic measuring system according to the first embodiment of FIG. 1.
Figure 5:
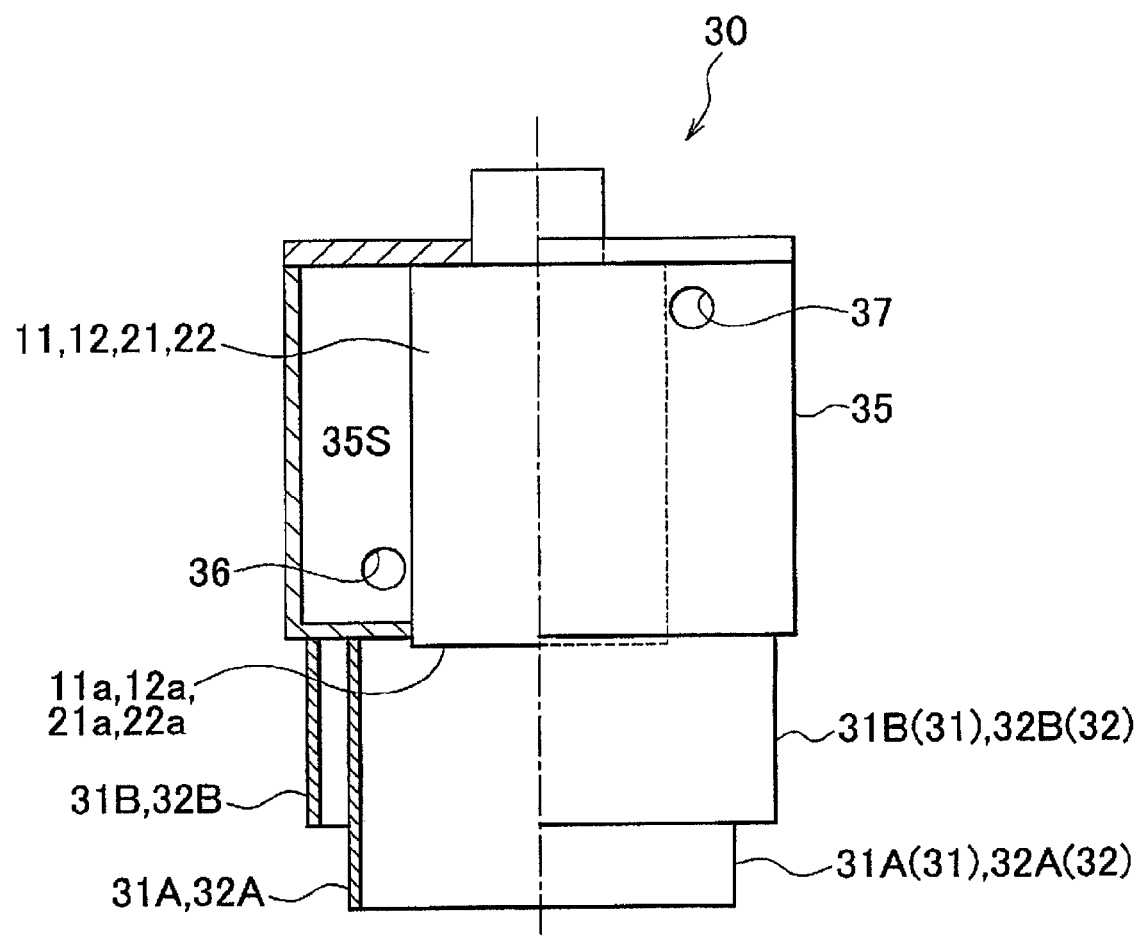
FIG. 5 is a half cross-sectional view of the sensor unit shown in FIG. 4.
Figure 6:
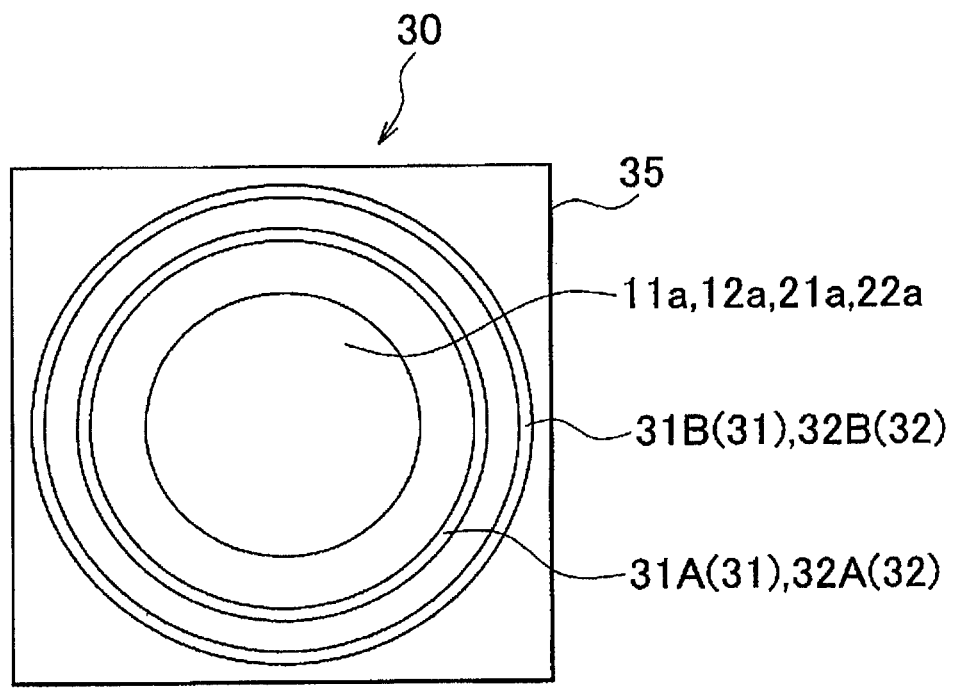
FIG. 6 is a bottom view of the sensor unit shown in FIG. 4.

Next, a sensor unit 30 in which each of the first and second ultrasonic sensors 11, 12 and the first and second calibration ultrasonic sensors 21, 22 is incorporated will be described with reference to FIG. 3 through FIG. 6. FIG. 3 is a cross-sectional view as seen in the direction of arrows A-A in FIG. 1, showing a principal portion of the system including the first and second ultrasonic sensors 11, 12, and the electrode 60. FIG. 4 is a top view of the sensor unit. FIG. 5 shows a half section of the sensor unit shown in FIG. 4. FIG. 6 is a bottom view of the sensor unit shown in FIG. 4.

Initially, the sensor unit 30 in which each sensor of the actual-measurement ultrasonic sensor set 10 is housed will be described. In the actual-measurement ultrasonic sensor set 10, each of the first and second ultrasonic sensors 11, 12 is provided with a cylindrical cover 31 for actual-measurement sensors, which surrounds the air layer AR between the first or second vibration surface 11a, 12a as an ultrasonic vibration surface and the electrode 60, as shown in FIG. 5 and FIG. 6.

The actual-measurement sensor cover 31 is formed of a material, such as aluminum, having high thermal conductivity and excellent heat dissipation characteristic, and has a dual structure consisting of an inner cylindrical cover 31A, and an outer cylindrical cover 31B located radially outwardly of the inner cylindrical cover 31A, as shown in FIG. 5 and FIG. 6. The inner cylindrical cover 31A of the actual-measurement sensor cover 31 is arranged to contain or surround a lower portion of the first or second ultrasonic sensor 11, 12 and the first or second vibration surface 11a, 12a, so that the air layer AR between the first or second vibration surface 11a, 12a and the electrode 60 has no influence of convection or flow of air from the outside. The outer cylindrical cover 31B is formed to be shorter than the inner cover 31A as measured in the direction (Z-axis direction) parallel to the direction of the thickness of the metal foil 61, so that the outer cylindrical cover 31B is spaced by a larger distance from the electrode 60 (or the reference foil 65) than the inner cylindrical cover 31A.

In the meantime, each of the main bodies of the first and second ultrasonic sensors 11, 12 is held and fixed by a sensor holding member 35 having a columnar interior space having the larger diameter than the main body of the first or second ultrasonic sensor 11, 12, as shown in FIG. 4 through FIG. 6. The sensor holding member 35 is formed of a material, such as aluminum, having high thermal conductivity and excellent heat dissipation characteristic, and a space between the sensor holding member 35 and the outer periphery of the first or second ultrasonic sensor 11, 12 provides a cooling chamber 35S in which the first or second ultrasonic sensor 11, 12 is cooled by air. The sensor holding member 35 is formed with an air introduction hole 36 through which cool air is introduced into the cooling chamber 35S, and an air discharge hole 37 through which warm air derived from the self-heated first or second ultrasonic sensor 11, 12 is discharged from the cooling chamber 35S. Namely, the self-heated first or second ultrasonic sensor 11, 12 is cooled by the cool air introduced through the air induction hole 36, and the warm air resulting from removal of heat from the first or second ultrasonic sensor 11, 12 is discharged through the air discharge hole 37.

Next, the sensor unit 30 in which each sensor of the calibration ultrasonic sensor set 20 is housed will be described. In the calibration ultrasonic sensor set 20, each of the first and second calibration ultrasonic sensors 21, 22 is provided with a cylindrical cover 32 for calibration sensors, which surrounds the air layer AR between the first or second vibration surface 21a, 22a as an ultrasonic vibration surface and the reference foil 65, as shown in FIG. 5.

The calibration sensor cover 32 is formed of a material, such as aluminum, having high thermal conductivity and excellent heat dissipation characteristic, and has a dual structure consisting of an inner cylindrical cover 31A, and an outer cylindrical cover 31B located radially outwardly of the inner cylindrical cover 31A, as shown in FIG. 5 and FIG. 6. The inner cylindrical cover 31A of the calibration sensor cover 32 is arranged to contain or surround a lower portion of the first or second calibration ultrasonic sensor 21, 22 and the first or second vibration surface 21a, 22a, so that the air layer AR between the first or second vibration surface 21a, 22a and the reference foil 65 has no influence of convection or flow of air from the outside. The outer cylindrical cover 31B is formed to be shorter than the inner cylindrical cover 31A as measured in the direction (Z-axis direction) parallel to the direction of the thickness of the reference foil 65, so that the outer cylindrical cover 31B is spaced by a larger distance from the reference foil 65 than the inner cylindrical cover 31A.

In the meantime, each of the first and second calibration ultrasonic sensors 21, 22 is held and fixed by a sensor holding member 35 having a columnar interior space having the larger diameter than the first or second calibration ultrasonic sensor 21, 22, as shown in FIG. 4 through FIG. 6. The sensor holding member 35 is formed of a material, such as aluminum, having high thermal conductivity and excellent heat dissipation characteristic, and a space between the sensor holding member 35 and the outer periphery of the first or second calibration ultrasonic sensor 21, 22 provides a cooling chamber 35S in which the first or second calibration ultrasonic sensor 21, 22 is cooled by air. The sensor holding member 35 is formed with an air introduction hole 36 through which cool air is introduced into the cooling chamber 35S, and an air discharge hole 37 through which warm air derived from the self-heated first or second calibration ultrasonic sensor 21, 22 is discharged from the cooling chamber 35S. Namely, the self-heated first or second calibration ultrasonic sensor 21, 22 is cooled by the cool air introduced through the air induction hole 36, and the warm air resulting from removal of heat from the first or second calibration ultrasonic sensor 21, 22 is discharged through the air discharge hole 37.

In the actual-measurement sensor cover 31 (or calibration sensor cover 32) of the first embodiment, an air channel between the inner cylindrical cover 31A and the outer cylindrical cover 31B communicates with the cooling chamber 35S of the sensor holding member 35, though not shown in FIG. 5. However, the air channel and the cooling chamber 35S may not particularly communicate with each other.

As shown in FIG. 1 and FIG. 2, the measuring unit 7 includes a pair of upper slide shaft 55A and lower slide shaft 55B, which are disposed on the opposite sides of the electrode 60 and the reference foil 65. Each of the upper and lower slide shafts 55A, 55B extends over the electrode 60 and the reference foil 65 in the width direction Y, such that it is movable in the width direction Y by a driving source (not shown). The operations, namely, synchronized movement and stopping, of the upper slide shaft 55A and lower slide shaft 55B are controlled as desired by the ultrasonic measurement control unit 5 to which the slide shafts 55A, 55B are electrically connected.

The sensor unit 30 in which the first ultrasonic sensor 11 of the actual-measurement ultrasonic sensor set 10 is housed in the sensor holding member 35, and the sensor unit 30 in which the first calibration ultrasonic sensor 21 of the calibration ultrasonic sensor unit 20 is housed in the sensor holding member 35 are fixedly mounted on predetermined positions of the upper slide shaft 55A, such that these sensor units 30 are spaced by a given distance from each other. The mounting positions of these two sensor units 30 on the upper slide shaft 55A may be changed as desired.

The sensor unit 30 in which the second ultrasonic sensor 12 of the actual-measurement ultrasonic sensor set 10 is housed in the sensor holding member 35, and the sensor unit 30 in which the second calibration ultrasonic sensor 22 of the calibration ultrasonic sensor set 20 is housed in the sensor holding member 35 are fixedly mounted on predetermined positions of the lower slide shaft 55B which are opposed to the respective sensor units 30 on the upper slide shaft 55A, such that the sensor units 30 are spaced by a given distance from each other. The mounting positions of these two sensor units 30 on the lower slide shaft 55B may be changed as desired.

Namely, the actual-measurement ultrasonic sensor set 10 and the calibration ultrasonic sensor set 20 are arranged to move in the width direction Y, by means of the pair of upper slide shaft 55A and the lower slide shaft 55B. More specifically, the calibration ultrasonic sensor set 20 is movable at least within a range between a first position L1 at which the reference foil 65 is placed, and a second position L2 (that lies outside the first position L1) where only the air layer AR is present between the first calibration ultrasonic sensor 21 and the second calibration ultrasonic sensor 22. Also, the actual-measurement ultrasonic sensor set 10 is movable at least within a range between the first position L1, and a third position L3 (that lies outside the first position L1) where the electrode 60 is placed.

Next, an ultrasonic measuring method according to the first embodiment of the invention will be described. The ultrasonic measuring method of the first embodiment is a method for performing quality check on the basis weight of the electrode paste 62, using the ultrasonic measuring system 1 constructed as described above. The ultrasonic measuring method of the first embodiment uses a pair of ultrasonic sensors in the form of the first ultrasonic sensor 11 and the second ultrasonic sensor 12, and the first ultrasonic sensor 11 is placed, via the air layer AR, on one side of the electrode 60 as viewed in the thickness direction Z of the electrode 60, which is formed by coating the opposite surfaces 61a, 61b of the metal foil 61 made of a metal and wound in the form of a roll, with the electrode paste 62, while the second ultrasonic sensor 12 is placed, via the air layer AR, on the other side of the electrode 60. In this condition, the thickness (basis weight) of the electrode paste 62 is measured by transmitting ultrasonic waves US between the first ultrasonic sensor 11 and the second ultrasonic sensor 12. The ultrasonic sensor sets used in the ultrasonic measuring method include at least one set of actual-measurement ultrasonic sensors 10 for measuring the basis weight of the electrode paste 62, and the calibration ultrasonic sensor set 20 consisting of the first calibration ultrasonic sensor 21 and the second calibration ultrasonic sensor 22, aside from the first ultrasonic sensor 11 and the second ultrasonic sensor 12. In operation, the calibration ultrasonic sensor set 20 performs calibration, during measurement of the thickness of the electrode paste 62, and the actual-measurement ultrasonic sensor set 10 calculates the basis weight of the electrode paste 62, using measurement condition values obtained by the calibration ultrasonic sensor set 20.

The ultrasonic measuring method according to the first embodiment of the invention is characterized in that flat-type ultrasonic sensors that permit propagation of unfocused ultrasonic waves US are used as the first calibration ultrasonic sensor 21 and second calibration ultrasonic sensor 22 of the calibration ultrasonic sensor set 20, and flat-type ultrasonic sensors that permit propagation of unfocused ultrasonic waves US are used as the first ultrasonic sensor 11 and second ultrasonic sensor 12 of the actual-measurement ultrasonic sensor set 10.

Figure 9A:
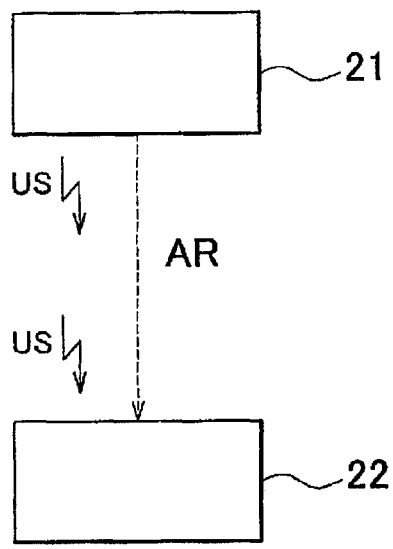
FIG. 9A is a schematic view of the calibration ultrasonic sensor set when transmitting ultrasonic waves with no reference foil placed between sensors, for explaining the manner of determining the attenuation factor of ultrasonic waves by the calibration ultrasonic sensor set, in the first embodiment of FIG. 1.
Figure 9B:
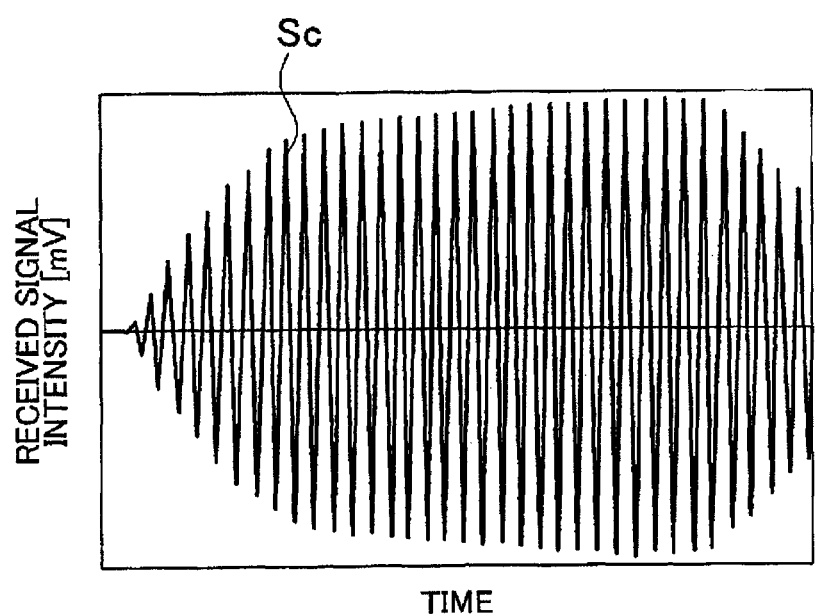
FIG. 9B shows a received signal of ultrasonic waves received by a receiving-side ultrasonic sensor in the condition of FIG. 9A.
Figure 10A:
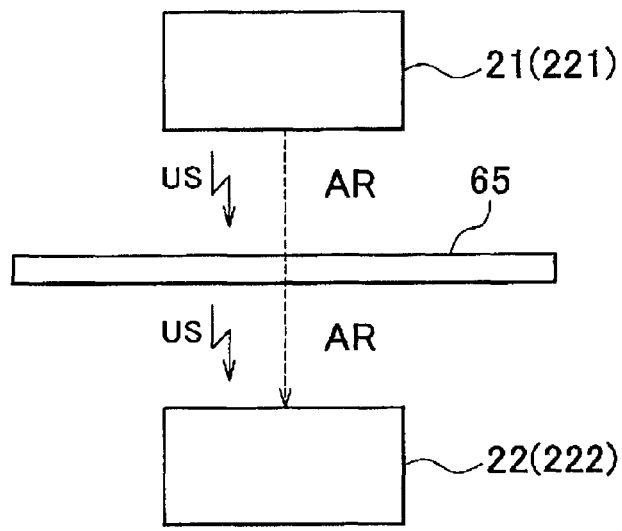
FIG. 10A is a schematic view of the calibration ultrasonic sensor set when transmitting ultrasonic waves with a reference foil placed between sensors, for explaining the manner of determining the attenuation factor of ultrasonic waves by the calibration ultrasonic sensor set, in the first embodiment of FIG. 1.
Figure 10B:
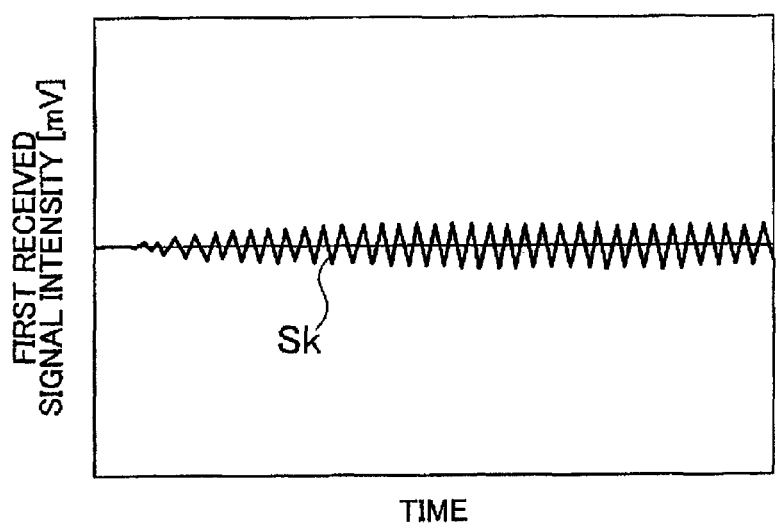
FIG. 10B shows a received signal of ultrasonic waves received by the receiving-side ultrasonic sensor in the condition of FIG. 10A.
Figure 11A:
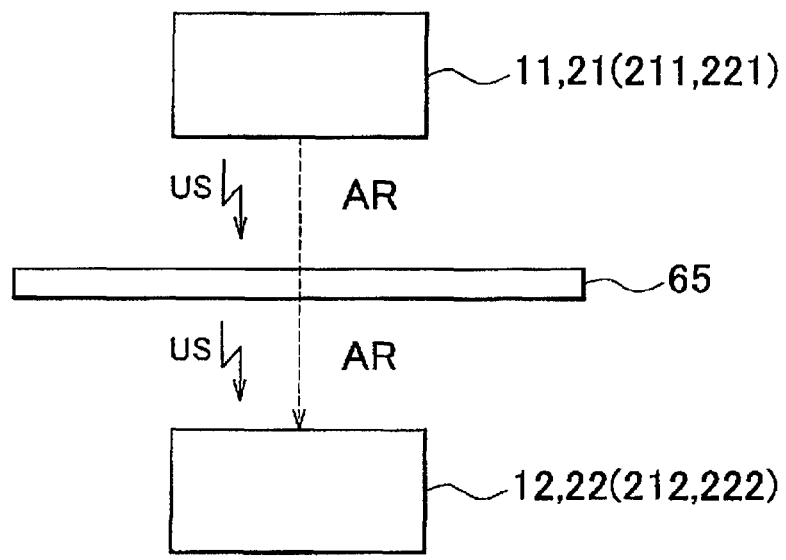
FIG. 11A is a schematic view of each of the calibration ultrasonic sensor set and the actual-measurement ultrasonic sensor set when transmitting ultrasonic waves, so as to perform calibration in the first embodiment.
Figure 11B:
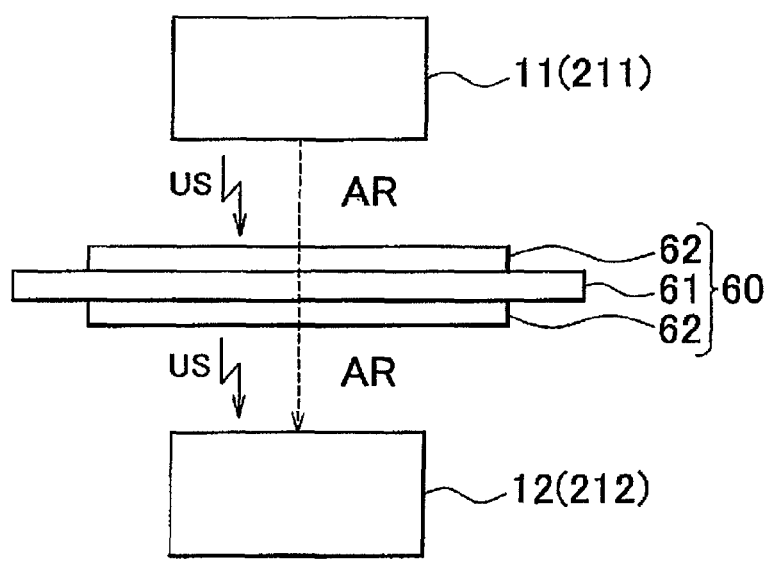
FIG. 11B is a schematic view of the actual-measurement ultrasonic sensor set when transmitting ultrasonic waves, so as to actually measure the basis weight of the electrode in the first embodiment.
Figure 12:
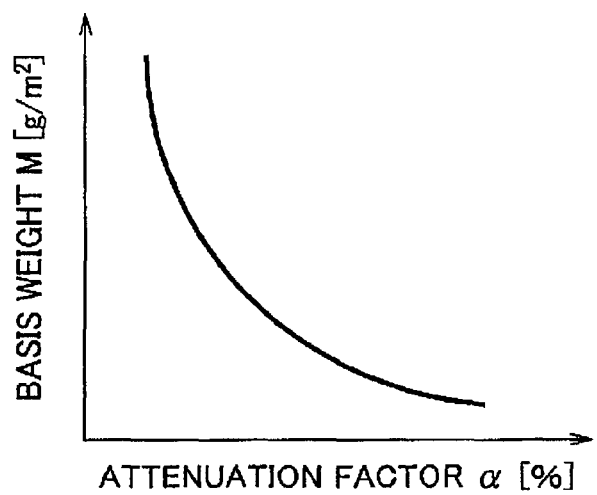
FIG. 12 is a graph indicating the relationship between the attenuation factor of ultrasonic waves of the receiving-side ultrasonic sensor, and the basis weight, in the first embodiment.

Reference is now made to FIGS. 9A and 9B through FIG. 12. FIGS. 9A and 9B are explanatory views useful for explaining how the attenuation factor of ultrasonic waves is determined by the calibration ultrasonic sensor set. FIG. 9A is a schematic view of the calibration ultrasonic sensor set when ultrasonic waves are transmitted with no reference foil placed between the sensors, and FIG. 9B indicates a received signal of ultrasonic waves received by the receiving-side ultrasonic sensor in the condition of FIG. 9A. FIGS. 10A and 10B are explanatory views useful for explaining how the attenuation factor of ultrasonic waves is determined by the calibration ultrasonic sensor set. FIG. 10A is a schematic view of the calibration ultrasonic sensor set when ultrasonic waves are transmitted in the presence of a reference foil, and FIG. 10B indicates a received signal of ultrasonic waves received by the receiving-side ultrasonic sensor in the condition of FIG. 10A. FIGS. 11A and 11B are schematic views of the calibration ultrasonic sensor set and the actual-measurement ultrasonic sensor set, respectively, when ultrasonic waves are transmitted. FIG. 11A shows the manner of performing calibration, and FIG. 11B shows the manner of actually measuring the basis weight of the electrode. FIG. 12 is a graph indicating the relationship between the attenuation factor of ultrasonic waves received by the receiving-side ultrasonic sensor, and the basis weight.

In the ultrasonic measuring method according to the first embodiment of the invention, prior to the actual measurement by the actual-measurement ultrasonic sensor set 10, the reference foil 65 used for calibration is placed between the first calibration ultrasonic sensor 21 and the second calibration ultrasonic sensor 22 of the calibration ultrasonic sensor set 20, as shown in FIG. 10A, and ultrasonic waves US sent from the first calibration ultrasonic sensor 21 are transmitted through the reference foil 65, so that a first received signal $S_K$ representing ultrasonic waves US received by the second calibration ultrasonic sensor 22 is obtained in advance as a measurement condition value. In the actual-measurement ultrasonic sensor set 10, a second received signal $S_X$ (corresponding to $S_C$ shown in FIG. 9B) representing ultrasonic waves US transmitted through the electrode 60 between the first ultrasonic sensor 11 and the second ultrasonic sensor 12 is obtained, as shown in FIG. 11B, and the basis weight (or thickness) of the electrode paste 62 is calculated based on the relative ratio of the first received signal $S_K$ and the second received signal $S_X$.

More specifically, the basis weight of a foil can be determined according to the following equation, using the attenuation factor of ultrasonic waves US transmitted through the foil, and the relationship between the basis weight of the foil and the attenuation factor of the ultrasonic waves US is indicated in FIG. 12.

$$M = A/\alpha \qquad (5)$$

where M is the basis weight (g/m²) of the foil, α is the attenuation factor (%) of ultrasonic waves, and A is a constant.

Here, the relationship between the basis weight and the attenuation factor of ultrasonic waves will be explained, using three types of reference foils A, B, C (corresponding to the reference foil 65) for comparison, which have different basis weights. The attenuation factor α of ultrasonic waves is the relative ratio of the received signal (no-foil received signal) $S_C$ of ultrasonic waves US transmitted only through the air layer AR and received, with no foil placed between the first calibration ultrasonic sensor 21 and the second calibration ultrasonic sensor 22 of the calibration ultrasonic sensor set 20, and the received signal (in the presence of a foil) $S_K$ of ultrasonic waves US transmitted through the reference foil 65 placed between the first calibration ultrasonic sensor 21 and the second calibration ultrasonic sensor 22 and received.

(1) About Reference Foil A for Comparison

The basis weight $M_A$ of the reference foil A for comparison is obtained as follows, according to Eq. (5) above.

$$M_A = A/(S_{KA}/S_C) \tag{6}$$

From Eq. (6) above, the constant A is obtained as follows.

$$A = M_A \times S_{KA}/S_C \tag{7}$$

where $M_A$ is the basis weight (g/m²) of the reference foil A for comparison, $S_{KA}$ is the received signal in the presence of the reference foil A for comparison, and $S_C$ is the no-foil received signal.

(2) About Reference Foil B for Comparison

The basis weight $M_B$ of the reference foil B for comparison is obtained as follows, according to Eq. (5) above.

$$M_B = A/(S_{KB}/S_C) \tag{8}$$

From Eq. (8) above, the constant A is obtained as follows.

$$A = M_B \times S_{KB}/S_C \tag{9}$$

where $M_B$ is the basis weight (g/m²) of the reference foil B for comparison, and $S_{KB}$ is the received signal in the presence of the reference foil B for comparison.

(3) About Reference Foil C for Comparison

The basis weight $M_C$ of the reference foil C for comparison is obtained as follows, according to Eq. (5) above.

$$M_C = A/(S_{KC}/S_C) \tag{10}$$

From Eq. (10) above, the constant A is obtained as follows.

$$A = M_C \times S_{KC}/S_C \tag{11}$$

where $M_C$ is the basis weight (g/m²) of the reference foil C for comparison, and $S_{KC}$ is the received signal in the presence of the reference foil C for comparison.

Since the constant A and the no-foil received signal $S_C$ are constant, as indicated in Eq. (7), Eq. (9) and Eq. (11), the following equation (Eq. (12)) is derived from Eq. (7), Eq. (9) and Eq. (11).

$$M_A \times S_{KA} = M_B \times S_{KB} = M_C \times S_{KC} = A \times S_C = \text{constant} \tag{12}$$

On the other hand, the basis weight $M_X$ of a reference foil X for comparison, of which the basis weight is unknown, namely, the basis weight $M_X$ of the electrode 60, is obtained as follows, according to Eq. (5) above.

$$M_X = A/(S_X/S_C) \tag{13}$$

where Mx is the basis weight (g/m²) of the reference foil X for comparison (the electrode 60), and $S_X$ is a received signal in the presence of the reference foil X for comparison (the electrode 60).

By using Eq. (12) above, Eq. (13) is converted into the following equation (Eq. (14)).

$$M_X = A \times S_C/S_X = M_A \times S_{KA}/S_X = M_B \times S_{KB}/S_X = M_C \times S_{KC}/S_X \tag{14}$$

Since it is found from Eq. (12) that the numerators in Eq. (14) are a constant value, the basis weight $M_X$ of the electrode 60 can be determined from the relative ratio of the constant value obtained from Eq. (12) and the received signal $S_X$ obtained in the presence of the electrode 60.

In the ultrasonic measuring method according to the first embodiment of the invention, prior to the actual measurement by the actual-measurement ultrasonic sensor set 10, the calibration ultrasonic sensor set 20 initially obtains the attenuation factor of ultrasonic waves US transmitted through the reference foil 65 used for calibration, in advance, as a first received signal $S_K$. More specifically, in the case where the reference foil A for comparison is the reference foil 65 used for calibration, for example, the no-foil received signal $S_C$ in the denominator of Eq. (6) is a received signal as a constant of ultrasonic waves US transmitted only through the air layer AR and received, with no reference foil 65 placed between the first calibration ultrasonic sensor 21 and the second calibration ultrasonic sensor 22, as shown in FIG. 9A. Also, the received signal $S_{KA}$ obtained in the presence of the reference foil A for comparison, in the denominator of Eq. (6), is the first received signal $S_K$ itself.

If the weight and area of the reference foil 65 are determined or known in advance, the density of the reference foil 65 can be grasped. Since the basis weight $M_A$ of the reference foil 65 is equivalent to the density of the reference foil 65, the basis weight $M_A$ is obtained from the weight and area of the reference foil 65. Accordingly, the numerator in the above-indicated Eq. (14): $M_X = M_A \times S_{KA}/S_X$ can be calculated from the predetermined weight and area of the reference foil 65, and the first received signal $S_K$.

Subsequently, for actual measurement of the basis weight (thickness) of the electrode paste 62 of the electrode 60, the electrode 60 is placed between the first ultrasonic sensor 11 and the second ultrasonic sensor 12 of the actual-measurement ultrasonic sensor set 10, as shown in FIG. 11B, and ultrasonic waves US sent from the first ultrasonic sensor 11 are transmitted through the electrode 60, so that a second received signal Sx of ultrasonic waves US received by the second ultrasonic sensor 12 is obtained. As described above, the second received signal $S_X$ as the denominator of Eq. (14) is the thus obtained second received signal $S_X$ itself, namely, the received signal of ultrasonic waves US propagated through the reference foil X for comparison, whose basis weight is unknown, i.e., through the electrode 60 to be measured, and received. Thus, the basis weight (thickness) of the electrode paste 62 is calculated based on the relative ratio of the first received signal $S_K$ and the second received signal $S_X$.

In the ultrasonic measuring method of the first embodiment, the actual-measurement ultrasonic sensor set 10 is moved to the position at which the reference foil 65 is placed, and the actual-measurement ultrasonic sensor set 10 obtains a third received signal $S_Y$ (corresponding to $S_C$ shown in FIG. 9B) of ultrasonic waves US that are sent from the first ultrasonic sensor 11, transmitted through the reference foil 65, and received by the second ultrasonic sensor 12. In the ultrasonic measuring method of the first embodiment, the first and second calibration ultrasonic sensors 21, 22, and the first and second ultrasonic sensors 11, 12 send and receive ultrasonic waves in synchronization with each other.

Figure 8:
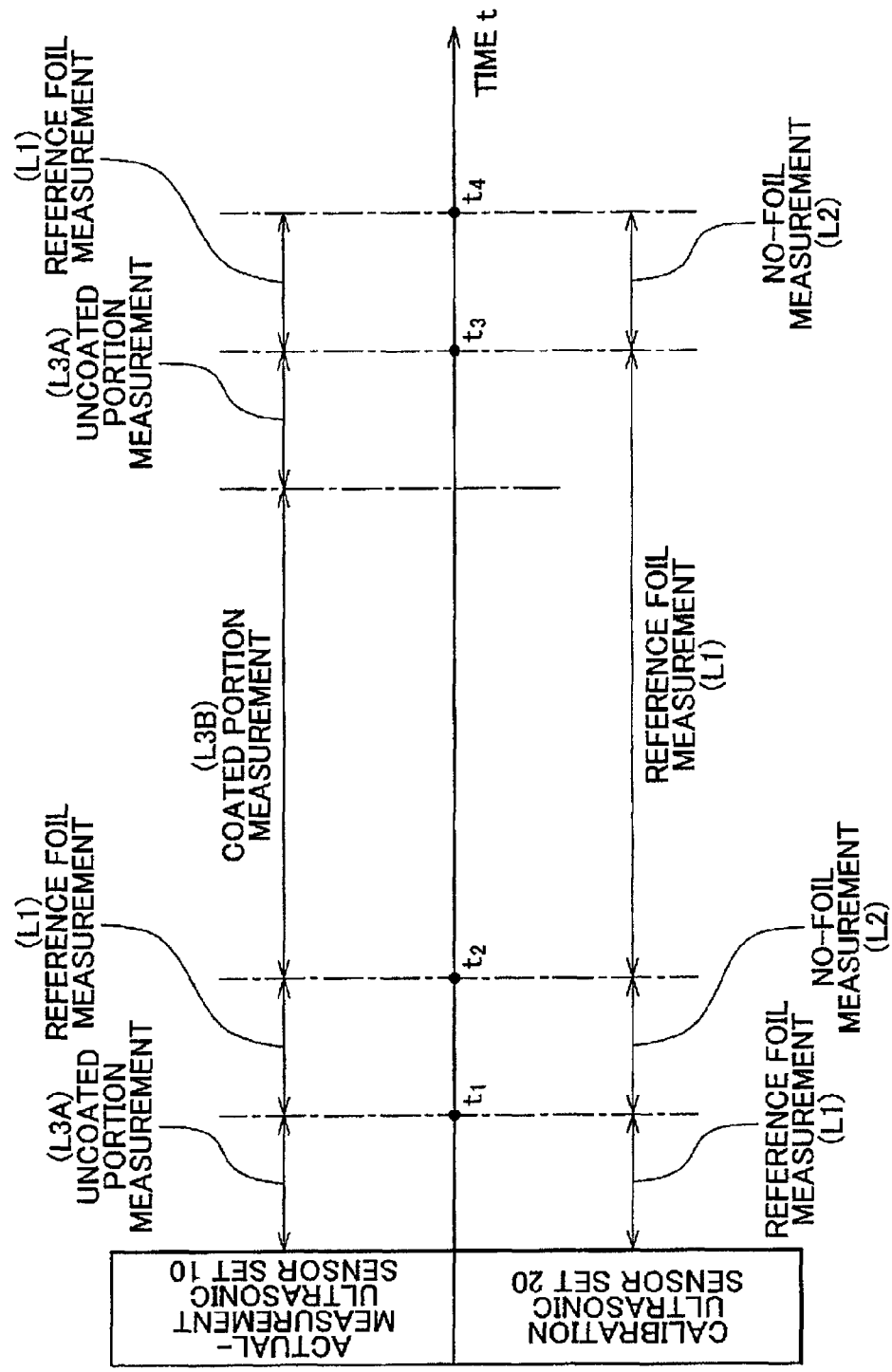
FIG. 8 is a time chart indicating movements of a calibration ultrasonic sensor set and an actual-measurement ultrasonic sensor set in the first embodiment of FIG. 1.

Next, the ultrasonic measuring method according to the above-described first embodiment of the invention, including specific operations of the ultrasonic measuring system 1, will be described with reference to FIG. 2 and FIG. 8. FIG. 8 is a time chart indicating the movements of the calibration ultrasonic sensor set and actual-measurement ultrasonic sensor set. First, there are slight individual differences in ultrasonic vibration characteristics, among the first and second ultrasonic sensors 11, 12 of the actual-measurement ultrasonic sensor set 10, and the first and second calibration ultrasonic sensors 21, 22 of the calibration ultrasonic sensor set 20. Therefore, prior to the actual measurement by the actual-measurement ultrasonic sensor set 10, the oscillation frequency as the maximum output of each of the first and second ultrasonic sensors 11, 12 and the first and second calibration ultrasonic sensors 21, 22 is checked and grasped in advance. Also, the actual-measurement ultrasonic sensor set 10 and the calibration ultrasonic sensor set 20 are both operated at the same time for a given period of time, to be warmed up, so as to achieve a thermal equilibrium or balance between the temperatures of the self-heated first and second ultrasonic sensors 11, 12 and the first and second calibration ultrasonic sensors 21, 22, and the atmospheric temperature.

Then, upon the start of calculation of the basis weight of the electrode paste 62 (the actual measurement of the thickness), both of the actual-measurement ultrasonic sensor set 10 and the calibration ultrasonic sensor set 20 in the ultrasonic measuring system 1 are constantly operated, as shown in FIG. 8, so that ultrasonic waves US are transmitted and received concurrently in the respective sensor sets. In the ultrasonic measuring system 1, the first ultrasonic sensor 11 of the actual-measurement ultrasonic sensor set 10 produces 30 oscillatory waves for each measurement, at a first position L1 at which the reference foil 65 is placed, third positions L3A at which uncoated portions of the metal foil 61 in which the metal foil 61 is not coated with the electrode paste 62 are located, and a third position L3B at which a coated portion of the metal foil 61 in which the metal foil 61 is coated with the electrode paste 62 is located. The third positions L3A and the third position L3B constitute a third position L3 at which the electrode 60 is placed.

In FIG. 8, the leading third position L3A is a leading end portion of the electrode 60 produced on the electrode production line, as viewed in the X-axis direction, and the feeding of the electrode 60 is started at the leading third position L3A. The leading end portion of the electrode 60 is an uncoated portion in which the electrode paste 62 is not applied by coating to the opposite surfaces 61a, 61b of the metal foil 61. The trailing third position L3A is a rear end portion of the electrode 60 that is fed by the feed conveyor 52, etc. toward the next step, after the start of the feeding. The rear end portion of the electrode 60, at which the feeding ends, is an uncoated portion in which the electrode paste 62 is not applied by coating to the opposite surfaces 61a, 61b of the metal foil 61.

In the meantime, the initial five pulses or so of transmitted waves US, for example, out of 30 pulses of ultrasonic waves US transmitted through the reference foil 65 and obtained by the second calibration ultrasonic sensor 22, cannot be obtained as a stable received signal. Therefore, the ultrasonic measurement control unit 5 and the thickness computing unit 40 approximate the stabilized, remaining 25 pulses or so of the transmitted waves US by sine wave, through averaging, or the like, and correct them into a sonic waveform, so as to calculate the maximum amplitude value (received signal) of the waveform approximate to sine wave.

The first calibration ultrasonic sensor 21 of the calibration ultrasonic sensor set 20 produces 30 oscillatory waves for each measurement, at the above-mentioned first position L1, and a second position at which only the air layer AR is present between the first calibration ultrasonic sensor 21 and the second calibration ultrasonic sensor 22. In the meantime, the initial five pulses or so of transmitted values, for example, out of 30 pulses of ultrasonic waves US transmitted through the reference foil 65 and obtained by the second calibration ultrasonic sensor 22, cannot be obtained as a stable received signal. Therefore, the ultrasonic measurement control unit 5 and the thickness computing unit 40 approximate the stabilized, remaining 25 pulses or so of the transmitted waves US by sine wave, through averaging, or the like, and correct them into a sonic waveform, so as to calculate the maximum amplitude value (received signal) of the waveform approximate to sine wave.

Initially, the ultrasonic measurement control unit 5 moves the calibration ultrasonic sensor set 20 to the first position L1 at which the reference foil 65 is placed, by means of the upper slide shaft 55A and the lower slide shaft 55B, and keeps the sensor set 20 stopped until time t1 is reached, after start of calculation of the basis weight. During this period, the first ultrasonic sensor 11 of the actual-measurement ultrasonic sensor set 10 produces 30 oscillatory waves, at the third position L3A where the uncoated portion of the metal foil 61 that is not coated with the electrode paste 62 is placed between the first ultrasonic sensor 11 and the second ultrasonic sensor 12. The ultrasonic measurement control unit 5 and the thickness computing unit 40 obtain the maximum amplitude value (received signal) of the above-described waveform approximate to sine wave, based on stable ones of the waves US produced by the above oscillation and transmitted through the metal foil 61. At the same time, the first calibration ultrasonic sensor 21 of the calibration ultrasonic sensor set 20 produces 30 oscillatory waves, with the reference foil 65 placed between the first calibration ultrasonic sensor 21 and the second calibration ultrasonic sensor 22. The ultrasonic measurement control unit 5 and the thickness computing unit 40 obtain the maximum amplitude value (received signal) of the above-described waveform approximate to sine wave, based on stable ones of the waves US produced by the above oscillation and transmitted through the reference foil 65.

The numerator of the above-indicated Eq. (14) can be obtained by acquiring one of the received signal based on the ultrasonic waves US transmitted through the metal foil 61 at the third position L3A, using the actual-measurement ultrasonic sensor set 10, and the received signal based on the ultrasonic waves US transmitted through the reference foil 65, using the calibration ultrasonic sensor set 20. However, by operating both of the actual-measurement ultrasonic sensor set 10 and the calibration ultrasonic sensor set 20 at the same time, as described above, so as to obtain the received signals by transmitting the ultrasonic waves US through the metal foil 61 and the reference foil 65, respectively, it can be checked if any of the ultrasonic sensors used suffers from chronological deterioration or is in a poor condition. Also, by operating both of the actual-measurement ultrasonic sensor set 10 and the calibration ultrasonic sensor set 20 so as to obtain the received signals by transmitting the ultrasonic waves US through the metal foil 61 and the reference foil 65, respectively, it is possible to grasp machine differences among the first and second ultrasonic sensors 11, 12 of the actual-measurement ultrasonic sensor set 10 and the first and second calibration ultrasonic sensors 21, 22 of the calibration ultrasonic sensor set 20, and an influence of changes in the temperature of the air layer AR through which the ultrasonic waves US propagate.

Then, at time t1, the ultrasonic measurement control unit 5 moves the upper slide shaft 55A and the lower slide shaft 55B to the negative side in the Y-axis direction (to the left, lower side in FIG. 2), until the actual-measurement ultrasonic sensor set 10 is placed at the first position L1, and keeps the sensor set 10 stopped until time t2 is reached. As a result, the calibration ultrasonic sensor set 20 leaves the first position L1, and is further moved to the left-side second position L2 in FIG. 3, and stopped.

During the period between time t1 and time t2, the calibration ultrasonic sensor set 20 carries out at least one measurement, in accordance with the actual measurement by the actual-measurement ultrasonic sensor set 10, and the first calibration ultrasonic sensor 21 emits 30 oscillatory waves for each measurement, toward the air layer AR between the first calibration ultrasonic sensor 21 and the second calibration ultrasonic sensor 22. The ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the air layer AR. On the other hand, the actual-measurement ultrasonic sensor set 10 carries out at least one measurement, and the first ultrasonic sensor 11 emits 30 oscillatory waves for each measurement, toward the reference foil 65. The ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the reference foil 65.

If there is a difference between the received signal obtained by the actual-measurement ultrasonic sensor set 10, and the received signal obtained by the calibration ultrasonic sensor set 20, the ultrasonic measurement control unit 5 and the thickness computing unit 40 cause the actual-measurement ultrasonic sensor set 10 to update the measurement condition values. Also, the ultrasonic measurement control unit 5 obtains a machine difference between the calibration ultrasonic sensor set 20 and the actual-measurement ultrasonic sensor set 10, based on the received signal as a result of measurement of the reference foil 65 by the calibration ultrasonic sensor set 20 prior to time t1, and the received signal as a result of measurement of the reference foil 65 by the actual-measurement ultrasonic sensor set 10 between time t1 and time t2.

Then, at time t2, the ultrasonic measurement control unit 5 moves the upper slide shaft 55A and the lower slide shaft 55B to the positive side in the Y-axis direction (to the right, upper side in FIG. 2), until the actual-measurement ultrasonic sensor set 10 is placed at the third position L3B, and keeps the sensor set 10 stopped until time t3 is reached. By the time when time t2 is reached after the start of calculation of the basis weight, the leading end portion (uncoated portion that is not coated with the electrode paste 62) of the electrode 60, as viewed in the X-axis direction, has already been fed to the next process step, by the feed conveyor 52, etc., and the coated portion of the electrode 60 coated with the electrode paste 62, between the leading end portion and the rear end portion at which the feeding ends, is located in the measuring unit 7 of the ultrasonic measuring system 1.

During the period between time t2 and time t3, the first calibration ultrasonic sensor 21 of the calibration ultrasonic sensor set 20 produces 30 oscillatory waves for each measurement, in accordance with the actual measurement by the actual-measurement ultrasonic sensor set 10. At the same time, the ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the reference foil 65.

On the other hand, during the period between t2 and t3, the actual-measurement ultrasonic sensor set 10 carries out a plurality of actual measurements, between the coated portion (the third position L3B) coated with the electrode paste 62, and the uncoated portion (the third position L3A) or rear end portion that is not coated with the electrode paste 62, depending on the length of the electrode 60 down to the rear end portion. For each actual measurement, the first ultrasonic sensor 11 produces 30 oscillator waves per measurement. The ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the coated portion (the third position L3B) coated with the electrode paste 62, and the uncoated portion (the third position L3A) that is not coated with the electrode paste 62.

If there is a difference between the received signal obtained by the actual-measurement ultrasonic sensor set 10 and the received signal obtained by the calibration ultrasonic sensor set 20, the ultrasonic measurement control unit 5 and the thickness computing unit 40 cause the actual-measurement ultrasonic sensor set 10 to update the measurement condition values.

Then, at time t3, the ultrasonic measurement control unit 5 moves the upper slide shaft 55A and the lower slide shaft 55B to the negative side in the Y-axis direction (to the left, lower side in FIG. 2), until the actual-measurement ultrasonic sensor set 10 is placed at the first position L1, and keeps the sensor set 10 stopped until time t4 is reached. As a result, the calibration ultrasonic sensor set 20 leaves the first position L1, and is moved to the second position L2.

During the period between time t3 and t4, the calibration ultrasonic sensor set 20 carries out at least one measurement, in accordance with the actual measurement by the actual-measurement ultrasonic sensor set 10, and the first calibration ultrasonic sensor 21 emits 30 oscillatory waves for each measurement, toward the air layer AR between the first calibration ultrasonic sensor 21 and the second calibration ultrasonic sensor 22. The ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the air layer AR.

On the other hand, the actual-measurement ultrasonic sensor set 10 carries out at least one measurement, and the first ultrasonic sensor 11 emits 30 oscillatory waves for each measurement, toward the reference foil 65. The ultrasonic measurement control unit 5 and the thickness computing unit 40 obtain the maximum amplitude value (received signal) of the above-described waveform approximate to sine wave, based on stable ones of the ultrasonic waves US produced by the above oscillation and transmitted through the reference foil 65.

If there is a difference between the received signal obtained by the actual-measurement ultrasonic sensor set 10, and the received signal obtained by the calibration ultrasonic sensor set 20, the ultrasonic measurement control unit 5 and the thickness computing unit 40 causes the actual-measurement ultrasonic sensor set 10 to update the measurement condition values. Also, the ultrasonic measurement control unit 5 obtains a machine difference between the calibration ultrasonic sensor set 20 and the actual-measurement ultrasonic sensor set 10, based on the received signal as a result of measurement of the reference foil 65 by the calibration ultrasonic sensor set 20 between time t2 and time t3, and the received signal as a result of measurement of the reference foil 65 by the actual-measurement ultrasonic sensor set 10 between time t3 and time t4.

The operations and effects of the ultrasonic measuring method and ultrasonic measuring system according to the first embodiment of the invention will be described. In the ultrasonic measuring method according to the first embodiment, at least one set of ultrasonic sensors each of which consists of the first ultrasonic sensor 11 and the second ultrasonic sensor 12 is provided, and the first ultrasonic sensor 11 is placed, via the air layer AR, on one side of the electrode 60 formed by applying the electrode paste 62 by coating to the opposite surfaces 61a, 61b of the Metal foil 61 wound in the form of a roll, as viewed in the thickness direction Z of the electrode 60, while the second ultrasonic sensor 12 is placed on the other side of the electrode 60, via the air layer AR, so that the thickness (basis weight) of the electrode paste 62 is measured by transmitting ultrasonic waves US between the first ultrasonic sensor 11 and the second ultrasonic sensor 12. In the ultrasonic measuring method, the above-indicated at least one set of ultrasonic sensors includes at least one set of actual-measurement ultrasonic sensors 10 for measuring the basis weight of the electrode paste 62, and the calibration ultrasonic sensor set 20 consisting of the first calibration ultrasonic sensor 21 and the second calibration ultrasonic sensor 22, aside from the first ultrasonic sensor 11 and the second ultrasonic sensor 12. During measurement of the thickness of the electrode paste 62, the calibration ultrasonic sensor set 20 performs calibration, and the actual-measurement ultrasonic sensor set 10 calculates the basis weight of the electrode paste 62, using the measurement condition values obtained by the calibration ultrasonic sensor set 20. Therefore, when the thickness of the electrode paste 62 is measured on the production line on which the electrode 60 is produced by coating the metal foil 61 with the electrode paste 62, in the battery production process, error factors of the measurement accuracy due to self-heating of the ultrasonic sensors and changes in the temperature of the air layers AR can be excluded or eliminated, and the thickness of the electrode paste 62 can be measured with improved accuracy.

Namely, in the ultrasonic measuring method of the first embodiment, the calibration ultrasonic sensor set 20 performs calibration, and the actual-measurement ultrasonic sensor set 10 calculates the basis weight of the electrode paste 62, using the measurement condition values obtained form the calibration ultrasonic sensor set 20, in real time during the actual measurement of the basis weight of the electrode paste 62.

Here, the relationship between the ultrasonic sensors (the first ultrasonic sensor 11, the second ultrasonic sensor 12, the first calibration ultrasonic sensor 21, and the second calibration ultrasonic sensor 22), and the sound velocity, density, and acoustic impedance in the air layer AR will be briefly described. The sound velocity, density, and acoustic impedance in the air layer are determined according to the following equations.

$$\text{Sound Velocity } C = f \times \lambda \tag{1}$$

where $C$ is the sound velocity (m/sec), $f$ is the frequency of the ultrasonic sensor kHz), and $\lambda$ is the wavelength (m).
The sound velocity may also be expressed by:

$$C = 331.5 + (0.61 \times t) \tag{2}$$

where $t$ is the temperature (° C.).

$$\text{Density } \rho = 1.293 \times (273.15/(273.15+t)) \times (P/10130.25) \tag{3}$$

where $\rho$ is the density (kg/m$^3$) (ntp), $t$ is the temperature (° C.), and $P$ is the atmospheric pressure (atm).

$$\text{Acoustic Impedance } Z = \rho \times C \tag{4}$$

where $Z$ is the acoustic impedance (Pa·s/m).
Under the atmospheric pressure, the sound velocity, density, and acoustic impedance in the air layer AR vary with the temperature of the air layer AR, as indicated in Eq. (2) through Eq. (4). If the frequency f is regarded as a constant in Eq. (1), the wavelength $\lambda$ also varies with the temperature of the air layer AR.

As in the ultrasonic measuring system as described in JP 2008-102160 A, ultrasonic waves are transmitted, via the air layer AR, between the first ultrasonic sensor 11 and the second ultrasonic sensor 12. However, in the ultrasonic measuring method of the first embodiment, the actual-measurement ultrasonic sensor set 10 adopts measurement condition values, such as the sound velocity, density, and acoustic impedance in the air layer AR, and the wavelength of transmitted ultrasonic waves US, which vary as parameters with changes in the temperature of the air layer AR, from the calibration ultrasonic sensor set 20, in real time during calculation of the basis weight of the electrode paste 62. Therefore, even if the temperature of the air layer AR between the first ultrasonic sensor 11 and the second ultrasonic sensor 12 changes during measurement, the actual-measurement ultrasonic sensor set 10 is able to calculate the basis weight of the electrode paste 62, based on the wavelength corresponding to the actual temperature during actual measurement, as described above, under the measurement condition values corrected in the calibration ultrasonic sensor set 20.

Figure 25:
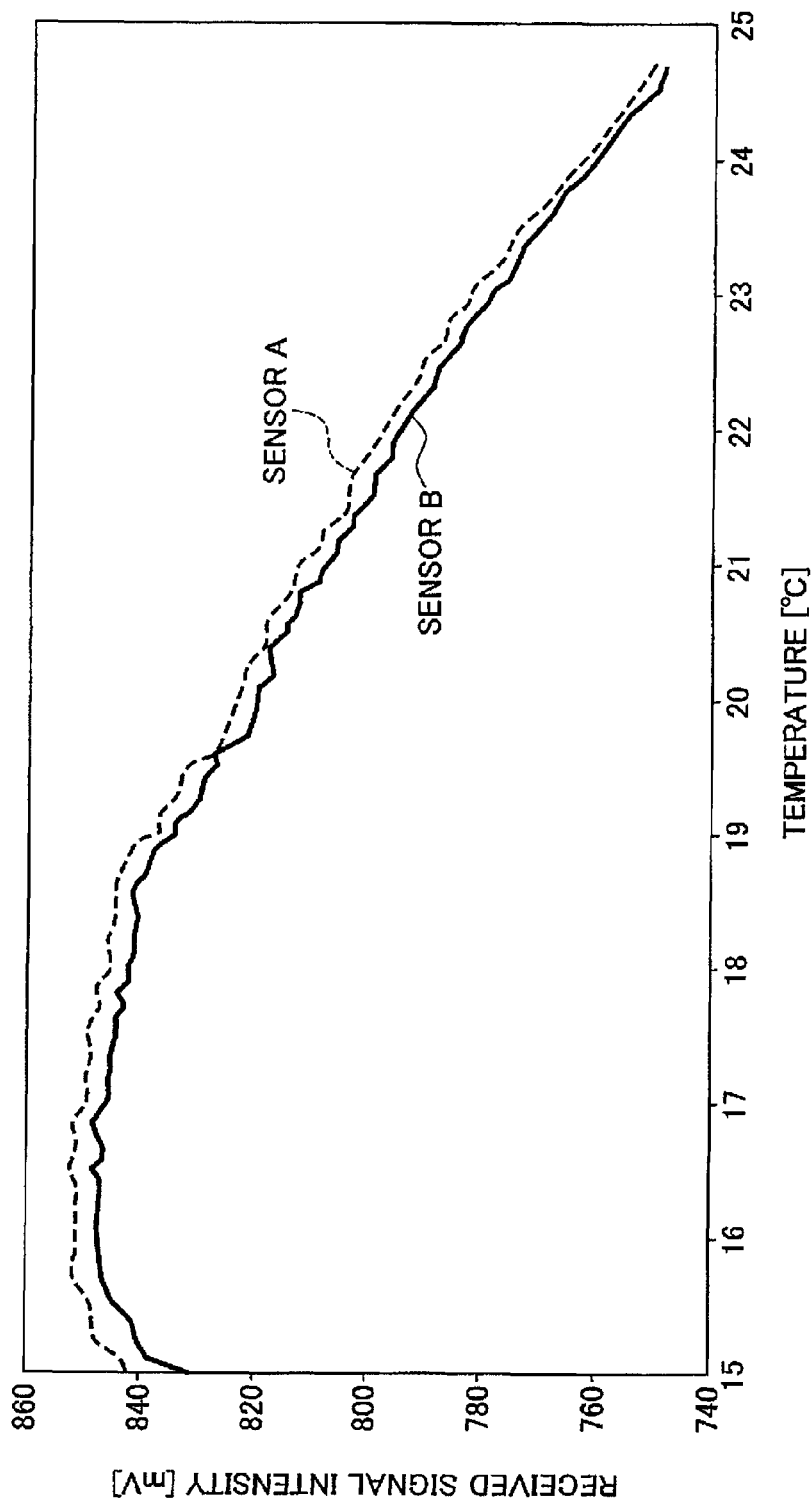
FIG. 25 is a graph indicating test results on the relationship between the intensity of a received signal received by a receiving-side ultrasonic sensor of the related art, and the temperature of the atmosphere.
Figure 26:
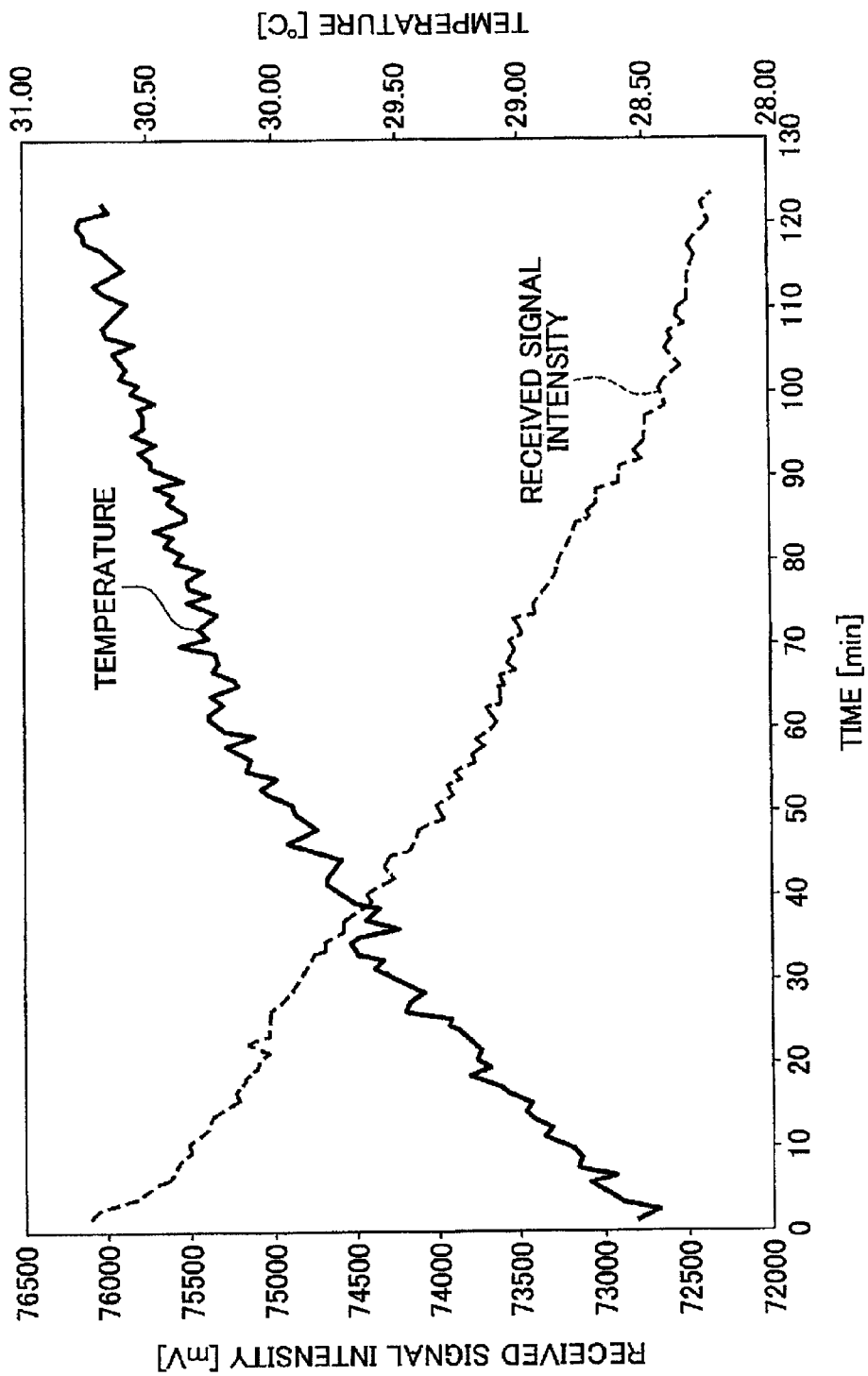
FIG. 26 is a graph indicating the relationship between self-heating and the ultrasonic intensity, in the receiving-side ultrasonic sensor of the related art.

In the ultrasonic measuring method of the related art in which calibration is not performed at the same time as the actual ultrasonic measurement, even if the same receiving-side ultrasonic sensor is used, the wavelength of ultrasonic waves received by the sensor differs as the temperature of the atmosphere (the air layer AR) of the ultrasonic sensor varies, or due to self-heating of the sensor, as indicated in FIG. 25 and FIG. 26, and the ultrasonic measurement cannot be made with high accuracy. On the other hand, in the ultrasonic measuring method of the first embodiment, the actual-measurement ultrasonic sensor set 10 actually measures the basis weight of the electrode paste 62, while adopting the measurement condition values obtained by the calibration ultrasonic sensor set 20, in real time during calculation of the basis weight of the electrode paste 62. Thus, there is no difference in the temperature of the air layer AR, between the time when the actual measurement is performed by the first and second ultrasonic sensors 11, 12, and the time when calibration is performed by the first and second calibration ultrasonic sensors 21, 22.

With the first and second ultrasonic sensors 11, 12 and the first and second calibration ultrasonic sensors 21, 22 operating in the same timing, even if the first and second ultrasonic sensors 11, 12 are self-heated with a lapse of the operating time, the first and second calibration ultrasonic sensors 21, 22 are also self-heated in the same fashion as the first and second ultrasonic sensors 11, 12. In this case, there are almost no differences between the temperatures of the self-heated first and second ultrasonic sensors 11, 12, and the temperatures of the self-heated first and second calibration ultrasonic sensors 21, 22. Therefore, even if the wavelength of ultrasonic waves US received by the calibration ultrasonic sensor set 20 changes due to self-heating, the wavelength of ultrasonic waves US received by the actual-measurement ultrasonic sensor set 10 also changes in the same manner as that of the calibration ultrasonic sensor set 20. Thus, there arises almost no difference between the wavelength of the actual-measurement ultrasonic sensor set 10 and the wavelength of the calibration ultrasonic sensor set 20, and the ultrasonic measurement can be performed with higher accuracy even when the first and second calibration ultrasonic sensors 21, 22 of the calibration ultrasonic sensor set 20 and the first and second ultrasonic sensors 11, 12 of the actual-measurement ultrasonic sensor set 10 are both self-heated.

Thus, according to the ultrasonic measuring method of the first embodiment of the invention, error factors of the measurement accuracy due to self-heating of the ultrasonic sensors and changes in the temperature of the air layer can be excluded or eliminated, so that the basis weight (thickness) of the electrode paste 62 applied by coating to the electrode 60 produced on the production line can be advantageously measured on the production line with high accuracy.

Flat-type ultrasonic sensors that permit propagation of unfocused ultrasonic waves US are used as the first calibration ultrasonic sensor 21 and second calibration ultrasonic sensor 22 of the calibration ultrasonic sensor set 20, and flat-type ultrasonic sensors that permit propagation of unfocused ultrasonic waves US are used as the first ultrasonic sensor 11 and second ultrasonic sensor 12 of the actual-measurement ultrasonic sensor set 10. With this arrangement, the receiving-side ultrasonic sensor that receives ultrasonic waves US, as one of the first ultrasonic sensor 11 and the second ultrasonic sensor 12 of the actual-measurement ultrasonic sensor set 10, provides a received signal for determining the basis weight (thickness) of the electrode paste 62, over a wider region or range of the electrode 60, as compared with a spot-type ultrasonic sensor that permits propagation of focused ultrasonic waves to within a local or narrow region. Therefore, quality check regarding the thickness of the electrode paste 62, such as the basis weight and coating profile of the electrode paste 62, can be carried out on the production line of the electrode 60.

Since the received signal received by the receiving-side ultrasonic sensor can be obtained from a wide range of the coated product, the thickness of the electrode paste 62 over a wide range of the electrode 60 can be detected; therefore, variations in the thickness of the electrode paste 62 within the measurement range can be grasped with improved accuracy, and the overall thickness of the electrode paste 62, such as the basis weight of the electrode paste 62, within a given range of the electrode 60 can be measured with high reliability.

All of the first calibration ultrasonic sensor 21 and second calibration ultrasonic sensor 22 of the calibration ultrasonic sensor set 20, and the first ultrasonic sensor 11 and second ultrasonic sensor 12 of the actual-measurement ultrasonic sensor set 10 are flat-type ultrasonic sensors. Therefore, no differences in characteristics due to differences in the forms of the ultrasonic vibration surfaces 11*a*, 12*a*, 21*a*, 22*a* of the ultrasonic sensors appear between the calibration ultrasonic sensor set 20 and the actual-measurement ultrasonic sensor set 10, and the actual-measurement ultrasonic sensor set 10 can acquire the measurement condition values obtained through calibration by the calibration ultrasonic sensor set 20, with high accuracy, in an appropriate condition.

In the ultrasonic measuring method of the first embodiment, the first ultrasonic sensor 11, second ultrasonic sensor 12, first calibration ultrasonic sensor 21, and second calibration ultrasonic sensor 22 preferably have nominal frequencies that are in the same frequency band. Also, ultrasonic sensors capable of sending and receiving ultrasonic waves US are preferably used as the first ultrasonic sensor 11 and the second ultrasonic sensor 12, and the first calibration ultrasonic sensor 21 and the second calibration ultrasonic sensor 22.

Prior to the actual measurement by the actual-measurement ultrasonic sensor set 10, the reference foil 65 used for calibration is placed between the first calibration ultrasonic sensor 21 and the second calibration ultrasonic sensor 22 of the calibration ultrasonic sensor set 20, and ultrasonic waves US sent from the first calibration ultrasonic sensor 21 are transmitted through the reference foil 65, so that the first received signal $S_K$ of the ultrasonic waves US received by the second calibration ultrasonic sensor 22 is obtained in advance as a measurement condition value. The actual-measurement ultrasonic sensor set 10 obtains the second received signal $S_X$ of ultrasonic waves US transmitted through the electrode 60 between the first ultrasonic sensor 11 and the second ultrasonic sensor 12, and the thickness of the electrode paste 62 of the electrode 60 is calculated based on the relative ratio of the first received signal $S_K$ and the second received signal $S_X$. Therefore, when the thickness of the electrode paste 62, such as the basis weight and coating profile of the electrode paste 62, is measured, with respect to the electrode 60 formed by coating the metal foil 61 with the electrode paste 62, the basis weight of the electrode paste 62 can be easily calculated according to the above-indicated Eq. (14), only by obtaining the second received signal $S_X$, without requiring a calibration curve (see FIG. 12) indicating the relationship between the attenuation factor of ultrasonic waves US transmitted through the electrode paste 62 and the basis weight of the electrode paste 62, during the actual measurement of the thickness of the electrode paste 62, if the basis weight $M_A$ of the reference foil 65 used for calibration, and the first received signal $S_K$, are obtained in advance, prior to the actual measurement by the actual-measurement ultrasonic sensor set 10.

The actual-measurement ultrasonic sensor set 10 is moved to the position at which the reference foil 65 is placed, and ultrasonic waves US sent from the first ultrasonic sensor 11 are transmitted through the reference foil 65, so that the actual-measurement ultrasonic sensor set 10 obtains the third received signal $S_Y$ of the ultrasonic waves US received by the second ultrasonic sensor 12. Therefore, when there is a machine difference between the first calibration ultrasonic sensor 21 and second calibration ultrasonic sensor 22 of the calibration ultrasonic sensor set 20, and the first ultrasonic sensor 11 and second ultrasonic sensor 12 of the actual-measurement ultrasonic sensor set 10, the machine difference between the calibration ultrasonic sensor set 20 and the actual-measurement ultrasonic sensor set 10 can be grasped from the relative ratio of the first received signal $S_X$ and the third received signal $S_Y$. Accordingly, if the actual-measurement ultrasonic sensor set 10 calculates the basis weight of the electrode paste 62 in view of the machine difference from the calibration ultrasonic sensor set 20, based on the first received signal $S_X$ and the third received signal $S_Y$, error factors due to the machine difference between the calibration ultrasonic sensor set 20 and the actual-measurement ultrasonic sensor set 10 can be excluded or eliminated, and the basis weight of the electrode paste 62 can be calculated with high accuracy.

Since the first calibration ultrasonic sensor 21 and the second calibration ultrasonic sensor 22, and the first ultrasonic sensor 11 and the second ultrasonic sensor 12, send and receive ultrasonic waves US in synchronization with each other, the calibration ultrasonic sensor set 20 and the actual-measurement ultrasonic sensor set 10 can be exposed to an environment having the same atmosphere temperature with no time difference, and the sound velocity, density, and acoustic impedance in the air layers AR can be made substantially equal in the calibration ultrasonic sensor set 20 and the actual-measurement ultrasonic sensor set 10. With this arrangement, the ultrasonic waves US transmitted between the first calibration ultrasonic sensor 21 and the second calibration ultrasonic sensor 22 of the calibration ultrasonic sensor set 20, and the ultrasonic waves US transmitted between the first ultrasonic sensor 11 and the second ultrasonic sensor 12 of the actual-measurement ultrasonic sensor set 10 are transmitted through the air layers AR, under substantially the same conditions. Accordingly, the actual-measurement ultrasonic sensor set 10 acquires measurement condition values from the calibration ultrasonic sensor set 20, as highly accurate, correction values from which error factors due to the atmosphere temperature and self-heating are excluded, under the same conditions as the calibration ultrasonic sensor set 20, so that the basis weight of the electrode paste 62 can be calculated with high accuracy in a stable condition.

In the ultrasonic measuring system 1 having at least one set of ultrasonic sensors each of which consists of the first ultrasonic sensor 11 and the second ultrasonic sensor 12, the first ultrasonic sensor 11 is placed, via the air layer AR, on one side of the electrode 60 formed by applying the electrode paste 62 by coating to one surface or both surfaces of the metal foil 61 wound in the form of a roll, as viewed in the thickness direction Z of the electrode 60, while the second ultrasonic sensor 12 is placed on the other side of the electrode 60, via the air layer AR. The ultrasonic measuring system 1 measures the thickness (basis weight) of the electrode paste 62, by transmitting ultrasonic waves US between the first ultrasonic sensor 11 and the second ultrasonic sensor 12. In the ultrasonic measuring system 1, the above-indicated at least one set of ultrasonic sensors includes at least one set of actual-measurement ultrasonic sensors 10 for measuring the thickness of the electrode paste 62, and the calibration ultrasonic sensor set 20 consisting of the first calibration ultrasonic sensor 21 and the second calibration ultrasonic sensor 22, aside from the first ultrasonic sensor 11 and the second ultrasonic sensor 12. During measurement of the basis weight of the electrode paste 62, the actual-measurement ultrasonic sensor set 10 sends and receives ultrasonic waves US, based on the measurement condition values obtained through calibration by the calibration ultrasonic sensor set 20. Therefore, when the thickness of the electrode paste 62 is measured on the production line on which the electrode 60 is produced by coating the metal foil 61 with the electrode paste 62, in the battery production process, error factors of the measurement accuracy due to self-heating of the ultrasonic sensors and changes in the temperature of the air layer AR are excluded or eliminated, during the actual measurement, and the thickness of the electrode paste 62 can be measured with high accuracy.

With the first and second ultrasonic sensors 11, 12 and the first and second calibration ultrasonic sensors 21, 22 operating in the same timing, even if the first and second ultrasonic sensors 11, 12 are self-heated with a lapse of the operating time, the first and second calibration ultrasonic sensors 21, 22 are also self-heated in the same fashion as the first and second ultrasonic sensors 11, 12. In this case, there is almost no difference between the temperatures of the self-heated first and second ultrasonic sensors 11, 12 and the temperatures of the self-heated first and second calibration ultrasonic sensors 21, 22. Therefore, even if the wavelength of ultrasonic waves US received by the calibration ultrasonic sensor set 20 changes due to self-heating, the wavelength of the received ultrasonic waves US in the actual-measurement ultrasonic sensor set 10 also changes in the same manner as that of the calibration ultrasonic sensor set 20. Thus, there arises almost no difference between the wavelength of the actual-measurement ultrasonic sensor set 10 and the wavelength of the calibration ultrasonic sensor set 20, and the thickness of the electrode paste 62 can be measured, assuring high measurement accuracy, even if the first and second calibration ultrasonic sensors 21, 22 of the calibration ultrasonic sensor set 20 and the first and second ultrasonic sensors 11, 12 of the actual-measurement ultrasonic sensor set 10 are both self-heated.

Thus, in the ultrasonic measuring system 1 of the first embodiment, error factors of the measurement accuracy due to self-heating of the ultrasonic sensors and changes in the temperature of the air layer AR can be excluded or eliminated, so that the thickness (basis weight) of the electrode paste 62 applied by coating to the electrode 60 produced on the production line can be advantageously measured on the production line with high accuracy.

In the ultrasonic measuring system 1 of the first embodiment, the production line for producing the electrode 60 need not be stopped, and the actual-measurement ultrasonic sensor set 10 can acquire measurement condition values obtained through calibration by the calibration ultrasonic sensor set 20, during operation of the line. Therefore, an extra or additional step for correcting measurement conditions of the actual-measurement ultrasonic sensor set 10 is not required, and the cost for production of the electrode 60 will not be increased. Also, the ultrasonic measuring system 1 of the first embodiment is installed on the production line at a low cost, and can be easily incorporated into the production line for producing the electrode 60, no matter whether the system is newly installed or has already been installed.

Flat-type ultrasonic sensors that permit propagation of unfocused ultrasonic waves US are used as the first calibration ultrasonic sensor 21 and second calibration ultrasonic sensor 22 of the calibration ultrasonic sensor set 20, and flat-type ultrasonic sensors that permit propagation of unfocused ultrasonic waves US are used as the first ultrasonic sensor 11 and second ultrasonic sensor 12 of the actual-measurement ultrasonic sensor set 10. When the thickness (basis weight) of the electrode paste 62 is measured on the production line on which the electrode 60 is produced by coating the metal foil 61 with the electrode paste 62, in the battery production process, a wide area of the electrode 60 is irradiated with ultrasonic waves US sent from the first ultrasonic sensor 11 so that the ultrasonic waves US are transmitted through the metal foil 61 and electrode paste 62 of the electrode 60, and the second ultrasonic sensor 12 can receive the ultrasonic waves (transmitted waves) US transmitted through wider ranges of the metal foil 61 and the electrode paste 62.

Since the received signal representing the transmitted waves US received by the Second ultrasonic sensor 12 can be obtained from a wide range of the electrode 60, as the received signal (second received signal $S_x$) for determining the thickness of the electrode paste 62, the thickness of the electrode paste 62 over a wide range of the electrode 60 can be detected. Accordingly, variations in the thickness of the electrode paste 62 within the measurement range can be grasped with improved accuracy, and the overall thickness of the electrode paste 62, such as the basis weight of the electrode paste 62, within a given range of the electrode 60 can be measured with high reliability.

All of the first calibration ultrasonic sensor 21 and second calibration ultrasonic sensor 22 of the calibration ultrasonic sensor set 20, and the first ultrasonic sensor 11 and second ultrasonic sensor 12 of the actual-measurement ultrasonic sensor set 10 are flat-type ultrasonic sensors. Therefore, no differences in characteristics due to differences in the forms of the ultrasonic vibration surfaces 11a, 12a, 21a, 22a of the ultrasonic sensors appear between the calibration ultrasonic sensor set 20 and the actual-measurement ultrasonic sensor set 10, and the measurement condition values obtained through calibration by the calibration ultrasonic sensor set 20 can be appropriately and accurately fed back to the actual-measurement ultrasonic sensor set 10.

The ultrasonic measuring system 1 includes the ultrasonic measurement control unit 5 that controls sending and receiving of ultrasonic waves US and measurement conditions, in the calibration ultrasonic sensor set 20 and the actual-measurement ultrasonic sensor set 10. Since the ultrasonic measurement control unit 5 feeds back the measurement condition values obtained by the calibration ultrasonic sensor set 20, to the actual-measurement ultrasonic sensor set 10, the actual-measurement ultrasonic sensor set 10 can constantly acquire the latest measurement condition values resulting from calibration by the calibration ultrasonic sensor set 20, in accordance with changes in the measurement environment, in real time during calculation of the basis weight of the electrode paste 62, and the basis weight of the electrode paste 62 can be calculated with high accuracy.

In the ultrasonic measuring method of the related art in which calibration is not carried out at the same time as the actual ultrasonic measurement, there is a time difference between calibration performed earlier and calibration performed later, and increases in the temperatures of the ultrasonic sensors due to self-heating, and changes in measurement environments, such as the atmosphere temperature and the density of the air layer, often take place within the time. Even if the thickness of the coating material is measured with the ultrasonic sensors while the measurement environments are changing, the measurement results vary due to the changes in the measurement environments, resulting in measurement values having low or no reliability. On the other hand, the ultrasonic measuring system 1 of the first embodiment can measure the thickness of the electrode paste 62 by constantly adopting the latest measurement condition values, in accordance with changes in the measurement environments; therefore, the calculation results of the basis weight of the electrode paste 62 provide measurement values having high accuracy and high reliability.

The reference foil 65 used for calibration is placed along with the electrode 60, and the calibration ultrasonic sensor set 20 is movable at least within a range between the first position L1 at which the reference foil 65 is placed, and the second position L2 at which only the air layer AR is present between the calibration first ultrasonic sensor 21 and the calibration second ultrasonic sensor 22. With the calibration ultrasonic sensor set 20 moving between the first position L1 and the second position L2, the received signal $S_K$ (in the presence of the foil) of ultrasonic waves transmitted through the reference foil 65 placed between the first calibration ultrasonic sensor 21 and the second calibration ultrasonic sensor 22 and received can be obtained at the first position L1, and the no-foil received signal $S_C$ can be obtained at the second position L2, as described above. With this arrangement, even if changes in the measurement environments, such as the temperature of the atmosphere in which calibration is performed, and the density of the air layer AR, and/or increases in the temperatures of the ultrasonic sensors due to self-heating, take place, the calibration ultrasonic sensor set 20 moves between the first position L1 and the second position L2, so as to constantly obtain the received signal $S_K$ in the presence of the foil and the no-foil received signal $S_C$, which are required for obtaining the attenuation factor α of ultrasonic waves US transmitted through the reference foil 65. Thus, when the thickness of the electrode paste 62 of the electrode 60 is actually measured, the optimum attenuation factor α can be obtained in accordance with changes in the measurement environments.

The actual-measurement ultrasonic sensor set 10 is movable at least within a range between the first position L1, and the third position L3A, L3B at which the electrode 60 is placed. Each time the actual-measurement ultrasonic sensor set 10 moves between the first position L1 and the third position L3A, L3B, the latest machine difference between the actual-measurement ultrasonic sensor set 10 and the calibration ultrasonic sensor set 20 that performs calibration using the reference foil 65 that is "true" can be taken into or fed to the actual-measurement ultrasonic sensor set 10. Therefore, even if changes in the measurement environments, such as the temperature of the atmosphere in which the thickness of the electrode paste 62 is measured, and the density of the air layer AR, and/or increases in the temperatures of the ultrasonic sensors due to self-heating, take place, error factors due to the machine difference from the calibration ultrasonic sensor set 20 can be excluded with increased reliability.

The metal foil 61 wound in the form of a roll has a large length, and the reference foil 65 and the electrode 60 are arranged side by side in the width direction Y of the metal foil 61, which is perpendicular to the longitudinal direction X parallel to the long sides of the metal foil 61 and the thickness direction Z of the metal foil 61. Since the calibration ultrasonic sensor set 20 and the actual-measurement ultrasonic sensor set 10 move in a direction parallel to the width direction Y, the calibration ultrasonic sensor set 20 and the actual-measurement ultrasonic sensor set 10 are arranged to move on the same pair of upper slide shaft 55A and lower slide shaft 55B, such that the calibration ultrasonic sensor set 20 and the actual-measurement ultrasonic sensor set 10 move in synchronization with each other, relative to the upper slide shaft 55A and the lower slide shaft 55B. With this arrangement, the calibration ultrasonic sensor set 20 moves between the first position L1 and the second position L2 at the same time that the actual-measurement ultrasonic sensor set 10 moves between the first position L1 and the third position L3A, L3B. Thus, both the calibration ultrasonic sensor set 20 and the actual-measurement ultrasonic sensor set 10 are able to change setting of measurement conditions according to measurement environments, such as the atmosphere temperature and the density of the air layer AR, with no loss of time and high efficiency.

Figure 13:
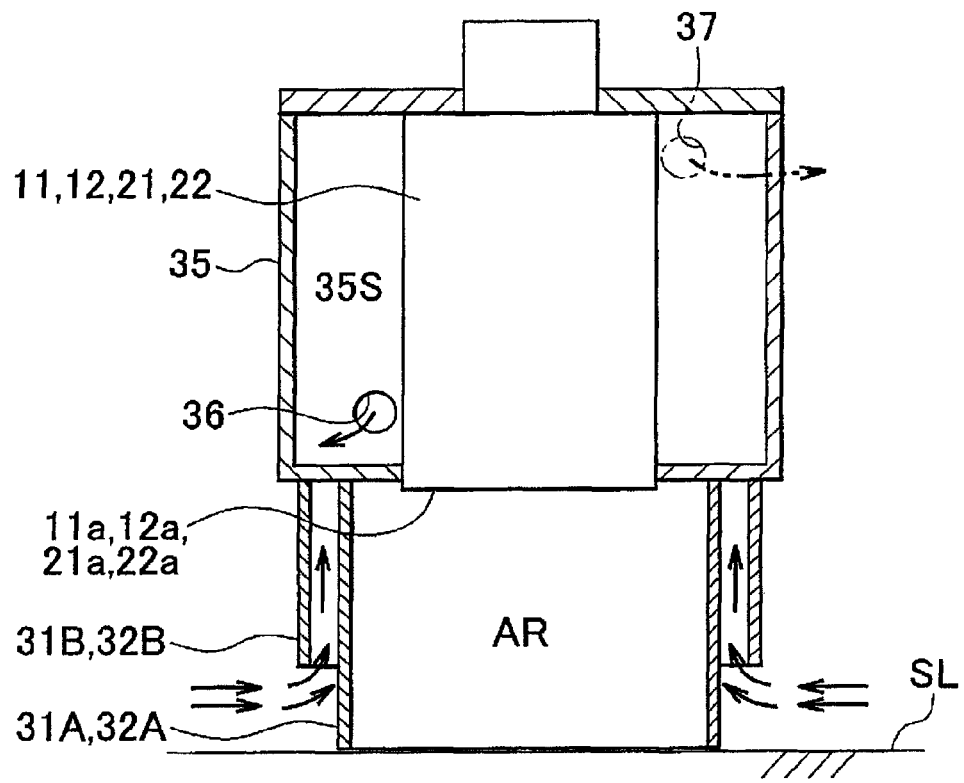
FIG. 13 is a schematic view useful for explaining the operation of a cover of the ultrasonic measuring system according to the first embodiment of FIG. 1.
Figure 14:
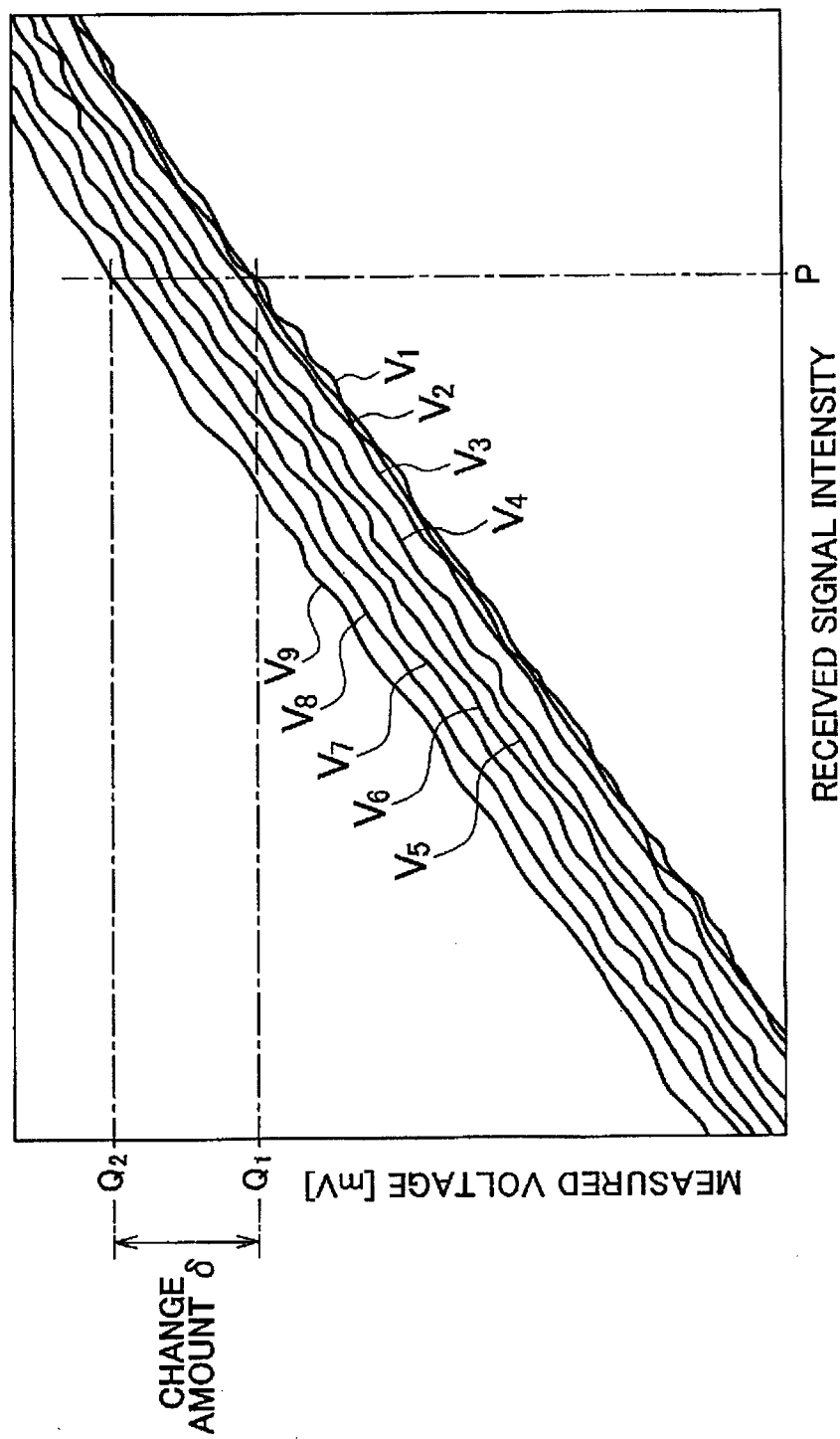
FIG. 14 is a graph indicating, as one example, test results regarding an influence of convection (flow of air) in an air layer, on the intensity of ultrasonic waves received, in the first embodiment.

FIG. 13 is a schematic view useful for explaining the operation of the cover of the ultrasonic measuring system. FIG. 14 is a graph indicating, as one example, test results regarding an influence of convention of air in the air layer on the intensity of ultrasonic waves received. The test used nine samples of ultrasonic waves received, and measured voltages at respective received signal intensities P of the ultrasonic waves V1 through V9 were checked when the convection (air flow) velocity in the air layer through which the ultrasonic waves V1 through V9 are transmitted was 0.1 (m/sec.). As a result, when convection occurs in the air layer at the velocity of 0.1 (m/sec.), an amount of change or variation δ appears between a measured voltage value Q2 of the ultrasonic waves V9 having the largest measured voltage, and a measured voltage value Q1 of the ultrasonic waves V3 having the smallest measured voltage, as shown in FIG. 14. The amount of change δ is such that the absolute value of the measured voltage value Q1 corresponds to about a half of the absolute value of the measured voltage value Q2, and it is thus understood that the ultrasonic intensity is greatly influenced by the convention (flow) of air in the air layer.

In the ultrasonic measuring system 1 of the first embodiment, on the other hand, each of the first calibration ultrasonic sensor 21 and the second calibration ultrasonic sensor 22 of the calibration ultrasonic sensor set 20 is provided with the cylindrical calibration sensor cover 32 that surrounds the air layer AR between the ultrasonic vibration surface 21a, 22a and the reference foil 65. Therefore, during execution of calibration, error factors due to an influence of convection (flow of air) in the air layer AR, including, for example, changes in the density, changes in the temperature, changes in the acoustic impedance, the directionality of transmitted ultrasonic waves US, and interference with sound waves transmitted as noise from the outside, in the air layer AR between the ultrasonic vibration surface 21a, 22a and the reference foil 65, are excluded or eliminated, and the measurement condition values as reference values can be set with improved accuracy.

In the ultrasonic measuring system 1 of this embodiment, each of the first ultrasonic sensor 11 and the second ultrasonic sensor 12 of the actual-measurement ultrasonic sensor set 10 is provided with the cylindrical actual-measurement sensor cover 31 that surrounds the air layer AR between the ultrasonic vibration surface 11a, 12a and the electrode 60. Therefore, during actual measurement of the thickness of the electrode paste 62, error factors due to an influence of convection (flow of air) in the air layer AR, including, for example, changes in the density, changes in the temperature, changes in the acoustic impedance, the directionality of transmitted ultrasonic waves US, and interference with sound waves transmitted as noise from the outside, in the air layer AR between the ultrasonic vibration surface 11a, 12a and the electrode 60, are excluded, and the thickness of the electrode paste 62 can be measured with improved accuracy.

The calibration sensor covers 32 and the actual-measurement sensor covers 31 has a dual structure consisting of the inner cylindrical cover 31A, and the outer cylindrical cover 31B located radially outwardly of the inner cylindrical cover 31A. The outer cylindrical cover 31B is formed to be shorter than the inner cylindrical cover 31A as measured in the direction (Z-axis direction) parallel to the direction of the thickness of the metal foil 61, so that the outer cylindrical cover 31B is spaced by a larger distance from the reference foil 65 and the electrode 60 than the inner cylindrical cover 31A. Therefore, even if air that flows outside the calibration sensor cover 32 hits against the calibration sensor cover 32 in the vicinity of the surface SL of the reference foil 65, as shown in FIG. 13, the flow of the air is changed by the inner cylindrical cover 31A, and the air flows between the outer cylindrical cover 31B and the inner cylindrical cover 31A, so that air turbulence is less likely or unlikely to occur in the vicinity of the surface SL of the reference foil 65. Therefore, even if there is a slight clearance between the inner cylindrical cover 31A and the reference foil 65, air that flows through the small clearance is hardly influenced by the turbulence, and the air layer AR between the ultrasonic vibration surface 21a, 22a and the reference foil 65 can be kept in a stable condition.

Also, even if air that flows outside the actual-measurement sensor cover 31 hits against the actual-measurement sensor cover 31 in the vicinity of the surface SL of the electrode 60, as shown in FIG. 13, the flow of the air is changed by the inner cylindrical cover 31A, and the air flows between the outer cylindrical cover 31B and the inner cylindrical cover 31A, so that air turbulence is less likely or unlikely to occur in the vicinity of the surface SL of the electrode 60. Therefore, even if there is a slight clearance between the inner cylindrical cover 31A and the electrode 60, air that flows through the small clearance is hardly influenced by the turbulence, and the air layer AR between the ultrasonic vibration surface 11a, 12a and the electrode 60 can be kept in a stable condition.

In the ultrasonic measuring system of the illustrated embodiment, the substrate is the metal foil 61 used in the electrode 60 of the battery as the coated product, and the coating material is the electrode paste 62 applied by coating to the metal foil 61. In the battery production process, quality check regarding the basis weight of the electrode paste 62 can be conducted over a wide range of the electrode 60, on the production line for producing the electrode 60 by coating the metal foil 61 with the electrode paste 62, during operation of the line. Furthermore, the quality check can be performed on all of the electrodes produced on the line, so that high-quality, high-performance batteries can be provided.

Next, an ultrasonic measuring method and an ultrasonic measuring system according to a second embodiment of the invention will be described. In the first embodiment, the ultrasonic measuring system 1 is constructed such that the reference foil 65 is placed while being fixed in position. In operation, ultrasonic waves US sent from the first calibration ultrasonic sensor 21 are transmitted through one region of the fixed reference foil 65, and a signal of the ultrasonic waves US received by the second calibration ultrasonic sensor 22 is obtained as the first received signal $S_K$. Also, ultrasonic waves US sent from the first ultrasonic sensor 11 are transmitted through one region of the fixed reference foil 65, and a signal of the ultrasonic waves US received by the second ultrasonic sensor 12 is obtained as the third received signal $S_Y$. The frequency bands of the first ultrasonic sensor 11, second ultrasonic sensor 12, first calibration ultrasonic sensor 21, and the second calibration ultrasonic sensor 22 are controlled to be within the range of 100 to 250 KHz. Also, the actual-measurement ultrasonic sensor set 10 is provided with the actual-measurement sensor cover 31, and the calibration ultrasonic sensor set 20 is provided with the calibration sensor cover 32.

In the second embodiment, on the other hand, the ultrasonic measurement system 201 is provided with a mechanism for rotating the reference foil 65. In operation, the first received signal $S_K$ is obtained by performing a computation on five first sample received signals $S_{K1}$-$S_{K5}$ of ultrasonic waves US sent from a first calibration ultrasonic sensor 221, transmitted through five regions of the rotating reference foil 65, and received by a second calibration ultrasonic sensor 222. Also, the third received signal $S_Y$ is obtained by performing a computation on five third sample received signals $S_{Y1}$-$S_{Y5}$ of ultrasonic waves US sent from a first ultrasonic sensor 211, transmitted through five regions of the rotating reference foil 65, and received by a second ultrasonic sensor 212. The frequency bands of the first ultrasonic sensor 211, second ultrasonic sensor 212, first calibration ultrasonic sensor 221, and the second calibration ultrasonic sensor 222 are around 40 KHz. Also, an actual-measurement ultrasonic sensor unit 210 is not provided with any actual-measurement sensor cover, and a calibration ultrasonic sensor unit 220 is not provided with any calibration sensor cover.

Namely, the second embodiment is difference from the first embodiment in that the reference foil 65 is rotated, the first received signal $S_K$ is obtained based on the five first sample received signals $S_{K1}$-$S_{K5}$, the third received signal $S_Y$ is obtained based on the five third sample received signals $S_{Y1}$-$S_{Y5}$, the frequency bands of both of the actual-measurement ultrasonic sensor set 210 and the calibration ultrasonic sensor set 220 are around 40 KHz, and that the actual-measurement sensor cover and calibration sensor cover are not provided. The other portions or arrangements of the second embodiment are substantially identical with those of the first embodiment. Accordingly, the second embodiment will be described mainly with respect to its portions different from those of the first embodiment, and description of the other portions will be simplified or omitted.

Figure 16:
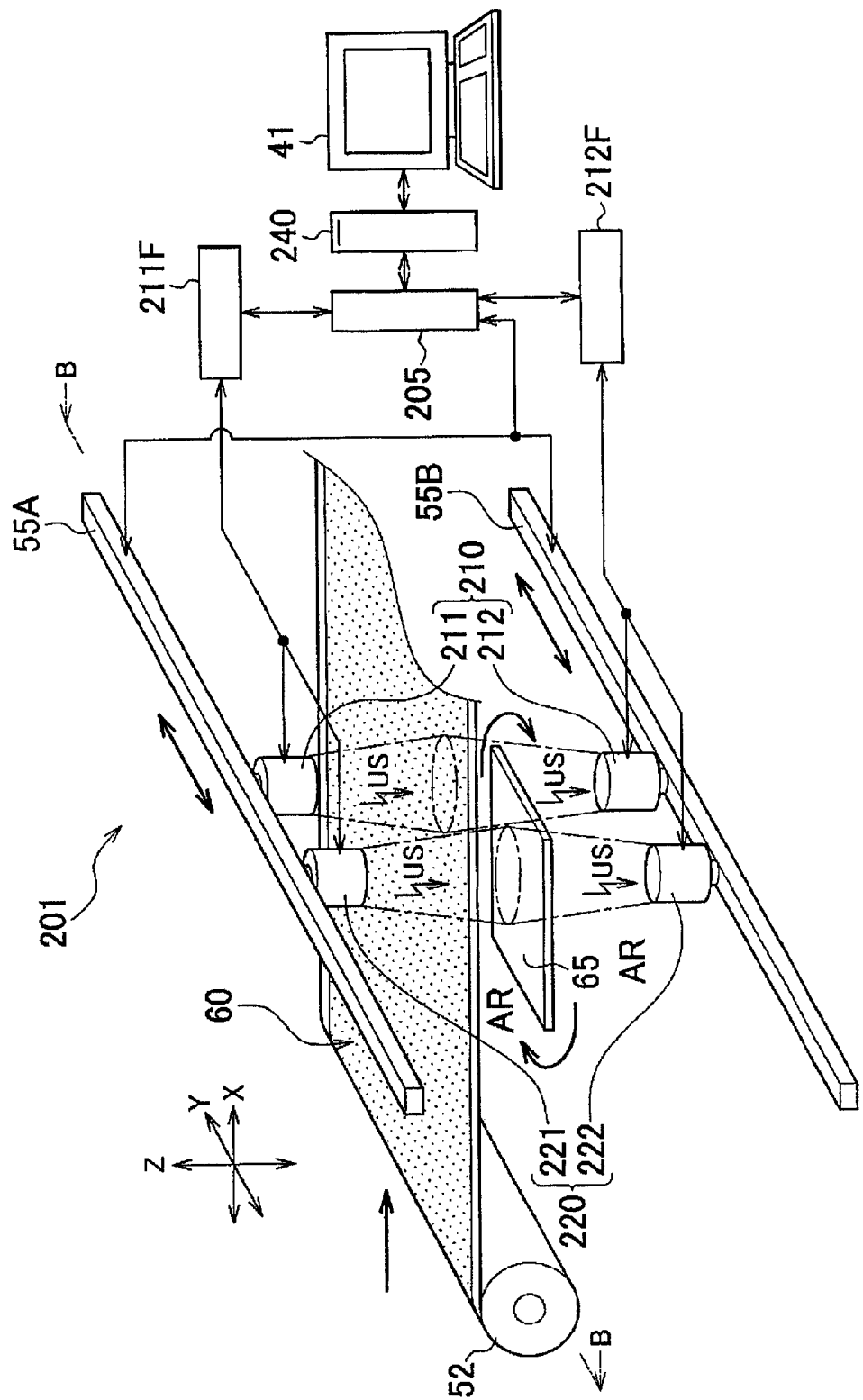
FIG. 16 is a perspective view schematically showing an ultrasonic measuring system according to a second embodiment of invention.
Figure 17:
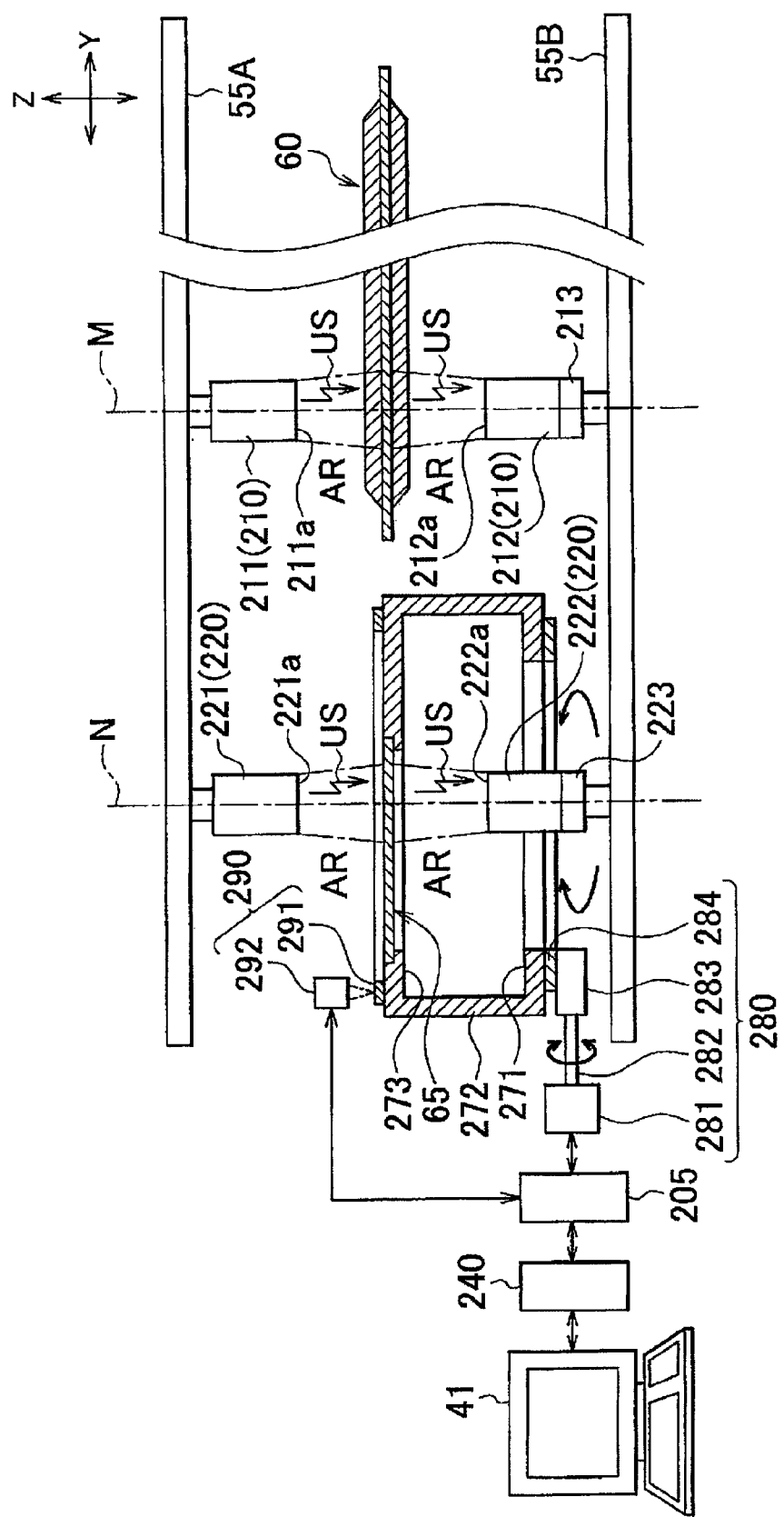
FIG. 17 is a view useful for explaining a principal part of the ultrasonic measuring system according to the second embodiment, a part of which is illustrated in a cross-section as viewed in a direction of arrows B-B in FIG. 16.

FIG. 16 is a schematic view illustrating the construction of the ultrasonic measuring system according to the second embodiment. FIG. 17 is an explanatory view of a principal part of the ultrasonic measuring system according to the second embodiment, a part of which is a cross-section as viewed in a direction of arrows B-B in FIG. 16.

Initially, the first and second ultrasonic sensors 211, 212 of the actual-measurement ultrasonic sensor set 210 will be described with reference to FIG. 16 and FIG. 17. The first ultrasonic sensor 211 is a flat-type transmitting sensor that permits propagation of unfocused ultrasonic waves US, and is also able to receive ultrasonic waves. In the second embodiment, the first ultrasonic sensor 211 as the flat-type transmitting sensor has a single first vibration surface 211a from which ultrasonic waves US are transmitted, and the first vibration surface 211a as a whole is formed in a circular shape. In operation, the ultrasonic waves US are transmitted from the first ultrasonic sensor 211 to at least within an area of the electrode 60 which is opposed to the first vibration surface 211a, via an air layer AR. When the second ultrasonic sensor 212 operates as a transmitting sensor, the sensor 212 operates substantially in the same manner as the first ultrasonic sensor 211, except that the first vibration surface 211a is replaced by a second vibration surface 212a of the second ultrasonic sensor 212.

The second ultrasonic sensor 212 is a flat-type receiving sensor that permits propagation of unfocused ultrasonic waves US, and is also able to send ultrasonic waves. In the second embodiment, the second ultrasonic sensor 212 as the flat-type receiving sensor has a single second vibration surface 212a that receives ultrasonic waves US, and the second vibration surface 212a as a whole is formed in a circular shape. The entire area of the second vibration surface 212a of the second ultrasonic sensor 212 is able to receive ultrasonic waves (transmitted waves) US sent from the first ultrasonic sensor 211 for irradiation of the electrode 60 and transmitted through at least the electrode 60, via an air layer AR. When the first ultrasonic sensor 211 operates as a receiving sensor, the sensor 211 operates substantially in the same manner as the second ultrasonic sensor 212, except that the second vibration surface 212a is replaced by the first vibration surface 211a.

The second ultrasonic sensor 212 is provided with a circuit portion 213 for improving the accuracy of the received signal, so that a second received signal is obtained by converting ultrasonic vibrations received at the second vibration surface 212a into a voltage signal and amplifying the received signal with high accuracy. The circuit portion 213 for improving the accuracy of the received signal incorporates a noise removal circuit for removing a signal (noise) as an impediment contained in the received signal that has been converted, and a signal amplifying circuit that amplifies the received signal from which noise has been removed, to generate the second received signal and the third received signal.

The frequencies of the first and second ultrasonic sensors 211, 212 are in the vicinity of about 40 KHz, and the first and second ultrasonic sensors 211, 212 have nominal frequencies that are in the same frequency band. The first ultrasonic sensor 211 and the second ultrasonic sensor 212 are both oriented in a direction perpendicular to the electrode 60. Where the frequency of the first and second ultrasonic sensors 211, 212 of the actual-measurement ultrasonic sensor set 210 is 40 KHz, for example, the first ultrasonic sensor 211 and the second ultrasonic sensor 212 are located with the electrode 60 (or the reference foil 65) interposed therebetween, via the air layers AR, such that the opposed first vibration surface 211a and second vibration surface 212a are spaced by a distance of about 70 mm apart from each other. Namely, in the actual-measurement ultrasonic sensor set 210, the distance between the first vibration surface 211a and the electrode 60 or reference foil 65, and the distance between the second vibration surface 212a and the electrode 60 or reference foil 65 are both set to 35 mm.

The first ultrasonic sensor 211 is mounted on the upper slide shaft 55A, such that its mounting position can be changed, and the sensor 211 can be immovably fixed at a given position The second ultrasonic sensor 212 is mounted on the lower slide shaft 55B, such that its mounting position can be changed, and the sensor 212 can be immovably fixed at a position where the sensor 212 is opposed to the first ultrasonic sensor 211.

Next, the first and second calibration ultrasonic sensors 221, 222 of the calibration ultrasonic sensor set 220 will be described with reference to FIG. 16 and FIG. 17. The first calibration ultrasonic sensor 221 is a flat-type transmitting sensor that permits propagation of unfocused ultrasonic waves US, and is also able to receive ultrasonic waves. Thus, the first calibration ultrasonic sensor 221 is constructed and operates substantially in the same manner as the first and second ultrasonic sensors 211, 212. Namely, in the second embodiment, the first calibration ultrasonic sensor 221 as the flat-type transmitting sensor has a single first vibration surface 221a from which ultrasonic waves US are transmitted, and the first vibration surface 221a as a whole is formed in a circular shape. In operation, the ultrasonic waves US are transmitted from the first calibration ultrasonic sensor 221 to at least within an area of the reference foil 65 which is opposed to the first vibration surface 221a, via an air layer AR. When the second calibration ultrasonic sensor 222 operates as a transmitting sensor, the sensor 222 operates substantially in the same manner as the first calibration ultrasonic sensor 221, except that the first vibration surface 221a is replaced by a second vibration surface 222a of the second ultrasonic sensor 222.

The second calibration ultrasonic sensor 222 is a flat-type receiving sensor that permits propagation of unfocused ultrasonic waves US, and is also able to send ultrasonic waves. Thus, the second calibration ultrasonic sensor 222 is constructed and operates substantially in the same manner as the first and second ultrasonic sensors 211, 212 and the first calibration ultrasonic sensor 221. Namely, in the second embodiment, the second calibration ultrasonic sensor 222 as the flat-type receiving sensor has a single second vibration surface 222a that receives ultrasonic waves US, and the second vibration surface 222a as a whole is formed in a circular shape. The entire area of the second vibration surface 222a of the second calibration ultrasonic sensor 222 is able to receive ultrasonic waves (transmitted waves) US sent from the first calibration ultrasonic sensor 221 for irradiation of the reference foil 65 and transmitted through at least the reference foil 65, via an air layer AR. When the first calibration ultrasonic sensor 221 operates as a receiving sensor, the sensor 221 operates substantially in the same manner as the second calibration ultrasonic sensor 222, except that the second vibration surface 222a is replaced by the first vibration surface 221a.

The second calibration ultrasonic sensor 222 is provided with a circuit portion 223 for improving the accuracy of the received signal, so that a first received signal is obtained by converting ultrasonic vibrations received at the second vibration surface 222a into a voltage signal and amplifying the received signal with high accuracy. The circuit portion 223 for improving the accuracy of the received signal incorporates a noise removal circuit for removing a signal (noise) as an impediment contained in the received signal that has been converted, and a signal amplifying circuit that amplifies the received signal from which noise has been removed, to generate the first received signal.

Like the first and second ultrasonic sensors 211, 212, the frequencies of the first and second calibration ultrasonic sensors 221, 222 are in the vicinity of about 40 KHz, and the first and second calibration ultrasonic sensors 221, 222 have nominal frequencies that are in the same frequency band. The first calibration ultrasonic sensor 221 and the second calibration ultrasonic sensor 222 are both oriented in a direction perpendicular to the reference foil 65. Like the actual-measurement ultrasonic sensor set 210, where the frequency of the first and second calibration ultrasonic sensors 221, 222 of the calibration ultrasonic sensor set 220 is 40 KHz, for example, the first calibration ultrasonic sensor 221 and the second calibration ultrasonic sensor 222 are located with the reference foil 65 interposed therebetween, via air layers AR, such that the opposed first vibration surface 221a and second vibration surface 222a are spaced by a distance of about 70 mm apart from each other. Namely, in the calibration ultrasonic sensor set 220, the distance between the first vibration surface 221a and the reference foil 65, and the distance between the second vibration surface 222a and the reference foil 65 are both set to 35 mm.

The first calibration ultrasonic sensor 221 is mounted on the upper slide shaft 55A, such that its mounting position can be changed, and the sensor 221 can be immovably fixed at a given position The second calibration ultrasonic sensor 222 is mounted on the lower slide shaft 55B, such that its mounting position can be changed, and the sensor 222 can be immovably fixed at a position where the sensor 222 is opposed to the first calibration ultrasonic sensor 221.

The first ultrasonic sensor 211 and the first calibration ultrasonic sensor 221 are electrically connected to a first ultrasonic oscillator 211F. The first ultrasonic oscillator 211F has an oscillating circuit for applying voltage to the first ultrasonic sensor 211 and the first calibration ultrasonic sensor 221 so as to produce ultrasonic vibrations in the first vibration surfaces 211a, 221a, and a receiving circuit for converting vibrations of ultrasonic waves received by the first vibration surfaces 211a, 221a, into voltage signals, and receiving the voltage signals.

The second ultrasonic sensor 212 and the second calibration ultrasonic sensor 222 are electrically connected to a second ultrasonic oscillator 212F for producing ultrasonic vibrations in the second vibration surfaces 212a, 222a. The second ultrasonic oscillator 212F has an oscillating circuit for applying voltage to the second ultrasonic sensor 212 and the second calibration ultrasonic sensor 222 so as to produce ultrasonic vibrations in the second vibration surfaces 212a, 222a, and a receiving circuit for converting vibrations of ultrasonic waves received by the second vibration surfaces 212a, 222a, into voltage signals, and receiving the voltage signals. The first ultrasonic oscillator 211F and the second ultrasonic oscillator 212F are electrically connected to an ultrasonic measurement control unit 205.

Next, the ultrasonic measurement control unit 205 will be described with reference to FIG. 16 and FIG. 17. Like the ultrasonic measurement control unit 5 of the first embodiment as described above, the ultrasonic measurement control unit 205 controls the actual-measurement ultrasonic sensor set 210 (the first and second ultrasonic sensors 211, 212) and the calibration ultrasonic sensor set 220 (the first and second calibration ultrasonic sensors 221, 222), more specifically, controls sending and receiving of ultrasonic waves US, and measurement conditions between the actual-measurement ultrasonic sensor set 210 and the calibration ultrasonic sensor set 220. Furthermore, the ultrasonic measurement control unit 205 performs driving control on a motor 281 of a drive unit 280, and performs detection control on a rotary encoder unit 290, as will be described later.

The ultrasonic measurement control unit 205 is configured to cause each of the first and second ultrasonic sensors 211, 212 of the actual-measurement ultrasonic sensor set 210 and the first and second calibration ultrasonic sensors 221, 222 of the calibration ultrasonic sensor set 220 to generate ultrasonic waves US, under control conditions that the maximum oscillation voltage is 1 KV, the maximum oscillation frequency is 10 Hz (oscillation occurs every 100 µs), the maximum number of generated waves (the number of waves that can be transmitted within a given time) is 100 waves, and the maximum A/D conversion frequency is 100 MHz, for example.

The ultrasonic measurement control unit 205 is electrically connected to a thickness computing unit 240. The thickness computing unit 240 calculates the basis weight and coating profile of the electrode paste 62 (See FIG. 7), based on a received signal of ultrasonic waves US received by a receiving-side ultrasonic sensor as one of the first ultrasonic sensor 211 and the second ultrasonic sensor 212. The thickness computing unit 240 includes a microcomputer (not shown) of known configuration having CPU, RAM, ROM, etc.

The RAM of the thickness computing unit 240 receives, as set values, the attenuation factor of ultrasonic waves US when propagating through the air layer AR, the attenuation factor of ultrasonic waves US when transmitted through the reference foil 65, the attenuation factor of ultrasonic waves US when transmitted through the electrode 60, the attenuation factor of ultrasonic waves US when transmitted through the metal foil 61 or the thickness of the metal foil 61, the atmosphere temperature of the air layer AR measured by a thermometer or thermometers (not shown), the temperatures of the first and second ultrasonic sensors 211, 212 and the first and second calibration ultrasonic sensors 221, 222, the probe-to-probe distance between the first vibration surface 211a, 221a and the second vibration surface 212a, 222a, the sound velocity, density, and acoustic impedance corresponding to the temperature, in the air layer AR, the air pressure of the air layer AR through which ultrasonic waves propagate, coordinates of regions of the reference foil 65 through which ultrasonic waves US are transmitted, and so forth.

Also, the ROM of the thickness computing unit 240 stores a program for executing calibration of the first and second calibration ultrasonic sensors 221, 222 of the calibration ultrasonic sensor set 220, a program for calculating the attenuation factor of transmitted waves generated by one of the first and second ultrasonic sensors 211, 212 of the actual-measurement ultrasonic sensor set 210 and transmitted through the reference foil 65, a program for calculating the attenuation factor of transmitted waves generated by one of the first and second ultrasonic sensors 211, 212 of the actual-measurement ultrasonic sensor set 210 and transmitted through the electrode 60 (the electrode paste 62), a program for correcting the sonic waveform of the transmitted and received waves by approximating the waveform by a sine wave, a basis-weight calculation program for computing the thickness, or basis weight, of the electrode paste 62, based on the calculated attenuation factor of the transmitted waves, a program for displaying the computation results in the form of numerical values and/or images, on the monitor 41, a program for moving the upper slide shaft 55A and the lower slide shaft 55B in the width direction (Y-axis direction), a program for controlling driving of the motor 281 and operation of the rotary encoder 290, a program for correcting machine differences between the first and second ultrasonic sensors 211, 212 and the first and second calibration ultrasonic sensors 221, 222, and other programs.

In the thickness computing unit 240, the CPU is loaded with the above-indicated programs, so as to perform certain operations, such as operating the upper slide shaft 55A and the lower slide shaft 55B, and displaying numerical values and/or images representing the basis weight and coating profile of the electrode paste 62, and the regions of the reference foil 65 through which ultrasonic waves are transmitted, on the monitor 41 connected to the thickness computing unit 240.

Figure 18:
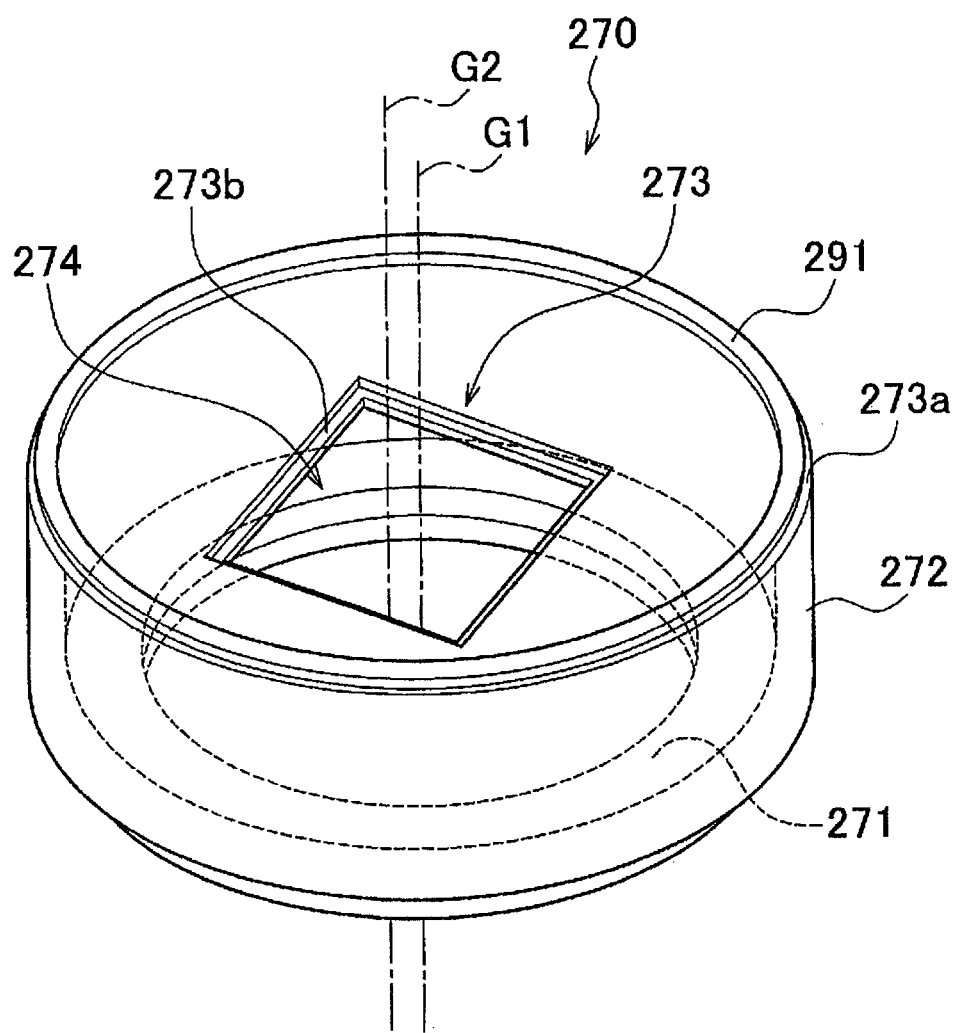
FIG. 18 is a perspective view showing a reference foil holding member that constitutes the ultrasonic measuring system according to the second embodiment.

Next, the mechanism for rotating the reference foil 65 will be described with reference to FIG. 17 and FIG. 18. FIG. 18 is a perspective view showing a reference foil holding member that constitutes the ultrasonic measuring system according to the second embodiment. For easy understanding of the drawings, the first and second ultrasonic oscillators electrically connected to the ultrasonic measurement control unit, and wiring paths to the upper slide shaft and lower slide shaft, as shown in FIG. 16, are not illustrated in FIG. 18.

In the second embodiment, the ultrasonic measuring system 201 includes the reference foil holding member 270 (holding member), drive unit 280, and the rotary encoder 290 (positioning device), as a mechanism for rotating the reference foil 65.

Initially, the reference foil holding member 270 will be described. In the second embodiment, the reference foil holding member 270 holds a piece of reference foil 65 formed in a square shape, such that respective edge portions of the four sides of the foil 65 are placed on the holding member 270, while taking slack out of the reference foil 65 in the direction of its plane, and maintaining a natural planar condition of the foil 65 to which excessive tension is not applied. As shown in FIG. 17 and FIG. 18, for example, the reference foil holding member 270 consists of an upright portion 272 formed in a cylindrical shape about an axis G1, a base portion 271 formed in an annular shape about the axis G1 and connected to the lower side of the upright portion 272, and a reference foil holding portion 273 formed like a flat plate and connected to the upper side of the upright portion 272.

The reference foil holding portion 273 has a rotation detection surface 273 as an upper surface thereof, and an opening 274 in the form of a square through-hole. The reference foil holding portion 273 is formed with support faces 273B having a different level from the rotation detection surface 273a, such that the support faces 273B extend along the four sides of the opening 274, respectively. The edge portions of the four sides of the reference foil 65 are placed on the support faces 273B at the four sides of the opening 274, as shown in FIG. 17. Then, the reference foil 65 placed on the support faces 273B is fixed by means of a fixing member (not shown), around the opening 274, so that the reference foil holding member 270 can hold the reference foil 65 while taking the slack out of the reference foil 65 in the direction of its plane, and maintaining a natural planar condition of the foil 65 to which excessive tension is not applied. As shown in FIG. 18, the opening 274 including the support faces 273b is formed at such a position that a center point G2 of the opening 274 is displaced from the axis G1 of the reference foil holding member 270.

Next, the drive unit 280 will be described. In the second embodiment, the drive unit 280 operates the reference foil holding member 270 to cause rotary motion thereof, and stops its operation. More specifically, the drive unit 280 consists of the motor 281, a drive shaft 282 that transmits rotary force of the motor 281, a driving force transmitting portion 283, and a driving force transmitted portion 284. The motor 281 is electrically connected to the ultrasonic measurement control unit 205, and the ultrasonic measurement control unit 205 controls driving of the motor 281, to rotate the motor 281 and stop the rotation of the motor 281. The driving force transmitting portion 281 and the driving force transmitted portion 284 convert the direction of rotation of the drive shaft 282 (or direction of rotation about an axis that extends along the Y axis in FIG. 17), into the direction of rotation of the reference foil holding member 270 about the axis G1 (or direction of rotation about an axis that extends along the Z axis in FIG. 17). Namely, the drive unit 280 converts rotation of the motor 281 into rotary motion of the reference foil holding member 270 about the axis G1.

In the ultrasonic measuring system 210, the reference foil 65 placed on the support faces 273b of the reference foil holding portion 273 of the reference foil holding member 270 is positioned so as to be movable relative to the first ultrasonic sensor 211 and second ultrasonic sensor 212 that are in fixed conditions, within a range in which the reference foil 65 intersect with an imaginary line M that connects the center of the first ultrasonic sensor 211 with the center of the second ultrasonic sensor 212 opposed to the first ultrasonic sensor 211 when the reference foil holding member 270 is rotated by the drive unit 280. Also, the reference foil 65 placed on the support faces 273b of the reference foil holding portion 273 of the reference foil holding member 270 is positioned so as to be movable relative to the first calibration ultrasonic sensor 221 and second calibration ultrasonic sensor 222 that are in fixed conditions, within a range in which the reference foil 65 intersect with an imaginary line N that connects the center of the first calibration ultrasonic sensor 221 with the center of the second calibration ultrasonic sensor 222 opposed to the first calibration ultrasonic sensor 221 when the reference foil holding member 270 is rotated by the drive unit 280.

Next, the rotary encoder 290 will be described. In the second embodiment, the positioning device of the invention is the rotary encoder 290 as well known in the art. The rotary encoder 290 consists of a detected portion 291, and a position detection sensor portion 292. As shown in FIG. 18, the detected portion 291 is formed in an annular shape, and is provided on the rotation detection surface 273a of the reference foil holding portion 273 of the reference foil holding member 270. The position detection sensor portion 292 is provided at a certain position opposed to the rotation detection surface 273a of the reference foil holding portion 273, and is electrically connected to the ultrasonic measurement control unit 205.

As shown in FIG. 17 and FIG. 18, the rotary encoder 290 detects positions of the reference foil holding member 270 that is rotated about the axis G1, at which positions the imaginary line M that connects the centers of the opposed first ultrasonic sensor 211 and second ultrasonic sensor 212 passes through the centers C1a-C5a (see FIG. 19) of ultrasonic wave transmittable regions C1-C5 as specified regions of the reference foil 65. Also, the rotary encoder 290 detects positions of the reference foil holding member 270, at which positions the imaginary line N that connects the centers of the opposed first calibration ultrasonic sensor 221 and second calibration ultrasonic sensor 222 passes through the centers C1a-C5a of the ultrasonic wave transmittable regions C1-C5 as specified regions of the reference foil 65.

Next, the ultrasonic measuring method according to the second embodiment will be described. The ultrasonic measuring method of the second embodiment is a method for performing quality check on the basis weight of the electrode paste 62, using the ultrasonic measuring system 201 constructed as described above.

The ultrasonic measuring method of the second embodiment uses a pair of ultrasonic sensors in the form of the first ultrasonic sensor 211 and the second ultrasonic sensor 212, and the first ultrasonic sensor 211 is placed, via the air layer AR, on one side of the electrode 60 as viewed in the thickness direction Z of the electrode 60, which is formed by coating the opposite surfaces 61a, 61b of the metal foil 61 made of a metal and wound in the form of a roll, with the electrode paste 62, while the second ultrasonic sensor 212 is placed, via the air layer AR, on the other side of the electrode 60. In this condition, the thickness (basis weight) of the electrode paste 62 is measured by transmitting ultrasonic waves US between the first ultrasonic sensor 211 and the second ultrasonic sensor 212. The ultrasonic sensor sets used in the ultrasonic measuring method include at least one set of actual-measurement ultrasonic sensors 210 for measuring the basis weight of the electrode paste 62, and the calibration ultrasonic sensor set 220 consisting of the first calibration ultrasonic sensor 221 and the second calibration ultrasonic sensor 222, aside from the first ultrasonic sensor 211 and the second ultrasonic sensor 212. In operation, the calibration ultrasonic sensor set 220 performs calibration, during measurement of the thickness of the electrode paste 62, and the actual-measurement ultrasonic sensor set 210 calculates the basis weight of the electrode paste 62, using measurement condition values obtained by the calibration ultrasonic sensor set 220.

The ultrasonic measuring method according to the second embodiment of the invention is characterized in that flat-type ultrasonic sensors that permit propagation of unfocused ultrasonic waves US are used as the first calibration ultrasonic sensor 221 and second calibration ultrasonic sensor 222 of the calibration ultrasonic sensor set 220, and flat-type ultrasonic sensors that permit propagation of unfocused ultrasonic waves US are used as the first ultrasonic sensor 211 and second ultrasonic sensor 212 of the actual-measurement ultrasonic sensor set 210.

In the ultrasonic measuring method according to the second embodiment of the invention, prior to the actual measurement by the actual-measurement ultrasonic sensor set 210, the reference foil 65 used for calibration is placed between the first calibration ultrasonic sensor 221 and the second calibration ultrasonic sensor 222 of the calibration ultrasonic sensor set 220, as shown in FIG. 10A, and a first received signal $S_K$ representing ultrasonic waves US sent from the first calibration ultrasonic sensor 221, transmitted through the reference foil 65, and received by the second calibration ultrasonic sensor 222 is obtained in advance as a measurement condition value.

In the ultrasonic measuring method according to the second embodiment, in order to obtain the first received signal $S_K$, first sample received signals $S_{K1}$-$S_{K5}$ corresponding to a plurality of specified regions C1-C5 (ultrasonic wave transmittable regions C1-C5) of the reference foil 65 are obtained, as received signals of ultrasonic waves US sent from the first calibration ultrasonic sensor 221, transmitted through the five ultrasonic wave transmittable regions C1-C5 of the reference foil 65, and received by the second calibration ultrasonic sensor 222. Then, the first received signal $S_K$ is obtained through computation, based on the five (a plurality of) first sample received signals $S_{K1}$-$S_{K5}$.

Figure 20:
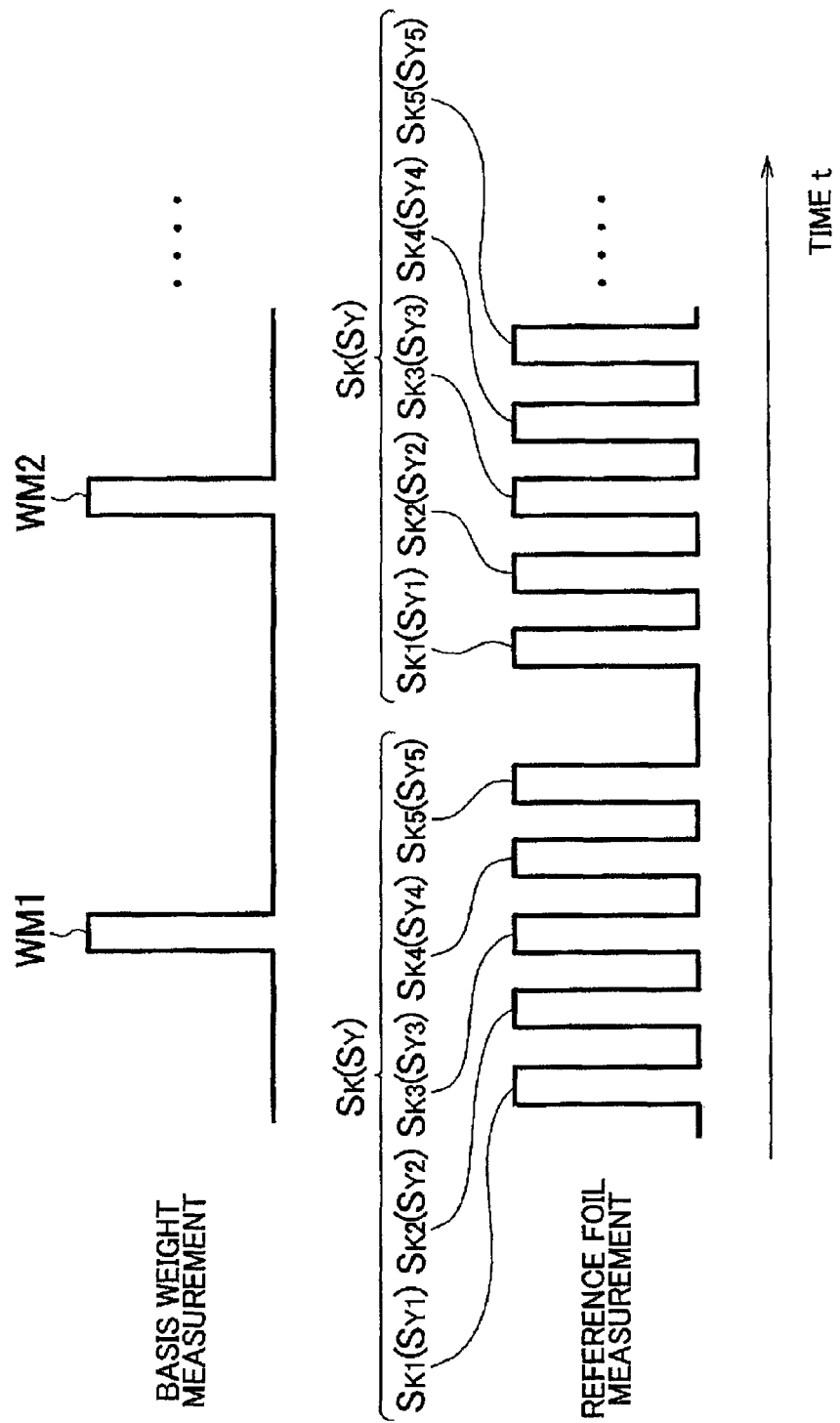
FIG. 20 is a time chart schematically indicating the timing of basis weight measurements conducted by an actual-measurement ultrasonic sensor set and the timing of reference foil measurements conducted by a calibration ultrasonic sensor set, in the ultrasonic measuring method according to the second embodiment.
Figure 21:
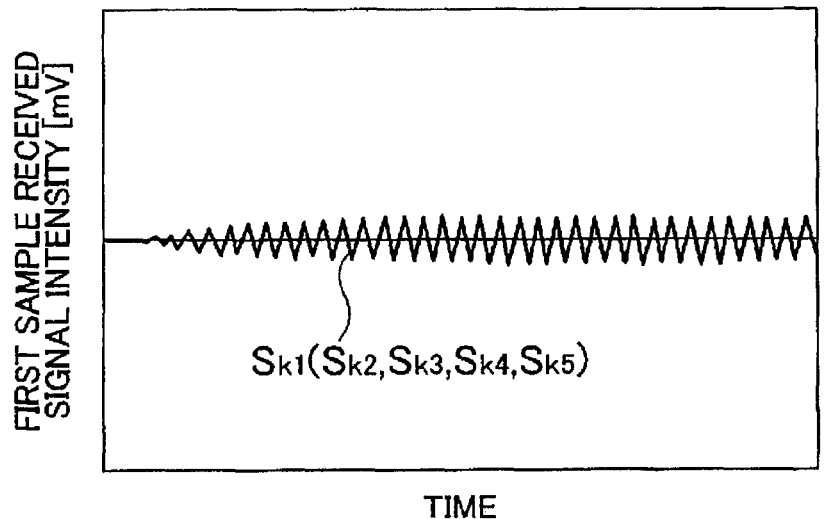
FIG. 21 is an explanatory view schematically showing a first sample received signal, in the ultrasonic measuring method according to the second embodiment.

The above method of obtaining the first received signal $S_K$ will be more specifically described with reference to FIG. 17, and FIG. 19 through FIG. 21. FIG. 19 is a schematic view showing the manner of obtaining the first sample received signals or third sample received signals by transmitting ultrasonic waves through five regions of the reference foil, in the ultrasonic measuring method according to the second embodiment. FIG. 20 is a time chart schematically indicating the timing of basis weight measurements conducted by the actual-measurement ultrasonic sensor set, and the timing of reference foil measurements conducted by the calibration ultrasonic sensor set, in the ultrasonic measuring method according to the second embodiment. FIG. 21 is an explanatory view schematically showing an example of the first sample received signal, in the ultrasonic measuring method according to the second embodiment.

In the ultrasonic measuring method according to the second embodiment, when the calibration ultrasonic sensor set 220 performs calibration, using the reference foil 65, ultrasonic waves US sent from the first calibration ultrasonic sensor 221 are directed toward and transmitted through the five ultrasonic wave transmittable regions C1-C5 (a plurality of regions) of the reference foil 65, as shown in FIG. 19. Namely, in the calibration ultrasonic sensor set 220, the first calibration ultrasonic sensor 221 is stopped and fixed at a given position of the upper slide shaft 55A, and the second calibration ultrasonic sensor 222 is stopped at a position that is opposed to the first calibration ultrasonic sensor 221 and lies on the imaginary line N that connects the center of the first calibration ultrasonic sensor 221 with the center of the second calibration ultrasonic sensor 222, and is fixed to the lower slide shaft 55B.

In the above condition, the drive unit 280 and the rotary encoder 290 are operated so as to rotate the reference foil 65. To this end, the reference foil 65 is set and held in position such that the center point H of the reference foil 65 matches the center point G2 of the opening 274 of the reference foil holding member 270, and the motor 281 is rotated so as to rotate the reference foil holding member 270 about the center G1. At this time, the reference foil 65 held by the reference foil holding member 270 revolves around the center G1, relative to the reference foil holding member 270. It is, however, to be noted that the center point G2 of the opening 274 is displaced from the center G1 of the reference foil holding member 270, and the center point H of the reference foil 65 lies within the opening 274 of the reference foil holding member 270. Therefore, when the reference foil holding member 270 is rotated, the imaginary line N that connects the center of the first calibration ultrasonic sensor 221 with the center of the second calibration ultrasonic sensor 222 passes through some point on a pitch circle R that has a center at the center point H of the reference foil 65 and passes the centers C1a, C2a, C3a, C4a, C5a of the desired, five ultrasonic wave transmittable regions C1-C5.

In the ultrasonic measuring method according to the second embodiment, the calibration ultrasonic sensor set 220 performs calibration with respect to the five ultrasonic wave transmittable regions C1-C5 (a plurality of regions) of the reference foil 65; therefore, during rotation of the reference foil holding member 270, rotation of the motor 281 is temporarily stopped when the imaginary line N successively reaches the centers C1a, C2a, C3a, C4a, C5a on the pitch circle R in this order. The position at which the rotation of the motor 281 is to be stopped is detected by the rotary encoder 290. More specifically, the position detection sensor portion 292 detects the circumferential positions of the reference foil holding member 270 corresponding to the centers C1a, C2a, C3a, C4a, C5a, respectively, namely, the circumferential positions of the detected portion 291.

Then, ultrasonic waves US sent from the first calibration ultrasonic sensor 221 are directed toward and transmitted through the reference foil 65, at positions where the imaginary line N that connects the center of the first calibration ultrasonic sensor 221 with the center of the second calibration ultrasonic sensor 222 passes through the centers C1a, C2a, C3a, C4a, C5a. At the positions where the imaginary line N passes through the centers C1a, C2a, C3a, C4a, C5a, five first sample received signals $S_{K1}$-$S_{K5}$ (see FIG. 21) are obtained as received signals of ultrasonic waves US sent from the first calibration ultrasonic sensor 221, transmitted through the ultrasonic wave transmittable regions C1-C5 (a plurality of regions), and received by the second calibration ultrasonic sensor 222. Namely, the first sample received signal $S_{K1}$ is a received signal of ultrasonic waves US transmitted through the ultrasonic wave transmittable region C1. The first sample received signal $S_{K2}$ is a received signal of ultrasonic waves US transmitted through the ultrasonic wave transmittable region C2. The first sample received signal $S_{K3}$ is a received signal of ultrasonic waves US transmitted through the ultrasonic wave transmittable region C3. The first sample received signal $S_{K4}$ is a received signal of ultrasonic waves US transmitted through the ultrasonic wave transmittable region C4. The first sample received signal $S_{K5}$ is a received signal of ultrasonic waves US transmitted through the ultrasonic wave transmittable region C5. Thus, the first received signal $S_K$ is obtained through computation by a least square method, based on the five first sample received signals $S_{K1}$-$S_{K5}$.

Subsequently, for actual measurement of the basis weight (thickness) of the electrode paste 62 of the electrode 60, the electrode 60 is placed between the first ultrasonic sensor 211 and the second ultrasonic sensor 212 of the actual-measurement ultrasonic sensor set 210, as shown in FIG. 11B, and a second received signal $S_X$ of ultrasonic waves US sent from the first ultrasonic sensor 211, transmitted through the electrode 60, and received by the second ultrasonic sensor 212 is obtained. The basis weight (thickness) of the electrode paste 62 is calculated based on the relative ratio of the first received signal $S_K$ and the second received signal $S_X$.

In the measurement of the basis weight (thickness), the first received signal $S_K$ used in the earlier basis weight measurement WM1 is not used as it is as the first received signal $S_K$ used in the following basis weight measurement WM2, but the above-described calibration is performed separately for the earlier basis weight measurement WM1 and the following basis weight measurement WM2. Namely, it is important to use a high-accuracy first received signal $S_K$ by obtaining five first sample received signals $S_{K1}$-$S_{K5}$ each time a basis weight measurement is carried out, and correcting and updating conditions of basis weight measurement in real time.

Next, a method for determining machine differences in individual ultrasonic sensors between the actual-measurement ultrasonic sensor set 210 and the calibration ultrasonic sensor set 220, namely, machine differences between the first ultrasonic sensor 211 and second ultrasonic sensor 212, and the first calibration ultrasonic sensor 221 and second calibration ultrasonic sensor 222 will be described. To determine machine differences in the individual ultrasonic sensors as indicated above, the calibration ultrasonic sensor unit 220 that performs calibration needs to obtain the first received signal $S_K$, according to the above-described ultrasonic measuring method of the second embodiment.

Also, the actual-measurement ultrasonic sensor set 210 is moved to the position at which the reference foil 65 is placed, and obtains a third received signal $S_Y$ (corresponding to $S_C$ indicated in FIG. 9B) of ultrasonic waves US sent from the first ultrasonic sensor 211, transmitted through the reference foil 65, and received by the second ultrasonic sensor 212. In order to obtain the third received signal $S_Y$ according to the ultrasonic measuring method of the second embodiment, third sample received signals $S_{Y1}$-$S_{Y5}$ corresponding to a plurality of specified regions C1-C5 (ultrasonic Wave transmittable regions C1-C5) of the reference foil 65 are obtained as received signals of ultrasonic waves US sent from the first ultrasonic sensor 211, transmitted through the five ultrasonic wave transmittable regions C1-C5 of the reference foil 65, and received by the second ultrasonic sensor 212. Then, the third received signal $S_Y$ is obtained through computation, based on the five (a plurality of) third sample received signals $S_{Y1}$-$S_{Y5}$.

Figure 22:
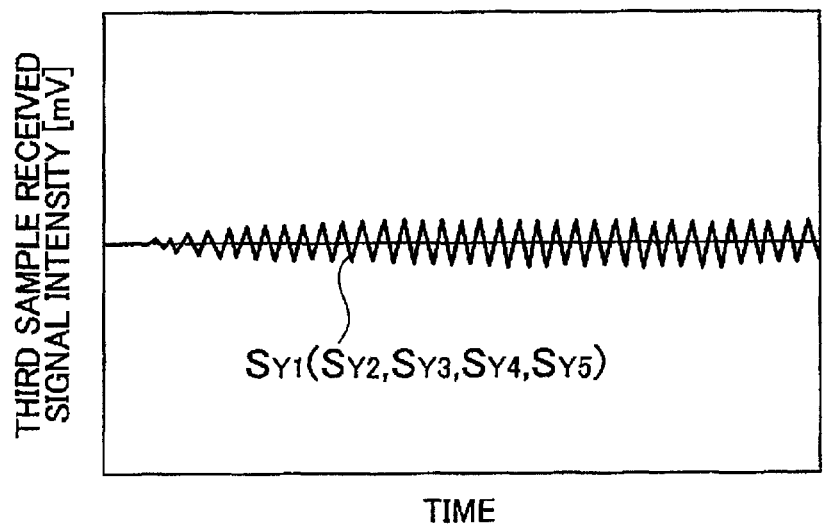
FIG. 22 is an explanatory view schematically showing a third sample received signal, in the ultrasonic measuring method according to the second embodiment.

The above method of obtaining the third received signal $S_Y$ will be more specifically described with reference to FIG. 19, FIG. 20 and FIG. 22. FIG. 22 is an explanatory view schematically showing an example of the third sample received signal, in the ultrasonic measuring method according to the second embodiment.

In the ultrasonic measuring method according to the second embodiment, when machine differences between the calibration ultrasonic sensor set 220 and the actual-measurement ultrasonic sensor set 210 are determined, using the reference foil 65, the first received signal $S_K$ is initially obtained through computation by the least square method, based on the five first sample received signals $S_{K1}$-$S_{K5}$. It is preferable that the ultrasonic wave transmittable regions C1-C5 through which ultrasonic waves US are transmitted so as to obtain the first sample received signals $S_{K1}$-$S_{K5}$ are the same regions as the ultrasonic wave transmittable regions C1-C5 through which ultrasonic waves US are transmitted so as to obtain the third sample received signals $S_{Y1}$-$S_{Y5}$. In this case, machine differences in the ultrasonic sensors between the actual-measurement ultrasonic sensor set 210 and the calibration ultrasonic sensor set 220 can be determined with improved accuracy.

Then, in the actual-measurement ultrasonic sensor set 210, ultrasonic waves US sent from the first ultrasonic sensor 211 are directed toward and transmitted through the five ultrasonic wave transmittable regions C1-C5 (a plurality of regions) of the reference foil 65, as shown in FIG. 19. Namely, in the actual-measurement ultrasonic sensor set 210 moved to the position at which the reference foil 65 is placed, the first ultrasonic sensor 211 is stopped and fixed at a given position of the upper slide shaft 55A, and the second ultrasonic sensor 212 is stopped at a position that is opposed to the first ultrasonic sensor 211 and lies on the imaginary line M that connects the center of the first ultrasonic sensor 211 with the center of the second ultrasonic sensor 212, and is fixed to the lower slide shaft 55B.

In the above condition, the drive unit 280 and the rotary encoder 290 are operated so as to rotate the reference foil 65 set in the opening 274 of the reference foil holding member 270. At this time, the reference foil 65 held by the reference foil holding member 270 revolves around the center G1, relative to the reference foil holding member 270. It is, however, to be noted that the center point G2 of the opening 274 is displaced from the center G1 of the reference foil holding member 270, and the center point H of the reference foil 65 lies within the opening 274 of the reference foil holding member 270. Therefore, when the reference foil holding member 270 is rotated, the imaginary line M that connects the center of the first ultrasonic sensor 211 with the center of the second ultrasonic sensor 212 passes through some point on a pitch circle R that has a center at the center point H of the reference foil 65 and passes the centers C1a, C2a, C3a, C4a, C5a of the desired, five ultrasonic wave transmittable regions C1-C5.

In the ultrasonic measuring method according to the second embodiment, the actual-measurement ultrasonic sensor set 210 allows ultrasonic waves US to be transmitted through the five ultrasonic wave transmittable regions C1-C5 (a plurality of regions) of the reference foil 65; therefore, during rotation of the reference foil holding member 270, rotation of the motor 281 is temporarily stopped when the imaginary line M successively reaches the centers C1a, C2a, C3a, C4a, C5a on the pitch circle R in this order. As described above, the rotary encoder 290 detects the circumferential positions of the reference foil holding member 270 corresponding to the centers C1a, C2a, C3a, C4a, C5a, respectively, and the rotation of the motor 281 is stopped at these positions.

Then, ultrasonic waves US sent from the first ultrasonic sensor 211 are directed toward and transmitted through the reference foil 65, at positions where the imaginary line M that connects the center of the first ultrasonic sensor 211 with the center of the second ultrasonic sensor 212 passes through the centers C1a, C2a, C3a, C4a, C5a. At the positions where the imaginary line M passes through the centers C1a, C2a, C3a, C4a, C5a, five third sample received signals $S_{Y1}$-$S_{Y5}$ (see FIG. 22) are obtained, as received signals of ultrasonic waves US sent from the first ultrasonic sensor 211, transmitted through the ultrasonic wave transmittable regions C1-C5 (a plurality of regions), and received by the second ultrasonic sensor 212. Namely, the third sample received signal $S_{Y1}$ is a received signal of ultrasonic waves US transmitted through the ultrasonic wave transmittable region C1. The third sample received signal $S_{Y2}$ is a received signal of ultrasonic waves US transmitted through the ultrasonic wave transmittable region C2. The third sample received signal $S_{Y3}$ is a received signal of ultrasonic waves US transmitted through the ultrasonic wave transmittable region C3. The third sample received signal $S_{Y4}$ is a received signal of ultrasonic waves US transmitted through the ultrasonic wave transmittable region C4. The third sample received signal $S_{Y5}$ is a received signal of ultrasonic waves US transmitted through the ultrasonic wave transmittable region C5. Thus, the third received signal $S_Y$ is obtained through computation by the least square method, based on the five third sample received signals $S_{Y1}$-$S_{Y5}$.

Here, the relationship between ultrasonic waves propagated through an air layer and conditions of the air layer will be described, using the illustrated calibration ultrasonic sensor unit 220. In the air layer AR between the first vibration surface 221a of the first calibration ultrasonic sensor 221 and the reference foil 65, or the air layer AR between the second vibration surface 222a of the second calibration ultrasonic sensor 222 and the reference foil 65, the density of the air layer AR, the temperature of the air layer AR, and a condition of convection (flow of air) in the air layer AR vary with time, in a strict sense. Needless to say, these conditions of the air layer AR are different, in a strict sense, between a location at which the actual-measurement ultrasonic sensor set 210 is placed, and a location at which the calibration ultrasonic sensor unit 220 is placed.

In the meantime, it is understood that if the conditions, such as the density and temperature, of the air layer AR change, the sound velocity, density, and acoustic impedance in the air layer, the wavelength of propagating ultrasonic waves US, etc. vary as parameters with changes in the temperature of the air layer AR, as described above with respect to the first embodiment. In particular, it has been found through research conducted by the applicant that, as the temperature of the air layer AR changes only by 1° C., the intensity of the received signal of the receiving-side ultrasonic sensor changes about 0.2%, with respect to a reference intensity of the received signal. Furthermore, the applicant has conducted research on the relationship between changes in the air pressure of the air layer AR, and the received signal intensity of ultrasonic waves propagated through the air layer AR and received by the receiving-side ultrasonic sensor.

In the research, the air layer through which ultrasonic waves to be received are propagated was located in an environment of a thermostatic chamber that is set to a constant temperature of 25° C., and three samples of receiving-side ultrasonic sensors having a nominal frequency of 40 KHz were used, while the ultrasonic waves were received at a frequency of 100 Hz (the waves were received every 10 µs). The research was conducted for 24 consecutive hours per day, for a period of one month.

Figure 23:
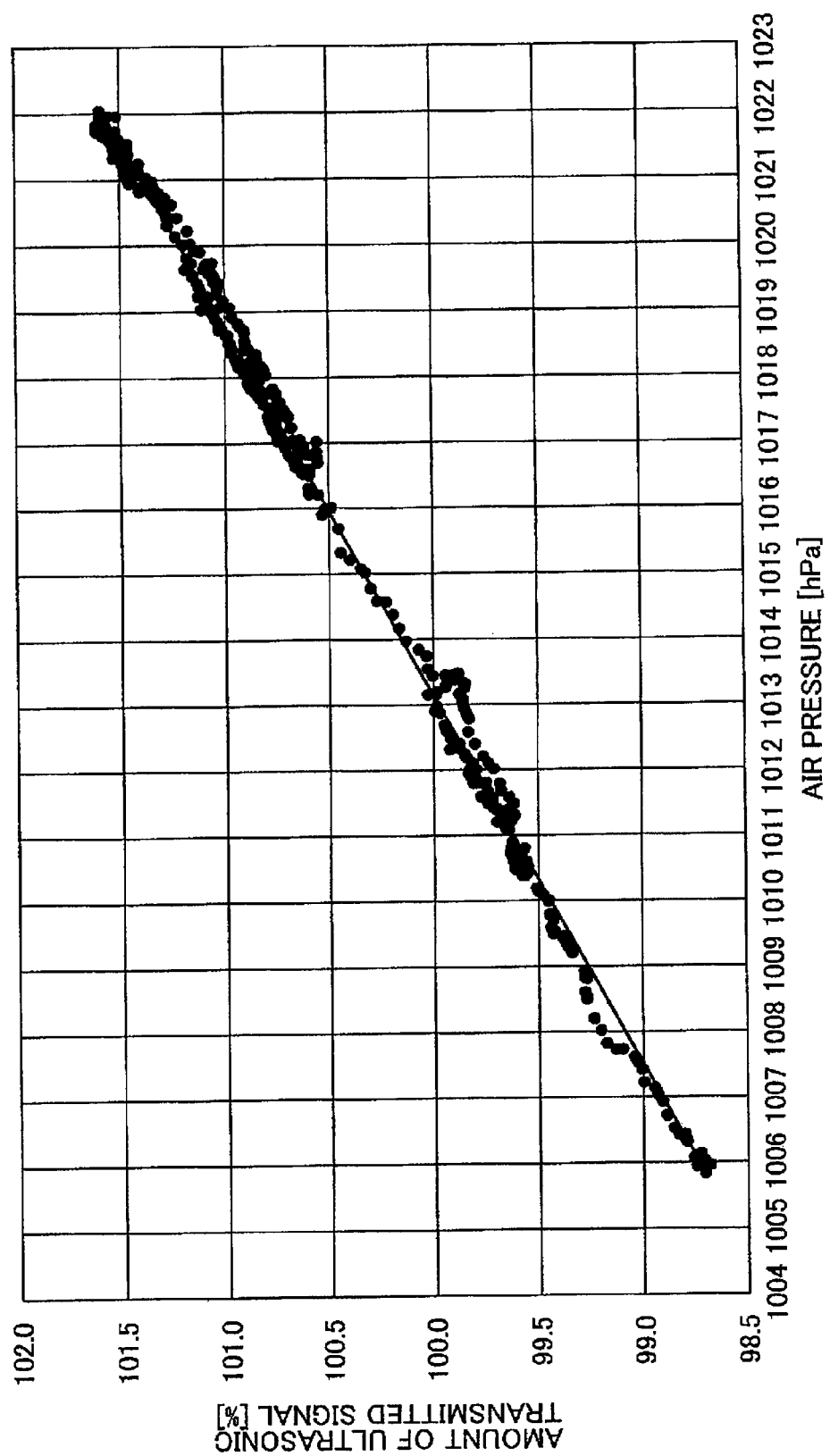
FIG. 23 is a graph indicating a research result regarding the relationship between the air pressure of an air layer, and the received signal intensity of ultrasonic waves received by a receiving-side ultrasonic sensor.
Figure 24:
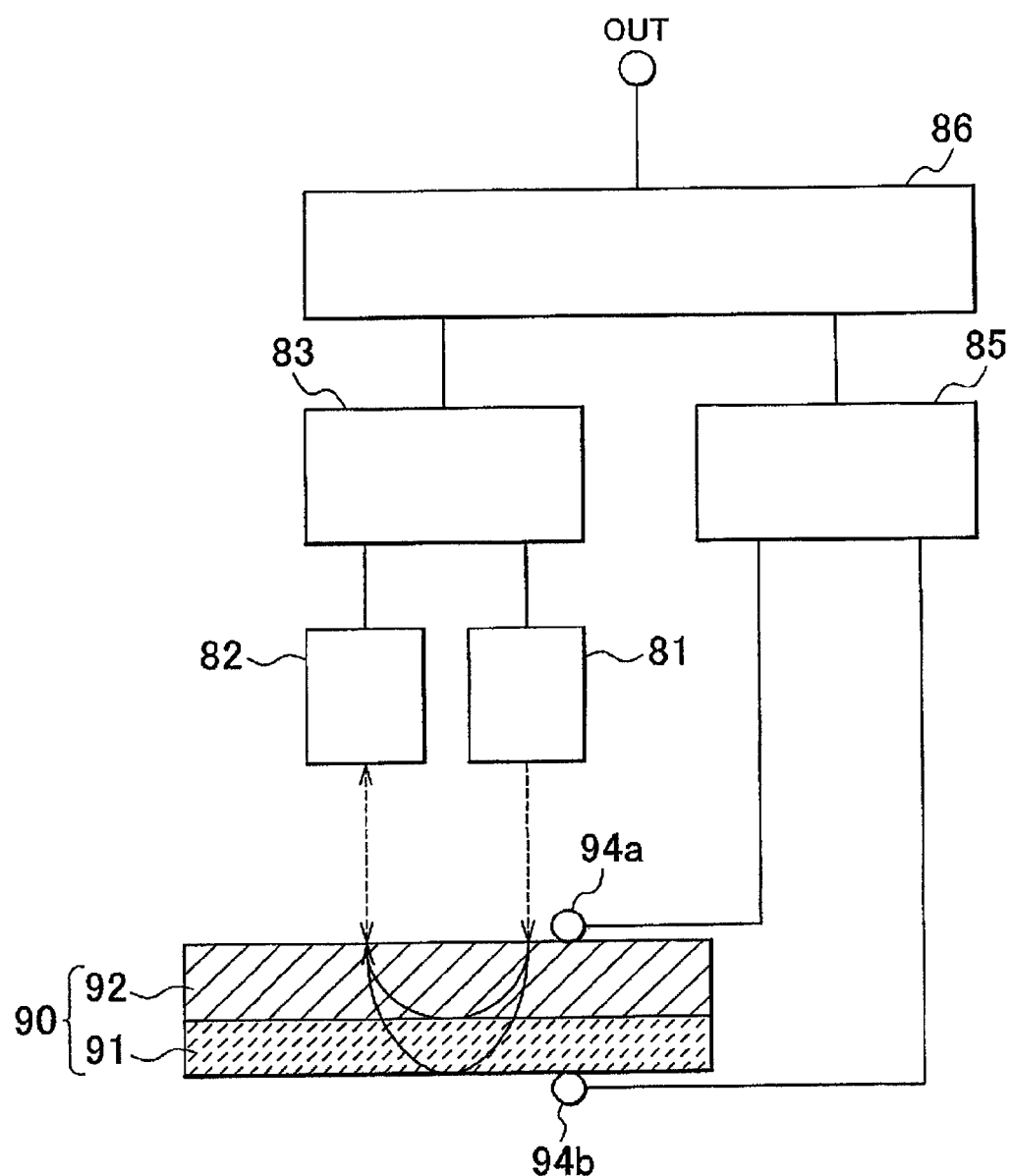
FIG. 24 is an explanatory view of an ultrasonic measuring system disclosed in JP 2008-102160 A.

The graph of FIG. 23 shows a research result regarding the relationship between the air pressure of the air layer and the received signal intensity of ultrasonic waves received by the receiving-side ultrasonic sensor. In FIG. 23, the received signal intensity obtained when the air pressure of the air layer is equal to 1013 hPa, which is generally used as atmospheric pressure, is expressed as 100%, and the horizontal axis indicates "air pressure (hPa)", while the vertical axis indicates "amount of ultrasonic transmitted signal" representing the intensity of the received signal of the receiving-side ultrasonic sensor. Also, data obtained in the research is subjected to computations (Y=0.1799X−80.195 $R^2$=0.9959) according to the least square method.

It is understood from the research result shown in FIG. 23 that, as the air pressure of the air layer AR changes only by 1 hPa, the intensity of the received signal of the receiving-side ultrasonic sensor changes about 0.2%, with respect to the reference received signal intensity. Namely, this means that, if a condition of air pressure, or the like, as well as the density and temperature, in the air layer AR, changes, the sound velocity, density, and acoustic impedance in the air layer AR, and the wavelength of propagating ultrasonic waves US, etc. change as parameters with time, in a strict sense, in accordance with changes in the conditions of the air layer AR. Needless to say, these conditions of the air layer AR differ, in a strict sense, between the location at which the actual-measurement ultrasonic sensor set 210 is placed, and the location at which the calibration ultrasonic sensor set 220 is placed.

It is, therefore, important to use a high-accuracy first received signal $S_K$ by obtaining five first sample received signals $S_{K1}$-$S_{K5}$ each time a basic weight measurement is conducted, and correcting and updating conditions of basis weight measurement in real time. Each time machine differences between the calibration ultrasonic sensor set 220 and the actual-measurement ultrasonic sensor set 210 are determined, using the reference foil 65, the third received signal $S_Y$ is obtained through computation by the least square method, based on the five third sample received signals $S_{Y1}$-$S_{Y5}$, so as to reflect the fact that the conditions of the air layer AR vary as parameters with time.

The operations and effects of the ultrasonic measuring method and ultrasonic measuring system according to the second embodiment of the invention will be described. In the ultrasonic measuring method according to the second embodiment, at least one set of ultrasonic sensors each of which consists of the first ultrasonic sensor 211 and the second ultrasonic sensor 212 is provided, and the first ultrasonic sensor 211 is placed, via the air layer AR, on one side of the electrode 60 formed by applying the electrode paste 62 by coating to the opposite surfaces 61a, 61b of the metal foil 61 wound in the form of a roll, as viewed in the thickness direction Z of the electrode 60, while the second ultrasonic sensor 212 is placed on the other side of the electrode 60, via the air layer AR, so that the thickness (basis weight) of the electrode paste 62 is measured by transmitting ultrasonic waves US between the first ultrasonic sensor 211 and the second ultrasonic sensor 212, as in the first embodiment. In the ultrasonic measuring method, the above-indicated at least one set of ultrasonic sensors includes at least one set of actual-measurement ultrasonic sensors 210 for measuring the basis weight of the electrode paste 62, and the calibration ultrasonic sensor set 220 consisting of the first calibration ultrasonic sensor 221 and the second calibration ultrasonic sensor 222, aside from the first ultrasonic sensor 211 and the second ultrasonic sensor 212. During measurement of the thickness of the electrode paste 62, the calibration ultrasonic sensor set 220 performs calibration, and the actual-measurement ultrasonic sensor set 210 calculates the basis weight of the electrode paste 62, using the measurement condition values obtained by the calibration ultrasonic sensor set 220. Therefore, when the thickness of the electrode paste 62 is measured on the production line on which the electrode 60 is produced by coating the metal foil 61 with the electrode paste 62, in the battery production process, error factors of the measurement accuracy due to self-heating of the ultrasonic sensors and changes in the temperature of the air layers AR can be excluded or eliminated, and the thickness of the electrode paste 62 can be measured with improved accuracy.

Thus, according to the ultrasonic measuring method of the second embodiment of the invention, error factors of the measurement accuracy due to self-heating of the ultrasonic sensors and changes in the temperature of the air layers can be excluded or eliminated, so that the basis weight (thickness) of the electrode paste 62 applied by coating to the electrode 60 produced on the production line can be advantageously measured on the production line with high accuracy, as in the first embodiment.

The ultrasonic measuring method of the second embodiment is characterized in that the first sample received signals $S_{K1}$-$S_{K5}$ corresponding to the five ultrasonic wave transmittable regions C1-C5 of the reference foil 65 are obtained as received signals of ultrasonic waves US sent from the first calibration ultrasonic sensor 221, transmitted through the reference foil 65 and received by the second calibration ultrasonic sensor 222, and the first received signal $S_K$ is computed based on the five first sample received signals $S_{K1}$-$S_{K5}$. Therefore, when the calibration ultrasonic sensor set 220 performs calibration, using the reference foil 65, the first received signal $S_K$ having improved reliability and the optimum magnitude is obtained, even in the case where there are variations in the attenuation factors (first sample received signals $S_{K1}$-$S_{K5}$) of ultrasonic waves US transmitted through the reference foil 65, among the ultrasonic wave transmittable regions C1, C2, C3, C4, C5 of the reference foil 65.

Strictly speaking, if the calibration ultrasonic sensor set 220 allows ultrasonic waves US to be transmitted through different regions of one reference foil 65 placed between the first calibration ultrasonic sensor 221 and the second calibration ultrasonic sensor 222, variations may arise in the attenuation factors (first sample received signals $S_{K1}$-$S_{K5}$) of ultrasonic waves US, as in the case where $S_{KA} \neq S_{KB} \neq S_C$ or $S_{KA} \approx S_{KB} \neq S_C$, in the above-indicated Eq. (6), Eq. (8) and Eq. (10), for example. If the attenuation factor of ultrasonic waves US varies depending on the region of the reference foil 65 through which the ultrasonic waves US are transmitted, when the calibration ultrasonic sensor set 220 performs calibration, the reliability of the first received signal $S_K$ is reduced, and the measurement condition values to be reflected by the actual-measurement ultrasonic sensor set 220 cannot be obtained with high accuracy.

On the other hand, in the ultrasonic measuring method of the second embodiment, the first sample received signals $S_{K1}$-$S_{k5}$ are obtained with respect to the five ultrasonic wave transmittable regions C1-C5 of the reference foil 65, and the first received signal $S_K$ (the attenuation factor of ultrasonic waves transmitted through the reference foil) is obtained by computation, such as a least square method, based on the obtained five first sample received signals $S_{K1}$-$S_{K5}$. Therefore, the first received signal $S_K$ has improved reliability and the optimum magnitude. In particular, it is preferable to correct or update respective pieces of data as measurement results of the temperature, density and air pressure of the air layer AR through which ultrasonic waves US are propagated between the first calibration ultrasonic sensor 221 and the second calibration ultrasonic sensor 222, each time the thickness (basis weight) of the electrode 60 (electrode paste 62) is measured and calculated by the actual-measurement ultrasonic sensor set 220. If the first receive signal is obtained in a condition where the above-indicated respective pieces of data are corrected or updated each time the basis weight of the electrode paste 62 is calculated, the reliability of the first received signal $S_K$ is further improved, and its accuracy is kept at a high level.

The attenuation factor of ultrasonic waves US transmitted through the reference foil 65 is obtained with improved reliability and high accuracy; therefore, when the thickness (basis weight) of the electrode paste 62 is measured and calculated by the actual-measurement ultrasonic sensor set 210, the first received signal $S_K$ obtained with high accuracy, as well as the second received signal $S_X$, is reflected by measurement condition values of the actual-measurement ultrasonic sensor set 210, and the thickness (basis weight) of the electrode paste 62 can be calculated with further improved accuracy.

The ultrasonic measuring method of the second embodiment is characterized in that the third sample received signals $S_{Y1}$-$S_{Y5}$ corresponding to the five ultrasonic wave transmittable regions C1-C5 of the reference foil 65 are obtained as received signals of ultrasonic waves US sent from the first ultrasonic sensor 211, transmitted through the reference foil 65 and received by the second ultrasonic sensor 212, and the third received signal $S_Y$ is computed based on the five third sample received signals $S_{Y1}$-$S_{Y5}$. Therefore, when machine differences between the calibration ultrasonic sensor set 220 and the actual-measurement ultrasonic sensor set 210 are determined, using the reference foil 65, the third received signal $S_Y$ having improved reliability and the optimum magnitude is obtained, even in the case where there are variations in the attenuation factors (the third sample received signals $S_{Y1}$-$S_{Y5}$) of ultrasonic waves US transmitted through the reference foil 65, among the ultrasonic wave transmittable regions C1, C2, C3, C4, C5 of the reference foil 65. Since the third received signal $S_Y$ (the attenuation factor of ultrasonic waves transmitted through the reference foil 65) is obtained by computation, such as a least square method, based on the obtained five third sample received signals $S_{Y1}$-$S_{Y5}$, the third received signal $S_Y$ has improved reliability and the optimum magnitude even when there are variations in the above-indicated plurality of third sample received signals $S_{Y1}$-$S_{Y5}$.

In particular, it is preferable, in relation to the calibration ultrasonic sensor set 220, that the first received signal $S_K$ is computed based on five first sample received signals $S_{K1}$-$S_{K5}$ obtained from five ultrasonic wave transmittable regions C1-C5 of the reference foil 65. If machine differences between the calibration ultrasonic sensor set 220 and the actual-measurement ultrasonic sensor set 210 are determined from the thus obtained first received signal $S_K$ and third received signal $S_Y$, a result of determination on the machine differences can be obtained with further improved accuracy.

In the ultrasonic measuring system 201 having at least one set of ultrasonic sensors each of which consists of the first ultrasonic sensor 211 and the second ultrasonic sensor 212, the first ultrasonic sensor 211 is placed, via the air layer AR, on one side of the electrode 60 formed by applying the electrode paste 62 by coating to both surfaces of the metal foil 61 wound in the form of a roll, as viewed in the thickness direction Z of the electrode 60, while the second ultrasonic sensor 212 is placed on the other side of the electrode 60, via the air layer AR. The ultrasonic measuring system 201 measures the thickness (basis weight) of the electrode paste 62, by transmitting ultrasonic waves US between the first ultrasonic sensor 211 and the second ultrasonic sensor 212. In the ultrasonic measuring system 201, the above-indicated at least one set of ultrasonic sensors includes at least one set of actual-measurement ultrasonic sensors 210 for measuring the thickness of the electrode paste 62, and the calibration ultrasonic sensor set 220 consisting of the first calibration ultrasonic sensor 221 and the second calibration ultrasonic sensor 222, aside from the first ultrasonic sensor 211 and the second ultrasonic sensor 212. During measurement of the basis weight of the electrode paste 62, the actual-measurement ultrasonic sensor set 210 sends and receives ultrasonic waves US, based on the measurement condition values obtained through calibration by the calibration ultrasonic sensor set 220. Therefore, when the thickness of the electrode paste 62 is measured on the production line on which the electrode 60 is produced by coating the metal foil 61 with the electrode paste 62, in the battery production process, error factors of the measurement accuracy due to self-heating of the ultrasonic sensors and changes in the temperature of the air layers AR are excluded or eliminated, during the actual measurement, and the thickness of the electrode paste 62 can be measured with high accuracy.

With the first and second ultrasonic sensors 211, 212 and the first and second calibration ultrasonic sensors 221, 222 operating in the same timing, even if the first and second ultrasonic sensors 211, 212 are self-heated with a lapse of the operating time, the first and second calibration ultrasonic sensors 221, 222 are also self-heated in the same fashion as the first and second ultrasonic sensors 211, 212. In this case, there is almost no difference between the temperatures of the self-heated first and second ultrasonic sensors 211, 212 and the temperatures of the self-heated first and second calibration ultrasonic sensors 221, 222. Therefore; even if the wavelength of ultrasonic waves US received by the calibration ultrasonic sensor set 220 changes due to self-heating, the wavelength of the received ultrasonic waves US in the actual-measurement ultrasonic sensor set 210 also changes in the same manner as that of the calibration ultrasonic sensor set 220. Thus, there arises almost no difference between the wavelength of the actual-measurement ultrasonic sensor set 210 and the wavelength of the calibration ultrasonic sensor set 220, and the thickness of the electrode paste 62 can be measured, assuring high measurement accuracy, even if the first and second calibration ultrasonic sensors 221, 222 of the calibration ultrasonic sensor set 220 and the first and second ultrasonic sensors 211, 212 of the actual-measurement ultrasonic sensor set 210 are both self-heated.

Thus, in the ultrasonic measuring system 201 of the second embodiment, error factors of the measurement accuracy due to self-heating of the ultrasonic sensors and changes in the temperature of the air layers AR can be excluded or eliminated, as in the first embodiment, so that the thickness (basis weight) of the electrode paste 62 applied by coating to the electrode 60 produced on the production line can be advantageously measured on the production line with high accuracy.

The ultrasonic measuring system 201 of the second embodiment is characterized by further including the reference foil holding member 270 that holds the reference foil 65, and the drive unit 280 that operates the reference foil holding member 270, and also stops its operation, and that the reference foil 65 held by the reference foil holding member 270 is positioned by the drive unit 280 so as to be movable relative to the first ultrasonic sensor 211 and the second ultrasonic sensor 212, within a range in which the reference foil 65 intersects with the imaginary line M that connects the centers of the opposed first ultrasonic sensor 211 and second ultrasonic sensor 212, or so as to be movable relative to the first calibration ultrasonic sensor 221 and the second calibration ultrasonic sensor 222, within a range in which the reference foil 65 intersects with the imaginary line N that connects the centers of the opposed first calibration ultrasonic sensor 221 and second calibration ultrasonic sensor 222. With this arrangement, when the calibration ultrasonic sensor set 220 performs calibration, using a single reference foil 65 placed between the first calibration ultrasonic sensor 221 and the second calibration ultrasonic sensor 222, ultrasonic waves US propagated between the first calibration ultrasonic sensor 221 and the second calibration ultrasonic sensor 222 are transmitted through the five ultrasonic wave transmittable regions C1-C5 of the reference foil 65, in the second embodiment. Thus, the attenuation factor of the transmitted ultrasonic waves US can be calculated for each region of the ultrasonic wave transmittable regions C1, C2, C3, C4, C5 of the single reference foil 65 through which the ultrasonic waves US are transmitted.

When machine differences between the calibration ultrasonic sensor set 220 and the actual-measurement ultrasonic sensor set 210 are determined, using the reference foil 65, ultrasonic waves US propagated between the first ultrasonic sensor 211 and the second ultrasonic sensor 212 are transmitted through the five ultrasonic wave transmittable regions C1-C5 of the reference foil 65. Thus, the attenuation factor of the transmitted ultrasonic waves US can be calculated for each region of the ultrasonic wave transmittable regions C1, C2, C3, C4, C5 of the single reference foil 65 through which the ultrasonic waves US are transmitted. Consequently, calibration performed by the calibration ultrasonic sensor set 220, and determination of machine differences between the first calibration ultrasonic sensor 221 and second calibration ultrasonic sensor 222, and the first ultrasonic sensor 211 and second ultrasonic sensor 212, can be accomplished with improved accuracy.

The ultrasonic measuring system 201 of the second embodiment is characterized by further including the rotary encoder 290 that detects positions on the operating reference foil holding member 270, at which the imaginary line M, N passes through the centers C1$a$, C2$a$, C3$a$, C4$a$, C5$a$ of the ultrasonic wave transmittable regions. C1-C5 as predetermined positions within the reference foil 65. Therefore, when calibration is repeatedly carried out a plurality of times, using the reference foil 65 placed between the first calibration ultrasonic sensor 221 and the second calibration ultrasonic sensor 222, the rotary encoder 290 can set the centers C1$a$, C2$a$, C3$a$, C4$a$, C5$a$ of the ultrasonic wave transmittable regions C1-C5 of the reference foil 65 through which the imaginary line N passes; to the same positions, for each cycle of calibration. Consequently, highly accurate calibration can be achieved. Also, when machine differences between the calibration ultrasonic sensor set 220 and the actual-measurement ultrasonic sensor set 210 are repeatedly determined a plurality of times, the rotary encoder 290 can set the centers C1*a*, C2*a*, C3*a*, C4*a*, C5*a* of the ultrasonic wave transmittable regions C1-C5 of the reference foil 65 through which the imaginary line M, N passes, to the same positions, for each cycle of determination of machine differences. Consequently, research on machine differences between the calibration ultrasonic sensor set 220 and the actual-measurement ultrasonic sensor set 210 can be accomplished with improved reliability.

While the invention has been described in terms of the first and second embodiments thereof, the invention is not limited to the first and second embodiments, but may be embodied with changes as needed, without departing from the principle of the invention. In the first embodiment, the electrode 60 is interposed between the first ultrasonic sensor 11 and the second ultrasonic sensor 12 of the actual-measurement ultrasonic sensor set 10, and the basis weight of the electrode 60 is calculated, based on the received signal of ultrasonic waves (transmitted waves) transmitted through the electrode 60, between the first ultrasonic sensor 11 and the second ultrasonic sensor 12. Similarly, the reference foil 65 is interposed between the first calibration ultrasonic sensor 21 and the second calibration ultrasonic sensor 22 of the calibration ultrasonic sensor set 20, and calibration is performed by the first calibration ultrasonic sensor 21 and the second calibration ultrasonic sensor 22, using the reference foil 65.

Figure 15:
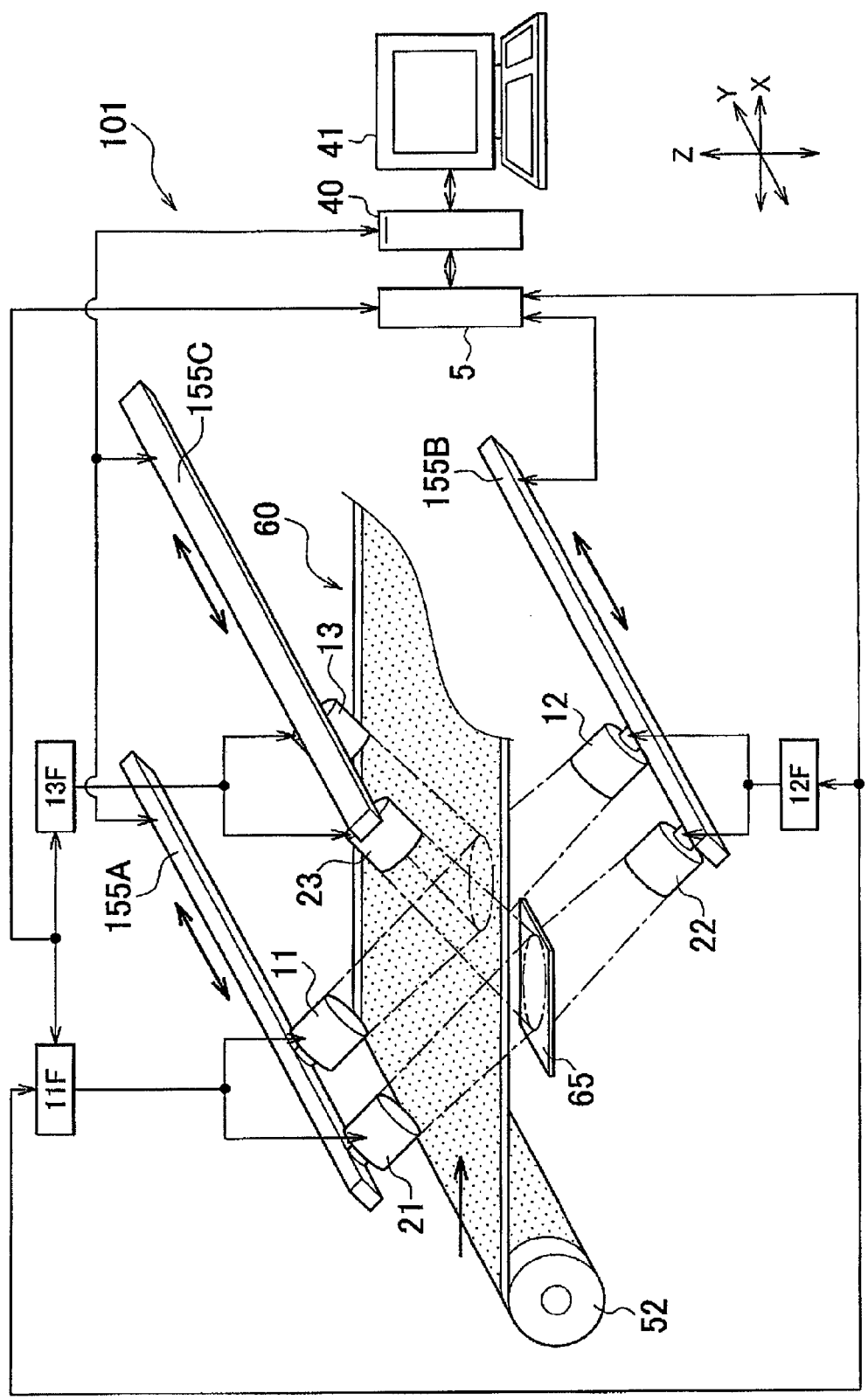
FIG. 15 is a schematic view useful for explaining the construction of an ultrasonic measuring system according to a modified example of the first embodiment of the invention.

However, the ultrasonic measuring system may be modified such that each of the actual-measurement ultrasonic sensor set and the calibration ultrasonic sensor set consists of three ultrasonic sensors as one set. The modified embodiment will be specifically described with reference to FIG. 15. FIG. 15 is a schematic view illustrating the construction of an ultrasonic measuring system 101 according to the modified embodiment of the invention. In the ultrasonic measuring system 101, as shown in FIG. 15, the actual-measurement ultrasonic sensor set 10 includes a third ultrasonic sensor 13, in addition to the first and second ultrasonic sensors 11, 12, and the calibration ultrasonic sensor set 20 includes a third calibration ultrasonic sensor 23, in addition to the first and second ultrasonic sensors 21, 22. The first ultrasonic sensor 11 and the first calibration ultrasonic sensor 21 are mounted on a first upper slide shaft 155A, and the third ultrasonic sensor 13 and the third calibration ultrasonic sensor 23 are mounted on a second upper slide shaft 155C. The second ultrasonic sensor 12 and the second calibration ultrasonic sensor 22 are mounted on a lower slide shaft 155B.

The first ultrasonic sensor 11 and the first calibration ultrasonic sensor 21, and the third ultrasonic sensor 13 and the third calibration ultrasonic sensor 23 are placed on one side (the upper side in FIG. 15) of the electrode 60 via an air layer. More specifically, the above-indicated ultrasonic sensors 11, 21, 13, 23 are positioned such that ultrasonic waves are regularly reflected between the first ultrasonic sensor 11 and the third ultrasonic sensor 13, and between the first calibration ultrasonic sensor 21 and the third calibration ultrasonic sensor 23. The second ultrasonic sensor 12 and the second calibration ultrasonic sensor 22 are placed on the other side (the lower side in FIG. 15) of the electrode 60 via an air layer, so as to face the first ultrasonic sensor 11 and the first calibration ultrasonic sensor 21, respectively, in the axial directions of the sensors 11, 21, via the electrode 60.

Thus, when each of the actual-measurement ultrasonic sensor set and the calibration ultrasonic sensor set consists of three ultrasonic sensors as one set, the thickness of the electrode paste (coating material) on one surface of the electrode 60 can be measured based on a received signal representing transverse waves of ultrasonic waves received by the third ultrasonic sensor 13. At the same time, the thickness of the electrode paste on the other surface of the electrode 60 can be measured based on a received signal representing longitudinal waves of ultrasonic waves received by the second ultrasonic sensor 12. Thus, the equipment for measuring the thickness (basis weight) of the electrode paste on both surfaces of the electrode 60 can be simplified. Needless to say, as in the first embodiment, error factors in calibration of the first, second and third ultrasonic sensors 11, 12, 13 by means of the first, second and third calibration ultrasonic sensors 21, 22, 23, and error factors due to machine differences between the first, second and third ultrasonic sensors 11, 12, 13 and the first, second and third calibration ultrasonic sensors 21, 22, 23 can be excluded or reduced.

In the second embodiment, the rotary encoder 290 detects the positions at which the imaginary line M, N passes through the centers C1*a*, C2*a*, C3*a*, C4*a*, C5*a* of the ultrasonic wave transmittable regions C1-C5 as predetermined positions within the reference foil 65. However, if a servomotor that incorporates a rotary encoder is used as the motor of the drive unit, and the rotary encoder is operable to detect the amount of rotation of the servomotor, it is possible to detect the positions at which the imaginary line passes through the predetermined positions within the reference foil, without using the positioning device.

In the second embodiment, in order to obtain the plurality of first sample received signals $S_{K1}$ . . . (or the third received signals $S_{Y1}$ . . . ) of ultrasonic waves US sent from the first ultrasonic sensor 211 (or the first calibration ultrasonic sensor 221) and received by the second ultrasonic sensor 212 (or the second calibration ultrasonic sensor 222), the drive unit 280 rotates the reference foil 65 held by the reference foil holding member 270, so that ultrasonic waves are transmitted through the ultrasonic wave transmittable regions C1-C5. However, while the reference foil 65 is kept fixed, as in the first embodiment, the actual-measurement ultrasonic sensor set 210 (or the calibration ultrasonic sensor set 220) may be moved along the upper slide shaft 55A and the lower slide shaft 55B, within a range in which ultrasonic waves propagated from the actual-measurement ultrasonic sensor set 210 (or the calibration ultrasonic sensor set 220) can be transmitted through the reference foil 65. It is thus possible to obtain the first sample received signals $S_{K1}$ . . . or the third received signals $S_{Y1}$ . . . corresponding to a plurality of regions arranged in a row within the reference foil 65, without providing any drive unit.

In the second embodiment, the reference foil 65 is held by the reference foil holding member 270, and is rotated by the drive unit 280 so that the plurality of first sample received signals $S_{K1}$ . . . or the plurality of third received signals $S_{Y1}$ . . . are obtained. In the first embodiment in which the frequency band of the ultrasonic sensors that constitute the actual-measurement ultrasonic sensor set and the calibration ultrasonic sensor set is different from that of the second embodiment, too, the ultrasonic measuring system may be arranged such that the reference foil is held by a holding member, and is rotated by a drive unit, so that a plurality of first sample received signals, a plurality of third sample received signals, etc. can be obtained.

While the actual-measurement ultrasonic sensor set 210 and the calibration ultrasonic sensor set 220 are not provided with actual-measurement sensor covers and calibration sensor covers, respectively, in the second embodiment, it is preferable to provide each of the first and second calibration ultrasonic sensors of the calibration ultrasonic sensor set with a calibration sensor cover, and provide each of the first and second ultrasonic sensors of the actual-measurement ultrasonic sensor set with an actual-measurement sensor cover, as in the first embodiment.

In the second embodiment, ultrasonic waves are transmitted through five ultrasonic wave transmittable regions C1-C5 located on the pitch circle R, within the reference foil 65 having a square shape, so as to conduct calibration and research on machine differences. However, the shape of the reference foil, the number and positions of regions of the reference foil through which ultrasonic waves are transmitted, are not limited to those of the first embodiment and second embodiment, but may be changed as appropriate.

While the invention has been described with reference to example embodiments thereof, it is to be understood that the invention is not limited to the described example embodiments or constructions. To the contrary, the invention is intended to cover various modifications and equivalent arrangements. In addition, while the various elements of the example embodiments are shown in various combinations and configurations, other combinations and configurations, including more, less or only a single element, are also within the scope of the invention.

What is claimed is:

1. An ultrasonic measuring method, comprising:
providing at least one set of ultrasonic sensors, each of which comprises a pair of first ultrasonic sensor and second ultrasonic sensor, and placing the first ultrasonic sensor on one side of a coated product formed by applying a coating material by coating to one surface or both surfaces of a substrate made of metal and wound in the form of a roll, as viewed in a thickness direction of the coated product, via an air layer, while placing the second ultrasonic sensor on the other side of the coated product, via an air layer; and
measuring a thickness of the coating material by transmitting ultrasonic waves between the first ultrasonic sensor and the second ultrasonic sensor, wherein
said at least one set of ultrasonic sensors comprises at least one actual-measurement ultrasonic sensor set that measures the thickness of the coating material, and a calibration ultrasonic sensor set comprising a pair of first calibration ultrasonic sensor and second calibration ultrasonic sensor, aside from the first ultrasonic sensor and the second ultrasonic sensor; and
the calibration ultrasonic sensor set performs calibration, during measurement of the thickness of the coating material, and the actual-measurement ultrasonic sensor set calculates the thickness of the coating material, using a measurement condition value obtained by the calibration ultrasonic sensor set.

2. The ultrasonic measuring method according to claim 1, wherein:
flat-type ultrasonic sensors that permit propagation of unfocused ultrasonic waves are used as the first calibration ultrasonic sensor and the second calibration ultrasonic sensor of the calibration ultrasonic sensor set; and
flat-type ultrasonic sensors that permit propagation of unfocused ultrasonic waves are used as the first ultrasonic sensor and the second ultrasonic sensor of each of said at least one actual-measurement ultrasonic sensor set.

3. The ultrasonic measuring method according to claim 1, wherein:
prior to actual measurement by the actual-measurement ultrasonic sensor set, a reference foil used for calibration is placed between the first calibration ultrasonic sensor and the second calibration ultrasonic sensor of the calibration ultrasonic sensor set, and ultrasonic waves sent from the first calibration ultrasonic sensor are transmitted through the reference foil, so that a first received signal representing ultrasonic waves received by the second calibration ultrasonic sensor is obtained in advance as the measurement condition value; and
the actual-measurement ultrasonic sensor set obtains a second received signal representing ultrasonic waves transmitted through the coated product between the first ultrasonic sensor and the second ultrasonic sensor, and the thickness of the coating material is calculated based on a relative ratio of the first received signal and the second received signal.

4. The ultrasonic measuring method according to claim 3, wherein:
a plurality of first sample received signals corresponding to a plurality of regions of the reference foil are obtained as received signals of ultrasonic waves sent from the first calibration ultrasonic sensor, transmitted through the reference foil, and received by the second calibration ultrasonic sensor; and
the first received signal is computed based on the plurality of first sample received signals.

5. The ultrasonic measuring method according to claim 3, wherein the actual-measurement ultrasonic sensor set is moved to a position at which the reference foil is placed, and obtains a third received signal representing ultrasonic waves that are sent from the first ultrasonic sensor, transmitted through the reference foil, and received by the second ultrasonic sensor.

6. The ultrasonic measuring method according to claim 5, wherein:
a plurality of third sample received signals corresponding to a plurality of regions of the reference foil are obtained as received signals of ultrasonic waves sent from the first ultrasonic sensor, transmitted through the reference foil, and received by the second ultrasonic sensor; and
the third received signal is computed based on the plurality of third sample received signals.

7. The ultrasonic measuring method according to claim 1, wherein the first calibration ultrasonic sensor and the second calibration ultrasonic sensor, and the first ultrasonic sensor and the second ultrasonic sensor, send and receive ultrasonic waves in synchronization with each other.

8. An ultrasonic measuring system, comprising:
at least one actual-measurement ultrasonic sensor set each comprising a pair, of first ultrasonic sensor and second ultrasonic sensor, said first ultrasonic sensor being placed on one side of a coated product formed by applying a coating material by coating to one surface or both surfaces of a substrate made of metal and wound in the form of a roll, as viewed in a thickness direction of the coated product, via an air layer, said second ultrasonic sensor being placed on the other side of the coated product, via an air layer, each of said at least one actual-measurement ultrasonic sensor set being operable to measure a thickness of the coating material by transmitting ultrasonic waves between the first ultrasonic sensor and the second ultrasonic sensor; and
a calibration ultrasonic sensor set comprising a pair of first calibration ultrasonic sensor and second calibration ultrasonic sensor, aside from the first ultrasonic sensor and the second ultrasonic sensor, wherein
the actual-measurement ultrasonic sensor set sends and receives ultrasonic waves, based on a measurement condition value obtained through calibration by the calibration ultrasonic sensor set, during actual measurement of the thickness of the coating material.

9. The ultrasonic measuring system according to claim 8, wherein:
flat-type ultrasonic sensors that permit propagation of unfocused ultrasonic waves are used as the first calibration ultrasonic sensor and the second calibration ultrasonic sensor of the calibration ultrasonic sensor set; and
flat-type ultrasonic sensors that permit propagation of unfocused ultrasonic waves are used as the first ultrasonic sensor and the second ultrasonic sensor of the actual-measurement ultrasonic sensor set.

10. The ultrasonic measuring system according to claim 8, further comprising a control unit that controls sending and receiving of ultrasonic waves and measurement conditions, in the calibration ultrasonic sensor set and the actual-measurement ultrasonic sensor set, wherein the control unit feeds back the measurement condition value obtained by the calibration ultrasonic sensor set, to the actual-measurement ultrasonic sensor set.

11. The ultrasonic measuring system according to claim 8, wherein:
a reference foil used for calibration is placed along with the coated product; and
the calibration ultrasonic sensor set is mounted so as to be movable at least within a range between a first position at which the reference foil is placed, and a second position at which only an air layer is present between the first calibration ultrasonic sensor and the second calibration ultrasonic sensor.

12. The ultrasonic measuring system according to claim 11, further comprising:
a holding member that holds the reference foil; and
a drive unit that operates the holding member, and stops operation thereof, wherein
the reference foil held by the holding member is positioned by the drive unit so as to be movable relative to the first ultrasonic sensor and the second ultrasonic sensor, within a range in which the reference foil intersects with an imaginary line that connects a center of the first ultrasonic sensor with a center of the second ultrasonic sensor opposed to the first ultrasonic sensor, or is positioned by the drive unit so as to be movable relative to the first calibration ultrasonic sensor and the second calibration ultrasonic sensor, within a range in which the reference foil intersects with an imaginary line that connects a center of the first calibration ultrasonic sensor with a center of the second calibration ultrasonic sensor opposed to the first calibration ultrasonic sensor.

13. The ultrasonic measuring system according to claim 12, further comprising:
a positioning device that detects positions on the holding member that is in operation, at which positions the imaginary line intersects with predetermined regions of the reference foil.

14. The ultrasonic measuring system according to claim 11, wherein the actual-measurement ultrasonic sensor set is mounted so as to be movable at least within a range between the first position, and a third position at which the coated product is placed.

15. The ultrasonic measuring system according to claim 11, wherein:
the substrate wound in the form of a roll has a large length, and the reference foil and the coated product are arranged side by side in a width direction of the substrate, which is perpendicular to a longitudinal direction parallel to long sides of the substrate and a thickness direction of the substrate; and
the calibration ultrasonic sensor set and the actual-measurement ultrasonic sensor set are arranged to move in a direction parallel to the width direction of the substrate.

16. The ultrasonic measuring system according to claim 11, wherein each of the first calibration ultrasonic sensor and the second calibration ultrasonic sensor of the calibration ultrasonic sensor set is provided with a cylindrical calibration sensor cover that surrounds an air layer between an ultrasonic vibration surface and the reference foil.

17. The ultrasonic measuring system according to claim 16, wherein the calibration sensor cover has a dual structure comprising an inner cylindrical cover, and an outer cylindrical cover located radially outwardly of the inner cylindrical cover, and the outer cylindrical cover is formed to be shorter than the inner cylindrical cover, as measured in a direction parallel to a thickness direction of the substrate, so that the outer cylindrical cover is spaced by a larger difference from the reference foil or the coated product, than the inner cylindrical cover.

18. The ultrasonic measuring system according to claim 8, wherein each of the first ultrasonic sensor and the second ultrasonic sensor of the actual-measurement ultrasonic sensor set is provided with a cylindrical actual-measurement sensor cover that surrounds an air layer between an ultrasonic vibration surface and the coated product.

19. The ultrasonic measuring system according to claim 18, wherein the actual-measurement sensor cover has a dual structure comprising an inner cylindrical cover, and an outer cylindrical cover located radially outwardly of the inner cylindrical cover, and the outer cylindrical cover is formed to be shorter than the inner cylindrical cover, as measured in a direction parallel to a thickness direction of the substrate, so that the outer cylindrical cover is spaced by a larger difference from the reference foil or the coated product, than the inner cylindrical cover.

20. The ultrasonic measuring system according to claim 8, wherein the substrate comprises a metal foil used in an electrode of a battery as the coated product, and the coating material comprises an electrode paste applied by coating to the metal foil.

* * * * *